US008685730B2

(12) United States Patent
Odorico et al.

(10) Patent No.: US 8,685,730 B2
(45) Date of Patent: Apr. 1, 2014

(54) METHODS AND DEVICES FOR DIFFERENTIATING PLURIPOTENT STEM CELLS INTO CELLS OF THE PANCREATIC LINEAGE

(75) Inventors: Jon Odorico, Madison, WI (US); Xiaofang Xu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/492,244

(22) Filed: Jun. 8, 2012

(65) Prior Publication Data

US 2012/0264209 A1 Oct. 18, 2012

Related U.S. Application Data

(60) Continuation-in-part of application No. 12/825,281, filed on Jun. 28, 2010, now Pat. No. 8,247,229, which is a division of application No. 11/799,659, filed on May 2, 2007, now abandoned.

(60) Provisional application No. 61/495,817, filed on Jun. 10, 2011, provisional application No. 60/796,662, filed on May 2, 2006.

(51) Int. Cl.
*C12N 5/00* (2006.01)

(52) U.S. Cl.
USPC ............................ 435/377; 435/375; 435/376

(58) Field of Classification Search
None
See application file for complete search history.

(56) References Cited

U.S. PATENT DOCUMENTS

| 7,033,831 | B2 | 4/2006 | Fisk et al. |
| 7,045,353 | B2 | 5/2006 | Benvenisty |
| 7,148,062 | B2 | 12/2006 | Xu et al. |
| 7,510,876 | B2 | 3/2009 | D'Amour et al. |
| 7,534,608 | B2 | 5/2009 | Martinson et al. |
| 7,541,185 | B2 | 6/2009 | D'Amour et al. |
| 7,585,672 | B2 | 9/2009 | Odorico et al. |
| 7,700,571 | B2 * | 4/2010 | Ferrara et al. ............... 514/44 R |
| 7,985,585 | B2 | 7/2011 | D'Amour et al. |
| 8,247,229 | B2 | 8/2012 | Odorico et al. |
| 2007/0254359 | A1 | 11/2007 | Rezania et al. |
| 2011/0014703 | A1 | 1/2011 | Xu et al. |
| 2011/0081720 | A1 | 4/2011 | Odorico et al. |

FOREIGN PATENT DOCUMENTS

| WO | 2005097977 | A2 | 10/2005 |
| WO | 2006016999 | A1 | 2/2006 |

OTHER PUBLICATIONS

Bigas et al. Blood 1995;85:3127-33.*
European Patent Office, Communication, European Patent Application No. 07776639.2, Dec. 12, 2008.
Applicant, Response to Dec. 12, 2008 Communication, European Patent Application No. 07776639.2, Jan. 12, 2009.
European Patent Office, Communication, European Patent Application No. 07776639.2, Mar. 2, 2009.
Applicant, Response to Mar. 2, 2009 Communication, European Patent Application No. 07776639.2, Sep. 3, 2009.
European Patent Office, Communication, European Patent Application No. 07776639.2, May 17, 2010.
Applicant, Response to May 17, 2010 Communication, European Patent Application No. 07776639.2, Nov. 20, 2010.
European Patent Office, Communication, European Patent Application No. 07776639.2, Mar. 30, 2011.
Applicant, Response to Mar. 30, 2011 Communication, European Patent Application No. 07776639.2, Oct. 10, 2011.
European Patent Office, Communication, European Patent Application No. 07776639.2, Nov. 12, 2012.
Intellectual Property Office, Examination Report, Application No. GB 0821641.8, May 26, 2010.
Applicant, Response to May 26, 2010 Examination Report, Application No. GB 0821641.8, Nov. 20, 2010.
Israel Patent Office, Official Action, Israel Patent Application No. 194828, Dec. 9, 2010.
Applicant, Memorandum in Response to Official Action of Dec. 9, 2010, Israel Patent Application No. 194828, Apr. 3, 2011.
Israel Patent Office, Official Action, Israel Patent Application No. 194828, May 17, 2012.
Applicant, Memorandum in Response to Official Action of May 17, 2012, Israel Patent Application No. 194828, Sep. 5, 2012.
Japanese Patent Office, Official Action, Japanese Patent Application No. JP2009-509692, Aug. 29, 2012.
Swedish Patent Office, Official Action, Patent Application No. SE 0850111-6, May 7, 2009.
Applicant, Response to May 7, 2009 Official Action, Patent Application No. SE 0850111-6, Nov. 2, 2009.
Swedish Patent Office, Official Action, Patent Application No. SE 0850111-6, Jan. 26, 2010.
Applicant, Response to Jan. 26, 2010 Official Action, Patent Application No. SE 0850111-6, Jun. 1, 2010.
Swedish Patent Office, Official Action, Patent Application No. SE 0850111-6, Jul. 7, 2010.
Intellectual Property Office of Singapore, Written Opinion, Singapore Patent Application No. 200807930-3, Oct. 29, 2010.

(Continued)

*Primary Examiner* — Q. Janice Li
(74) *Attorney, Agent, or Firm* — Quarles & Brady LLP

(57) ABSTRACT

Methods and devices for culturing human pluripotent stem cells to produce cells of the pancreatic lineage are disclosed. The methods include steps of culturing the stem cells under conditions that induce the expression of mesendoderm/primitive streak and definitive endoderm markers in a chemically defined medium including an effective amount of i) fibroblast growth factor, ii) Activin A, and iii) bone morphogenetic protein. The methods further include the steps of culturing cells under conditions favoring the formation of at least one of intact embryoid bodies and pancreatic progenitor PDX1$^+$Ins$^-$ cells.

26 Claims, 24 Drawing Sheets

(56) References Cited

OTHER PUBLICATIONS

Applicant, Response to Oct. 29, 2010 Written Opinion, Singapore Patent Application No. 200807930-3, Mar. 21, 2011.
Intellectual Property Office of Singapore, Written Opinion, Singapore Patent Application No. 200807930-3, Nov. 24, 2011.
Applicant, Response to Nov. 24, 2011 Written Opinion, Singapore Patent Application No. 200807930-3, Apr. 23, 2012.
Intellectual Property Office of Singapore, Examination Report, Singapore Patent Application No. 200807930-3, Aug. 31, 2012.
Nostro, et al., Wnt, Activin, and BMP Signaling Regulate Distinct Stages in the Developmental Pathway from Embryonic Stem Cells to Blood, Cell Stem Cell, 2008, 2(1):60-71.
Oliver-Krasinski, et al., On the Origin of the B Cell, Genes & Development, 2008, 22:1998-2021.
Otonkoski, et al., Unique Basement Membrane Structure Human Pancreatic Islets: Implications, for B-Cell Growth and Differentiation, Diabetes, Obesity and Metabolism, 2008, 10(Suppl. 4):119-127.
Pera, Unnatural Selection of Cultured Human ES Cells?, Nature Biotechnology, 2004, 22(1):42-43.
Pera, et al., Regulation of Human Embryonic Stem Cell Differentiation by BMP-2 and Its Antagonist Noggin, Journal of Cell Science, 2004, 117:1269-1280.
Phillips, et al., Directed Differentiation of Human Embryonic Stem Cells Into the Pancreatic Endocrine Lineage, Stem Cells and Development, 2007, 16:561-578.
Rajagopal, et al., Insulin Staining of ES Cell Progeny from Insulin Uptake, Science, 2003, 299(5605):363.
Schuldiner, et al., Effects of Eight Growth Factors on the Differentiation of Cells Derived from Human Embryonic Stem Cells, PNAS, 2000, 97(21):11307-11312.
Segev, et al., Differentiation of Human Embryonic Stem Cells into Insulin-Producing Clusters, Stem Cells, 2004, 32:265-274.
Seymour, et al., SOX9 is Required for Maintenance of the Pancreatic Progenitor Cell Pool, PNAS, 2007, 104 (6):1865-1870.
Shim, et al., Directed Differentiation of Human Embryonic Stem Cells Towards a Pancreatic Cell Fate, Diabetologia, 2007, 50:1228-1238.
Sipione, et al., Insulin Expressing Cells from Differentiated Embryonic Stem Cells are not Beta Cells, Diabetologia, 2004, 47(3):499-508.
Smith, et al., Identification of a Potent Xenopus Mesoderm-Inducing Factor as a Homologue of Activin A, Nature, 1990, 345:729-731.
Stafford, et al., A Conserved Role for Retinoid Signaling in Vertebrate Pancreas Development, Dev. Genes Evol., 2004, 214:432-441.
Suarez-Pinzon, et al., Combination Therapy with Epidermal Growth Factor and Gastrin Induces Neogenesis of Human Islet B-Cells from Pancreatic Duct Cells and an Increase in Functional B-Cell Mass, Journal of Clinical Endocrinology & Metabolism, 2005, 90(6):3401-3409.
Sulzbacher, et al., Activin A-Induced Differentiation of Embryonic Stem Cells Into Endoderm and Pancreatic Progenitors—The Influence of Differentiation Factors and Culture Conditions, Stem Cell Reviews and Reports, 2009, 5(2):159-173.
Tada et al., Characterization of Mesendoderm: A Diverging Point of the Definitive Endoderm and Mesoderm in Embryonic Stem Cell Differentiation Culture, Development, 2005, 132:4363-4374.
Tam, et al., Building the Mouse Gastrula: Signals, Asymmetry and Lineages, Current Opinion in Genetics & Development, 2006, 16:419-425.
Touboul, et al., Generation of Functional Hepatocytes from Human Embryonic Stem Cells Under Chemically Defined Conditions that Recapitulate Liver Development, Hepatology, 2010, 51:1754-1765.
Shi, et al., Generation of Functional Insulin-Producing Cells from Human Embryonic Stem Cells In Vitro, Methods in Molecular Biology, 2010, 636:79-85.
Valdimarsdottir, et al., Functions of the TGFB Superfamily in Human Embryonic Stem Cells, APMIS, 2005, 113 (11-12):773-789.
Vallier, et al., Activin/Nodal and FGF Pathways Cooperate to Maintain Pluripotency of Human Embryonic Stem Cells, Journal of Cell Science, 2005, 118:4495-4509.
Vallier, et al., Early Cell Fate Decisions of Human Embryonic Stem Cells and Mouse Epiblast Stem Cells are Controlled by the Same Signalling Pathways, PLoS One, 2009, 4(6):e6082, 13 pages.
Vallier, et al., Signaling Pathways Controlling Pluripotency and Early Cell Fate Decisions of Human Induced Pluripotent Stem Cells, Stem Cells, 2009, 27:2655-2666.
Varga, et al., The Disparate Role of BMP in Stem Cell Biology, Oncogene, 2005, 24:5713-5721.
Vesque, et al., Development of Chick Axial Mesoderm: Specification of Prechordal Mesoderm by Anterior Endoderm-Derived TGFB Family Signalling, Development, 2000, 127:2795-2809.
Vukicevic, et al., Identification of Multiple Active Growth Factors in Basement Membrane Matrigel Suggests Caution in Interpretation of Cellular Activity Related to Extracellular Matrix Components, Experimental Cell Research, 1992, 202(1):1-8.
Wells, et al., Vertebrate Endoderm Development, Annu. Rev. Cell Dev. Biol., 1999, 15:393-410.
Wells, et al., Early Mouse Endoderm is Patterned by Soluble Factors from Adjacent Germ Layers, Development, 2000, 127:1563-1572.
Willems, et al., Patterning of Mouse Embryonic Stem Cell-Derived Pan-Mesoderm by Activin A/Nodal and Bmp4 Signaling Requires Fibroblast Growth Factor Activity, Differentiation, 2008, 76(7):745-759.
Xiao, et al., Activin A Maintains Self-Renewal and Regulates Fibroblast Growth Factor, Wnt, and Bone Morphogenic Protein Pathways in Human Embryonic Stem Cells, Stem Cells, 2006, 24:1476-1486.
Xu, et al., Basic Fibroblast Growth Factor Supports Undifferentiated Human Embryonic Stem Cell Growth Without Conditioned Medium, Stem Cells, 2005, 23:315-323.
Xu, et al., BMP4 Initiates Human Embryonic Stem Gel Differentiation to Trophoblast, Nature Biotechnology, 2002, 20:1261-1264.
Xu, et al., Basic FGF and Suppression of BMP Signaling Sustain Undifferentiated Proliferation of Human ES Cells, Nature Methods, 2005, 2(3):185-190.
Xu, et al., Endoderm and Pancreatic Islet Lineage Differentiation from Human Embryonic Stem Cells, Cloning and Stem Cells, 2006, 8(2):96-107.
Xu, et al., Activin, BMP and FGF Pathways Cooperate to Promote Endoderm and Pancreatic Lineage Cell Differentiation from Human Embryonic Stem Cells, Mechanisms of Development, 2011, 128:412-427.
Yasunaga, et al., Induction and Monitoring of Definitive and Visceral Endoderm Differentiation of Mouse ES Cells, Nature Biotechnology, 2005, 23(12):1542-1550.
Ying, et al., BMP Induction of Id Proteins Suppresses Differentiation and Sustains Embryonic Stem Cell Self-Renewal in Collaboration with STAT3, Cell, 2003, 115:281-292.
Yu, et al., Induced Pluripotent Stem Cell Lines Derived from Human Somatic Cells, Science, 2007, 318 (5858):1917-1920.
Zhang, et al., Short-term BMP-4 Treatment Initiates Mesoderm Induction in Human Embryonic Stem Cells, Blood, 2008, 111:1933-1941.
Zhou, et al., A Multipotent Progenitor Domain Guides Pancreatic Organogenesis, Developmental Cell, 2007, 13:103-114.
Zorn, et al., Vertebrate Endoderm Development and Organ Formation, Annu. Rev. Cell. Dev. Biol., 2009, 25:221-251.
PCT International Search Report, PCT/US2007/010662, Nov. 12, 2007.
PCT International Search Report, PCT/US2012/041610, Oct. 9, 2012.
Australian Government IP Australia, Examiner's First Report, Australian Patent Application No. 2007248609, Mar. 9, 2012.
Applicant, Examination Response, Australian Patent Application No. 2007248609, Sep. 27, 2012.
Canadian Intellectual Property Office, Examination Report, Patent Application No. 2,650,561, Jul. 25, 2012.
Abe, et al., Activin Receptor Signaling, Growth Factors, 2004, 22(2):105-110.

(56) References Cited

OTHER PUBLICATIONS

Ameri, et al., FGF2 Specifies hESC-Derived Definitive Endoderm into Foregut/Midgut Cell Lineages in a Concentration-Dependent Manner, Stem Cells, 2010, 28:45-56.

Assady, et al., Insulin Production by Human Embryonic Stem Cells, Diabetes, 2001,50:1691-1697.

Beattie, et al., Activin A Maintains Pluripotency of Human Embryonic Stem Cells in the Absence of Feeder Layers, Stem Cells, 2005, 23:489-495.

Blyszczuk, et al., Embryonic Stem Gets Differentiate into Insulin-Producing Cells Without Selection of Nestin-Expressing Cells, Int. J. Dev. Biol., 2004, 48:1095-1104.

Bonner-Weir, et al., In Vitro Cultivation of Human Islets from Expanded Ductal Tissue, PNAS, 2000, 97 (14):7999-8004.

Brolen, et al., Signals from the Embryonic Mouse Pancreas Induce Differentiation of Human Embryonic Stem Cells into Insulin-Producing B-Cell-Like Cells, Diabetes, 2005, 54:2867-2874.

Cabrera, et al., The Unique Cytoarchitecture of Human Pancreatic Islets has Implications for Islet Cell Function, PNAS, 2006, 103(7):2334-2339.

Cai, et al., Generation of Homogeneous PDX1+ Pancreatic Progenitors from Human ES Cell-derived Endoderm Cells, Journal of Molecular Cell Biology, 2010, 2:50-60.

Castaing, et al., Ex Vivo Analysis of Acinar and Endocrine Cell Development in the Human Embryonic Pancreas, Developmental Dynamics, 2005, 234:339-345.

Chan, et al., Live Cell Imaging Distinguishes Bona Fide Human iPS Cells from Partially Reprogrammed Cells, Nature Biotechnology, 2009, 27(11):1033-1038.

Cirulli, et al., E-Cadherin, NCAM, and EpCAM Expression in Human Fetal Pancreata, Transplantation Proceedings, 1995, 27(6):3335.

Cirulli, et al., KSA Antigen Ep-CAM Mediates Cell-Cell Adhesion of Pancreatic Epithelial Cells: Morphoregulatory Roles in Pancreatic Islet Development, Journal of Cell Biology, 1998, 140(6):1519-1534.

D'Amour, et al., Efficient Differentiation of Human Embryonic Stem Cells to Definitive Endoderm, Nature Biotechnology, 2005, 23(12):1534-1541.

D'Amour, et al., Production of Pancreatic Hormone-Expressing Endocrine from Human Embryonic Stem Cells, Nature Biotechnology, 2006, 24(11):1392-1401.

Finley, et al., BMP-4 Inhibits Neural Differentiation of Murine Embryonic Stem Cells, J. Neurobiol., 1999, 40:271-287.

Gamer, et al., Autonomous Endodermal Determination in Xenopus: Regulation of Expression of the Pancreatic Gene XIHbox 8, Developmental Biology, 1995, 171(1):240-251.

Gao, et al., Characterization of Endocrine Progenitor Cells and Critical Factors for Their Differentiation in Human Adult Pancreatic Cell Culture, Diabetes, 2003, 52:2007-2015.

Gradwohl, et al., Neurogenin3 is Required for the Development of the Four Endocrine Cell Lineages of the Pancreas, PNAS, 2000, 97(4):1607-1611.

Greber, et al., Fibroblast Growth Factor 2 Modulates Transforming Growth Factor B Signaling in Mouse Embryonic Fibroblasts and Human ESCs (hESCs) to Support hESC Self-Renewal, Stem Cells, 2007, 25:455-464.

Greber, et al., Conserved and Divergent Roles of FGF Signaling in Mouse Epiblast Stem Cells and Human Embryonic Stem Cells, Cell Stem Cell, 2010, 6:215-226.

Gu, et al., Direct Evidence for the Pancreatic Lineage: NGN3+ Cells are Islet Progenitors and are Distinct from Duct Progenitors, Development, 2002, 129:2447-2457.

Hansson, et al., A Late Requirement for Wnt and FGF Signaling During Activin-Induced Formation of Foregut Endoderm from Mouse Embryonic Stem Cells, Dev. Biol., 2009, 330(2):286-304.

Hay, et al., Highly Efficient Differentiation of hESCs to Functional Hepatic Endoderm Requires ActivinA and Wnt3a Signaling, PNAS, 2008, 105(34):12301-12306.

Jackson, et al., Differentiating Embryonic Stem Cells Pass Through 'Temporal Windows' That Mark Responsiveness to Exogenous and Paracrine Mesendoderm Inducing Signals, PLoS One, 2010, 5(5):e10706, 12 pages.

Jiang et al., Laminin-1 Promotes Differentiation of Fetal Mouse Pancreatic B-Cells, Diabetes, 1999, 48:722-730.

Jiang, et al., Generation of Insulin-Producing Islet-Like Clusters from Human Embryonic Stem Cells, Stem Cells, 2007, 25:1940-1953.

Johannesson, et al., FGF4 and Retinoic Acid Direct Differentiation of hESCs into PDX1-Expressing Foregut Endoderm in a Time- and Concentration-Dependent Manner, PLoS One, 2009, 4(3):e4194, 13 pages.

Jonsson, et al., Insulin-Promoter-Factor 1 is Required for Pancreas Development in Mice, Nature, 1994, 371:606-609.

Kahan, et al., Pancreatic Precursors and Differentiated Islet Cell Types from Murine Embryonic Stem Cells, Diabetes, 2003, 52:2016-2024.

Kattman, et al., Stage-Specific Optimization of Activin/Nodal and BMP Signaling Promotes Cardiac Differentiation of Mouse and Human Pluripotent Stem Cell Lines, Cell Stem Cell, 2011, 8:228-240.

Kroon, et al., Pancreatic Endoderm Derived from Human Embryonic Stem Cells Generates Glucose-Responsive Insulin-Secreting Cells In Vivo, Nature Biotechnology, 2008, 26(4):443-452.

Kubo, et al., Development of Definitive Endoderm from Embryonic Stem Cells in Culture, Development, 2004, 131:1651-1662.

Kumar, et al., Signals from Lateral Plate Mesoderm Instruct Endoderm Toward a Pancreatic Fate, Developmental Biology, 2003, 259(1):109-122.

Laflamme, et al., Cardiomyocytes Derived from Human Embryonic Stem Cells in Pro-Survival Factors Enhance Function of Infarcted Rat Hearts, Nature Biotechnology, 2007, 25(9):1015-1024.

Lammert, et al., Induction of Pancreatic Differentiation by Signals from Blood Vessels, Science, 2001, 294 (5544):564-567.

Lau, et al., Hedgehog Signaling in Pancreas Development and Disease, Cellular and Molecular Life Sciences, CMLS, 2006, 63(6):642-652.

Li, et al., Combined Activin A/LiCI/Noggin Treatment Improves Production of Mouse Embryonic Stem Cell-Derived Definitive Endoderm Cells, Journal of Cellular Biochemistry, 2011, 112:1022-1034.

Marchetti, et al., The Pancreatic Beta-Cell in Human Type 2 Diabetes, Nutrition, Metabolism & Cardiovascular Diseases, 2006, 16:S3-S6.

Matveyenko, et al., Inconsistent Formation and Nonfunction of Insulin-Positive Cells from Pancreatic Endoderm Derived from Human Embryonic Stem Cells in Athymic Nude Rats, Am. J. Physiol. Endocrinol. Metab., 2010, 299:E713-E720.

McLean, et al., Activin A Efficiently Specifies Definitive Endoderm from Human Embryonic Stem Cells Only When Phosphatidylinositol 3-Kinase Signaling is Suppressed, Stem Cells, 2007, 25:29-38.

Micallef, et al., Endocrine Cells Develop Within Pancreatic Bud-Like Structures Derived from Mouse ES Cells Differentiated in Response to BMP4 and Retinoic Acid, Stem Cell Research, 2007, 1(1):25-36.

Miller, et al., Islet Formation During the Neonatal Development in Mice, PLoS One, 2009 4(11):e7739, 9 pages.

Mizusawa, et al., Differentiation Phenotypes of Pancreatic islet B- and a-Cells are Closely Related with Homeotic Genes and a Group of Differentially Expressed Genes, Gene, 2004, 331:53-63.

Moritoh, et al., Analysis of Insulin-Producing Cells During In Vitro Differentiation from Feeder-Free Embryonic Stem Cells, Diabetes, 2003, 52:1163-1168.

Morrison, et al., Anterior Definitive Endoderm from ESCs Reveals a Role for FGF Signaling, Cell Stem Cell, 2008, 3(4):402-415.

(56) References Cited

OTHER PUBLICATIONS

Nikolova, et al., The Vascular Basement Membrane: A Niche for Insulin Gene Expression and B Cell Proliferation, Developmental Cell, 2006, 10(3):397-405.

Ninomiya, et al., Endoderm Differentiation and Inductive Effect of Activin-Treated Ectoderm in Xenopus, Develop. Growth Differ., 1999, 41:391-400.

Nishimura, et al, A Switch from MafB to MafA Expression Accompanies Differentiation to Pancreatic B-Cells, Dev. Biol., 2006, 293(2):526-539.

Niwa, et al., Quantitative Expression of Oct-3/4 Defines Differentiation, Dedifferentiation or Self-Renewal of ES Cells, Nature Genetics, 2000, 24:372-376.

* cited by examiner

METHODS AND DEVICES FOR DIFFERENTIATING PLURIPOTENT STEM CELLS INTO CELLS OF THE PANCREATIC LINEAGE

CROSS-REFERENCE TO RELATED APPLICATIONS

This application claims priority to U.S. Patent Ser. No. 61/495,817, filed Jun. 10, 2011. This application is a continuation-in-part of U.S. patent Ser. No. 12/825,281, filed Jun. 28, 2010 now U.S. Pat. No. 8,247,229, which is a divisional of U.S. patent Ser. No. 11/799,659, filed May 2, 2007, now abandoned which claims priority to U.S. Patent Ser. No. 60/796,662, filed May 2, 2006. Each of these applications is incorporated by reference herein in their entireties.

STATEMENT REGARDING FEDERALLY SPONSORED RESEARCH OR DEVELOPMENT

This invention was made with government support under HHSN309200582085C and DK078889 awarded by the National Institutes of Health. The government has certain rights in the invention.

BACKGROUND OF THE INVENTION

Type I diabetes is an autoimmune disease of humans caused by destruction of pancreatic islet β cells. Transplantations of whole pancreas or isolated islet cells are effective treatments for Type I diabetes to restore insulin independence, when combined with immunosuppressive therapy. Successful transplantation of isolated islets from human cadaver donors is a proof-in-principle that a cell-based therapy for human diabetes can be successful. However, the lack of available organs and islet cells has restricted this therapy to very few patients. The amount of islet cells which can be harvested from human cadavers is extremely limited. Therefore, technologies capable of producing significant quantities of cells of the pancreatic lineage are highly desirable.

Stem cells are cells that are capable of differentiating into many cell types. Embryonic stem cells are derived from embryos and are potentially capable of differentiation into all of the differentiated cell types of a mature body. Certain types of stem cells are "pluripotent," which refers to their capability of differentiating into many cell types. One type of pluripotent stem cell is the human embryonic stem cell (hESC), which is derived from a human embryonic source. Human embryonic stem cells are capable of indefinite proliferation in culture, and therefore, are an invaluable resource for supplying cells and tissues to repair failing or defective human tissues in vivo.

Similarly, induced pluripotent stem (iPS) cells, which may be derived from non-embryonic sources, can proliferate without limit and differentiate into each of the three embryonic germ layers. It is understood that iPS cells behave in culture essentially the same as ESCs. Human iPS cells and ES cells express one or more pluripotent cell-specific markers, such as Oct-4, SSEA-3, SSEA-4, Tra 1-60, Tra 1-81, and Nanog (Yu et al. *Science*, Vol. 318. No. 5858, pp. 1917-1920 (2007)). Also, recent findings of Chan, suggest that expression of Tra 1-60, DNMT3B, and REX1 can be used to positively identify fully reprogrammed human iPS cells, whereas alkaline phosphatase, SSEA-4, GDF3, hTERT, and NANOG are insufficient as markers of fully reprogrammed human iPS cells. (Chan et al., *Nat. Biotech.* 27:1033-1037 (2009)). Subsequent references herein to hESCs and the like are intended to apply with equal force to iPS cells.

One of most significant features of hESCs is their ability to self-renew: hESCs can proliferate into multiple progeny hESCs, each having the full potential of its immediate ancestor. In other words, the progeny are pluripotent and have all the developmental and proliferative capacity of the parental cell. Self-renewal appears mutually exclusive with differentiation, as only undifferentiated hESCs are capable of indefinite self-renewal. Upon commitment toward any cell lineage, the attribute of perpetual self-renewal is lost. Therefore, until culture conditions are discovered that provide the ability to direct the commitment and subsequent differentiation of hESCs to a desired cell lineage, care must be taken to maintain the cells in an undifferentiated state.

Under nonselective culture conditions, it has been previously demonstrated that a wide variety of stem cells, including mouse embryonic stem cells and hESCs, differentiate spontaneously into cells of many lineages including the pancreatic lineage. Such differentiated cells can express the pancreatic duodenal homeobox 1 (PDX1) gene, a transcription factor specifying the pancreatic lineage, and can also express insulin. However, without selective conditions, stem cells will spontaneously and simultaneously differentiate in the same culture dish into a wide variety of different lineages with only a small proportion of the cells being differentiated towards any particular lineage.

Culture systems that allow the spontaneous differentiation of hESCs into insulin-staining cells have been reported (Assady, S. et al., Insulin production by human embryonic stem cells. Diabetes 50, 1691-1697 (2001); and Segev, H. et al., Differentiation of human embryonic stem cells into insulin-producing clusters. Stem Cells 22, 265-274 (2004)). However, these studies neither investigated endoderm marker expression nor demonstrated development of cells possessing stereotypical characteristics of β cells: simultaneous expression of C-peptide and PDX1, which is required for pancreas formation and co-activates the insulin promoter (Jonsson, J. et al., Insulin-promoter-factor 1 is required for pancreas development in mice. Nature 371, 606-609 (1994)). Because non-β cells such as neuronal cells, may express insulin (Sipione, S. et al., Insulin expressing cells from differentiated embryonic stem cells are not β cells. Diabetologia 47, 499-508 (2004)), and insulin present in the culture media may be taken up into other cell types under certain conditions in vitro (Rajagopal, J. et al., Insulin staining of ES cell progeny from insulin uptake. Science 299, 363 (2003)), it is important that the endoderm and pancreatic origin of insulin-staining cells derived from hESCs be ascertained.

Spontaneous differentiation of hESCs has produced PDX1$^+$/FOXA2$^+$ cells and co-transplantation of these differentiated cells with mouse dorsal pancreas (E13.5) produced PDX1$^+$/insulin$^+$ cells, and co-staining of insulin and C-peptide was observed (Brolen, G. K. et al., Signals from the embryonic mouse pancreas induce differentiation of human embryonic stem cells into insulin-producing β-cell-like cells. Diabetes 54, 2867-2874 (2005)). Thus, pancreatic lineage cells can be induced from spontaneously differentiating hESCs by signals emanating from the embryonic pancreas. However, the experimental methods used to reach such observations would be impractical to adopt into a high-throughput culture protocol. Moreover, the nature of the molecular signals was not revealed by the study. In addition, unselected stem cell populations are tumorigenic, meaning that they will generate non-malignant tumors, known as teratomas, in immunodeficient animals like undifferentiated ES cells do.

Several studies have evaluated the effects of growth factors on hESC differentiation to endoderm (Schuldiner, M. et al., Effects of eight growth factors on the differentiation of cells derived from human embryonic stem cells. Proc Natl Acad Sci USA 97, 11307-11312 (2000) and D'Amour, K. A. et al. Efficient differentiation of human embryonic stem cells to definitive endoderm. Nat. Biotechnol. 23, 1534-1541 (2005)). However, highly efficient differentiation to pancreatic precursors and islet cells has not been routinely achievable. Furthermore, insulin producing cells generated using previously reported methods are less responsive to glucose, in that, they appear less functionally mature than adult human β cells and are believed to possess a phenotype more like immature β cells. Taken together, these studies indicate that additional signals may be necessary to convert endoderm into pancreatic progenitors and insulin expressing cells into maturely functional β cells.

Studies of growth factor regulation of pancreas development in embryo models may provide important insights for directing hESC differentiation towards the pancreatic lineage (Wells, J. M. & Melton, D. A. Early mouse endoderm is patterned by soluble factors from adjacent germ layers. Development 127, 1563-1572 (2000)). For example, it was demonstrated in a chick-quail chimera system that BMP4 induces PDX1 expression in uncommitted endoderm and noggin blocks PDX1 expression in committed endoderm (Kumar, M. et al., Signals from lateral plate mesoderm instruct endoderm toward a pancreatic fate. Dev. Biol. 259, 109-122 (2003)). However, hESC differentiation is a multifactorial process, in which numerous factors influence the transition from pluripotency toward a differentiated cell lineage. Moreover, recent studies with hESCs have begun to focus on the differentiation of definitive endoderm as a first step toward development of pancreatic lineage cells. Others have reported on Activin A induction of definitive endoderm from hESCs (see D'Amour, K. A., et al. (2005)). However, pancreatic lineage cells were not induced by this protocol. Furthermore, preliminary results testing Activin A (at 5 ng/ml, 50 ng/ml, or 100 ng/ml) in serum-free media suggest that this treatment alone cannot induce pancreatic cell differentiation. This is not surprising given that it has been demonstrated that, in the absence of feeder cells, Activin A can maintain pluripotency of hESCs (Beattie, G. M. et al., Activin A maintains pluripotency of human embryonic stem cells in the absence of feeder layers. Stem Cells 23, 489-495 (2005)). Other hESC studies evaluating pancreatic differentiation have either been inconclusive as to the origin of insulin staining cells or required a period of in vivo growth in undefined conditions (Brolen, G. K. et al., (2005)).

Recent improved techniques reported for culturing hESCs into cells of the pancreatic lineage, such as that disclosed in U.S. Patent Application Publication No. 2011/0081720, illustrate the ability to produce pancreatic cell types for research and therapeutic uses. Thus, reproducible culture methods utilizing defined components that promote islet differentiation from human pluripotent stem cells have been shown. However, advances in our understanding of extrinsic signaling events controlling the formation of definitive endoderm and regional specification of the pancreas are leading to new methodologies for directed differentiation of stem cells into cells of the pancreatic lineage. Subtle differences in media growth factor concentrations, timing and/or sequence of growth factor introduction, and length of incubation with particular growth factors may induce pluripotent stem cells to differentiate into many different cell lineages. Moreover, the types and concentrations of supporting extracellular matrix components may further affect the differentiation of pluripotent stem cells. Therefore, how these influences are orchestrated will likely determine the fate of pluripotent stem cells cultured in vitro.

SUMMARY OF THE INVENTION

According to one embodiment, a method of culturing human pluripotent stem cells to produce cells of the pancreatic lineage includes the steps of (a) culturing the stem cells under conditions that induce formation of mesendoderm/primitive streak and definitive endoderm cells in a chemically defined medium comprising an effective amount of i) fibroblast growth factor, ii) Activin A, and iii) bone morphogenetic protein, (b) culturing the cells from step (a) in the presence of a chemically defined medium comprising an effective amount of insulin, transferrin, and selenium, wherein the medium further comprises a fibroblast growth factor in an amount that ranges from about 10 ng/ml to about 200 ng/ml, and (c) culturing the cells under conditions to produce foregut/pancreatic progenitor PDX1+ Ins− cells.

According to another embodiment, a method of culturing human pluripotent stem cells to produce cells of the pancreatic lineage includes the steps of (a) culturing the stem cells under conditions that induce formation of mesendoderm/primitive streak and definitive endoderm cells in a chemically defined medium comprising an effective amount of i) fibroblast growth factor, ii) Activin A, and iii) bone morphogenetic protein, (b) culturing the cells from step (a) under conditions favoring the formation of embryoid bodies, and (c) culturing the embryoid bodies under conditions favoring the formation of pancreas-spheres co-expressing PDX1, HNF1β, HNF6, and Sox9 proteins.

According to a further embodiment, a method of culturing pluripotent stem cells in a committed partially differentiated state includes the steps of (a) culturing the stem cells under conditions that induce formation of embryoid bodies containing multipotent progenitor cells, and (b) culturing the embryoid bodies on an extracellular matrix in cell culture inserts having a porous floor so as to maintain the multipotent progenitors cells in a non-terminally differentiated state.

According to a further embodiment, a method of producing progenitor cells of the pancreatic lineage includes the steps of (a) seeding human pluripotent stem cells in a cell culture vessel comprising an upper chamber and a lower chamber. A bottom surface of the upper chamber comprises a porous substrate. The method further includes (b) culturing the cells in a chemically defined medium comprising an effective amount of i) fibroblast growth factor, ii) Activin A, and iii) bone morphogenetic protein, and (c) obtaining pancreatic progenitor PDX1+ Ins− cells.

According to another embodiment, a pancreatic progenitor cell culture implant platform includes (a) a bicameral cell culture system with an upper chamber and a lower chamber separated by a porous substrate, and (b) stem cells cultured in the upper chamber on the porous substrate under conditions that induce commitment to pancreatic progenitor PDX1+ Ins− cells. The stems cells may be treated in a single step to differentiate into insulin producing cells of the pancreatic lineage and either removed from the platform for implantation into a subject or implanted into a subject along with the porous substrate.

BRIEF DESCRIPTION OF THE DRAWINGS

FIG. 20A (top path) is a schematic showing the transitions from Stage 2, where EBs are formed, to Stage 3, where they are plated on Matrigel™-coated coverslips, to Stage 4 (far right), where endocrine specification and differentiation occurs. FIG. 20A (bottom path) illustrates the "Alternate Protocol" Stage 3 previously discussed in reference to FIG. 1, where EBs are seeded on Matrigel™-coated cell culture inserts having a porous floor (for example, Transwell™ inserts), which leads to long-lived pancreatic/foregut progenitor cells. The culture medium and treatment with Matrigel™ is identical for both standard and alternate conditions. FIG. 20B depicts a larger side view of a porous cell culture insert in a cell culture well. When placed in a cell culture well, a cell culture insert establishes a bicameral system with an upper chamber wherein seeded EBs/cells may adhere to a porous insert floor that allows medium to pass between the upper chamber and lower chamber but prohibits EB/cell passage between chambers. Such a system is useful for culturing EBs/cells at an air-fluid interface, where cells receive nutrients from the lower chamber only.

(FIG. 19, top left panel).

DETAILED DESCRIPTION OF THE INVENTION

Figure 1:
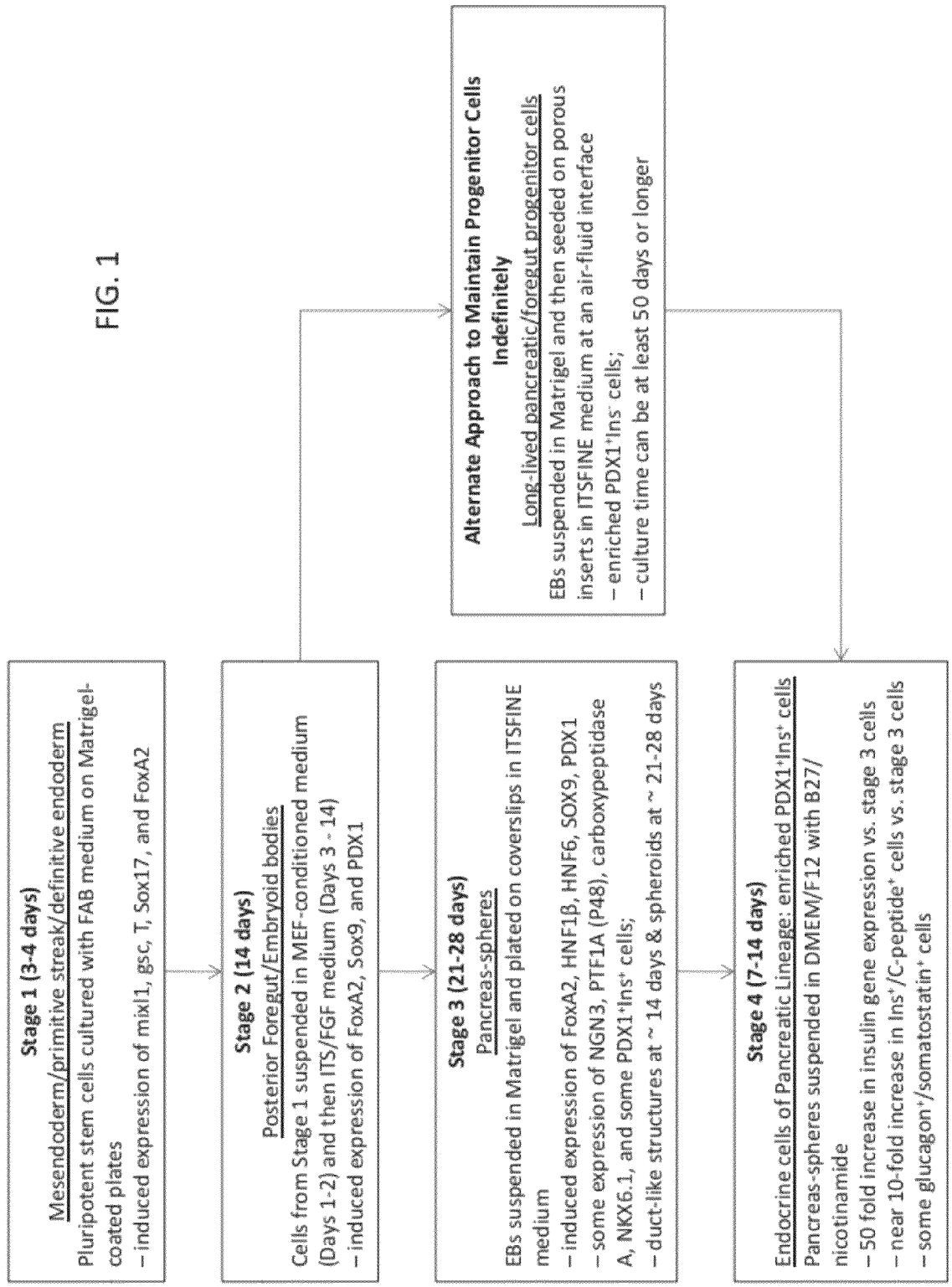
FIG. 1 is a flow chart depicting a method (Standard Protocol) of in vitro differentiation of pancreatic cell lineages from pluripotent stem cells. Stage 1 includes culturing pluripotent stem cells, such as hESCs and/or iPS cells, in a serum-free chemically defined medium (CDM: DMEM/F12 supplemented with 2% bovine serum albumin, 1 mM L-glutamine, 1% nonessential amino acids and 0.1 mM 2-mercaptoethanol) that includes fibroblast growth factor, Activin A, and bone morphogenetic protein (FAB medium). The cells are plated onto cell culture plates previously coated with Matrigel™ (BD Biosciences). After 3-4 days of culture, the cells exhibit upregulation of markers of mesendoderm formation (*T. brachyury*), primitive streak formation (mixl1 and gsc), and definitive endoderm characteristics, including expression of Sox17 and FoxA2. Stage 2 includes culturing the cells from Stage 1 in suspension in MEF (mouse embryonic fibroblast)-conditioned medium for 2 days followed by 12 days of culture in CDM supplemented with insulin, transferrin, selenium, and fibroblast growth factor (ITS/FGF medium). The cells form posterior foregut/embryoid body (EB) structures and exhibit widespread FoxA2 expression measureable by immunofluorescence, Sox9 expression, and the appearance of PDX1$^+$ cell clusters within the EBs. Stage 3 includes suspending the EBs from Stage 2 in Matrigel™ followed by plating on coverslips in CDM including insulin, transferrin, selenium, fibroblast growth factor 7, islet neogenesis associated peptide, and exendin 4 (a long-acting GLP-1 agonist) (ITSFINE medium). After approximately 14 days in the ITSFINE medium, duct-like structures appear, followed by pancreas sphere formation between 21 and 28 days culture in ITSFINE medium. The pancreas spheres exhibit widespread expression of FoxA2, HNF1β, HNF6, Sox9, and PDX1, and limited, but not easily detectable expression of NGN3, PTF1A (P48), carboxypeptidase A, and NKX6.1. Some PDX1$^+$Ins$^+$ cells may be observed within the pancreas spheres at this point. Stage 4 builds on Stages 1-3 by taking the pancreas spheres and further differentiating the cells therein by suspension culture in CDM with B27 and nicotinamide supplementation, which results in a 50-fold increase in insulin gene expression, as well as, nearly a 10-fold increase in the number of Ins$^+$/C-peptide$^+$ cells compared to cells in Stage 3. The Alternate Approach to Maintain Progenitor Cells Indefinitely (Alternate Protocol) is a variation of Stage 3, where in lieu of culturing the EBs on Matrigel™ coated coverslips, the EBs are seeded in Matrigel™ on porous cell culture inserts, such as Transwell™ cell culture inserts available from Corning. Here, the EBs are cultured in ITSFINE medium either submerged in medium or at an air-fluid interface, which results in a cell population enriched in PDX1$^+$Ins$^-$ cells that can be maintained for an extended period of time without apparent cell degradation or death until such time as it is desired to further differentiate the cells, for example, using a similar technique to that described in Stage 4. Each stage is represented with a period of days that indicates the length of time for the particular stage. The total time for differentiating pluripotent cells into pancreatic lineage cells (Stage 1 through Stage 4) may range from about 45 days to about 62 days. If the Alternate Protocol is chosen in lieu of Stage 3 of the Standard Protocol, the time for differentiating pluripotent cells into pancreatic lineage cells may be indefinite, as long-lived progenitor cells may be kept in culture in their non-terminally differentiated state until such time as they are needed, at which point, they may be directed to terminally differentiate.

The present invention relates broadly to novel methods for directed in vitro differentiation of pluripotent stem cells. For example, pluripotent stem cells may be directed to differentiate into cells of the pancreatic lineage (see FIGS. 1, 2, and 23). In this context, the methods involve culturing the stem cells in the presence of an effective amount of fibroblast growth factor, Activin A, and bone morphogenetic protein to induce differentiation in the direction of mesendoderm. These mostly primitive streak, mesendodermal, and definitive endodermal cells are further cultured to form embryoid bodies (EBs), which may be intact and enriched for definitive endoderm committed cells, which terminally differentiate to cells of the pancreatic lineage under defined conditions. By utilizing defined medium components that promote pancreatic cell differentiation, the described methods provide a simple, reproducible approach to enable large-scale production of pancreatic cell types for research, diagnostic, and/or therapeutic uses. Further, varied culture techniques at a particular differentiation stage have resulted in long-lived, partially differentiated progenitor cells that may be maintained indefinitely in such state until they are finally differentiated into cells of the pancreatic lineage. It is further contemplated that establishment of long-lived, partially differentiated cells may be possible for many lineages, such as, for example, the neural cell lineage, and therefore, such techniques are not believed to be limited to only cells of the pancreatic lineage. Moreover these methods may be employed to provide pancreatic progenitor cells for treating subjects in need thereof.

The present disclosure reports improvements over previous efforts to identify in vitro culture conditions that promote efficient derivation of β cells from hESCs. These previous efforts focused on FGF4, retinoic acid, FGF10, Activin A, cyclopamine, and BMP4 at different stages of hESC differentiation and settled on BMP4 treatment of hESCs grown on MEFs to provide the strongest enhancing effect on PDX1 expression. Herein, a cocktail of fibroblast growth factor, Activin A, and BMP4 in chemically defined medium is described that provides significant improvements over BMP4-only treatments in enhancing PDX1 expression in hESCs, as well as undifferentiated human induced pluripotent stem cells.

Differentiation Factors

Various growth factors and other chemical signals may initiate differentiation of hESCs or hiPSs into progeny cell cultures of one or more particular lineage. One of these differentiation factors is known as bone morphogenetic protein (BMP). BMPs are members of the transforming growth factor-β (TGFβ) superfamily of secreted signaling molecules, which play extensive pleiomorphic roles in almost all aspects of embryonic development. BMP4 and other BMP family members, such as BMP2, BMP5, and BMP7, bind BMP type II receptor BRII, which recruits type I receptor BR1A (ALK3) or BR1B. Upon ligand activation, the intracellular kinase domain of the type I receptors phosphorylates Smad1, -5, and -8, which are then escorted by a common Smad to enter the nucleus and activate target genes. The relative expression level of BMPs, receptors, and Smads within the cell is an important determinant of BMP-induced responses.

BMP4 is known to play an important role in fate determination and lineage development during embryogenesis. Several studies in other vertebrates have shown that BMP4 inhibits early neurogenesis in murine ESC cultures and promotes pancreatic endoderm specification from uncommitted endoderm (Kumar, et al., Signals from lateral plate mesoderm instruct endoderm toward a pancreatic fate. Dev. Biol. 259, 109-122 (2003) and Finley, et al., BMP-4 inhibits neural differentiation of murine embryonic stem cells. J. Neurobiol. 40, 271-287 (1999)). Based on these studies, applicants hypothesized that BMP4 might enhance endoderm and pancreatic differentiation from hESCs. However, an endoderm- and pancreas-promoting effect of BMP4 in hESC cultures was not necessarily expected because of the previously demonstrated mesoderm inducing attributes of BMP4 (Kattman et al. Stage specific optimization of Activin/nodal and BMP signaling promotes cardiac differentiation of mouse and human pluripotent stem cell lines. Cell Stem Cell 8, 228-40 (2011).

Fibroblast growth factor (FGF) also plays a role in mesoderm formation and is useful in the culture of stem cells with or without conditioned medium. In fact, it has been previously reported that bFGF is a useful additive in stem cell culture conditions in WO 01/66697. There are several different FGF subfamilies, the member ligands of which include FGF1-FGF23. Of the known FGF ligands, all show some degree of overlap of receptor binding, with the exception of FGF11-FGF14. (FGF Signaling in Vertebrate Development. Pownall M E, Isaacs H V. San Rafael (CA): Morgan & Claypool Life Sciences; 2010).

Figure 5:
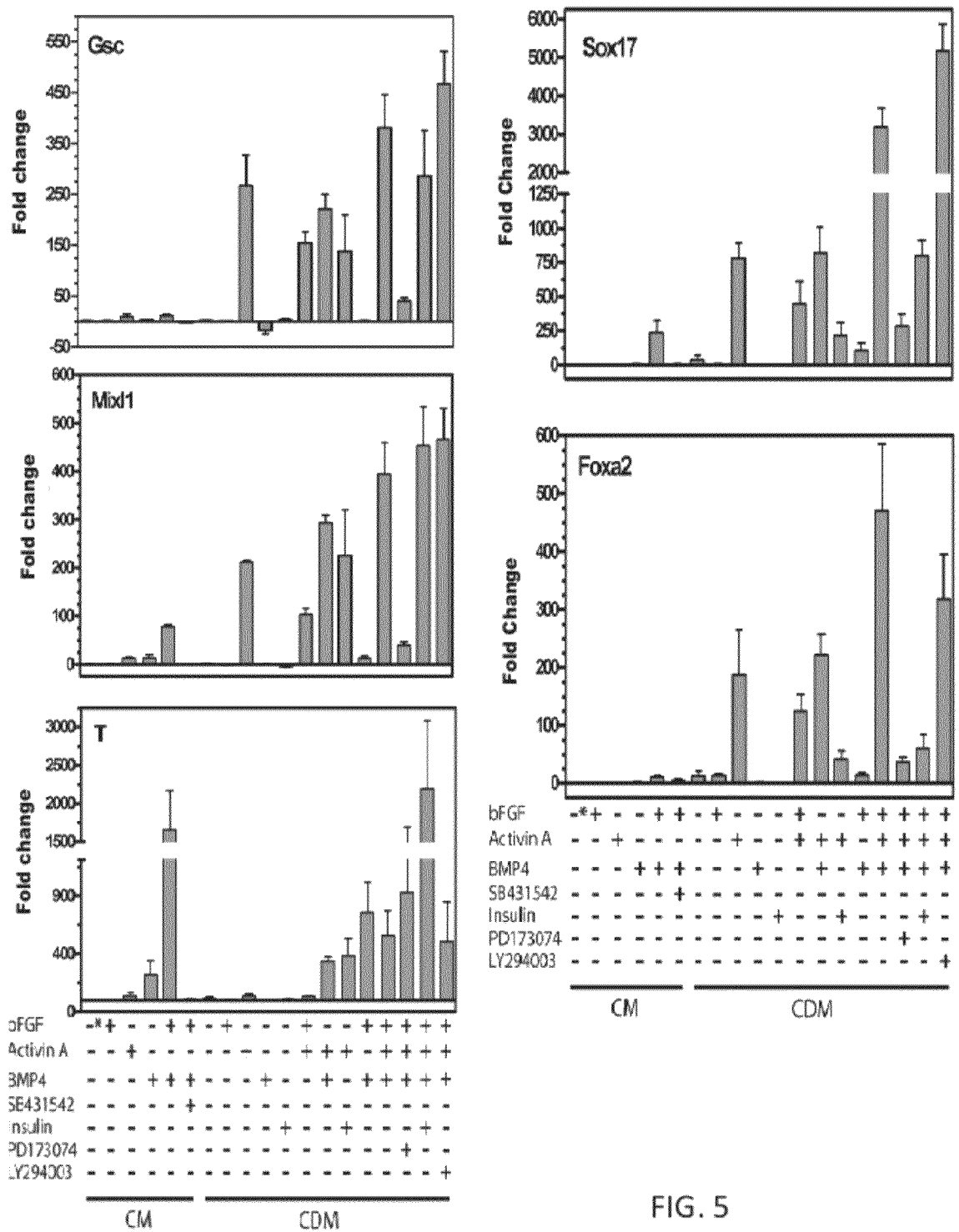
FIG. 5 illustrates the effect of different combinations of growth factors on endoderm, mesoderm, and primitive streak development. QPCR analysis was performed on cells after 4 days of differentiation with growth factors included as indicated. Data are shown as fold change versus undifferentiated hESCs grown with 4 ng/ml bFGF (*, far left condition). Other growth factor concentrations: bFGF, 100 ng/ml; Activin A, 100 ng/ml; BMP4, 50 ng/ml; Activin inhibitor SB431542, 10 μM; Insulin, 5 μg/ml; PD173074=FGF inhibitor; LY294003=phosphoinositide 3-kinase inhibitor. Error bars represent standard error; results are combined from 3-6 independent experiments. The expressions of each gene among different groups were compared using analysis of variance (ANOVA) with pairwise comparisons using Fisher's least significant difference tests. P-values are indicated in the text where relevant.

Activin is a member of the TGF-β superfamily and has various effects on diverse biological systems (Abe Y, et al. Activin receptor signaling. Growth Factors 2004 June; 22(2): 105-10). Activin A has been reported to have a role in the induction of definitive endoderm from hESCs (D'Amour, K. A., et al. (2005)). However, results testing Activin A (at 5 ng/ml, 50 ng/ml, or 100 ng/ml) in serum-free medium indicate that this treatment alone cannot induce pancreatic cell differentiation. In fact, our experiments (data not shown) revealed that stem cells treated with Activin A alone in chemically defined medium cannot survive suspension culture and form embryoid bodies. However, as shown in FIG. 5, Activin does play a central role in the induction of differentiation of hESCs by BMP4 and bFGF. Treatment of cells in CM alone versus CM with BMP4+bFGF versus CM with BMP4+bFGF+Activin antagonist SB431542 (available from Sigma) reveals induction of brachyury, Mixl1, and Sox17 in the presence of BMP4 and bFGF, but this response was negated by SB431542. A comparison of the effectiveness of BMP4, bFGF, and Activin A in promoting expression of these genes is also shown in FIG. 5. This is not surprising given that it has been demonstrated that, in the absence of feeder cells, Activin A can maintain pluripotency of hESCs (Beattie, G. M. et al., Activin A maintains pluripotency of human embryonic stem cells in the absence of feeder layers. Stem Cells 23, 489-495 (2005)). Nodal, another TGF-β superfamily member, binds the same Type I receptor as Activin A, and may provide an alternative to Activin A in the present disclosure.

Chemically Defined Media

A concern in the culture of human ES cells is to remove, to the extent possible, undefined constituents and constituents of animal origin from ES cell culture conditions. Standardizing culture conditions minimizes the normal variations in biological materials to which the cells are exposed. Further, by avoiding the use of materials, cells, exudates or constituents of animal origin, one can avoid possible cross-species viral transmission through the culture system. Thus, utilization of chemically defined media (CDM) that avoid the use of animal products provides a baseline culture condition upon which differentiation factors may be added with predictable effects.

CDM for hESCs may include a basal medium containing salts, vitamins, glucose and amino acids. The basal medium can be any of a number of commercially available media. For example, a combination of Dulbecco's Modified Eagle Medium and Hams F12 medium, sold as a combination (DMEM/F12; Invitrogen) may be utilized. To that combination may be added glutamine, β-mercaptoethanol, and nonessential amino acids. Other possible additives include antioxidants and lipids. A protein constituent of the medium is a serum substitute product. Albumin or purified albumin products, like the commercial product AlbuMax™ (Invitrogen) may be used. Alternatively or in addition, a defined protein product made up of albumin, insulin and transferrin may be used. Human proteins are preferred but not essential so long as uncharacterized animal products are excluded.

FAB medium includes FGF, Activin A, and BMP in DMEM/F12 supplemented with 2% BSA, 1 mM L-glutamine, 1% nonessential amino acids, and 0.1 mM 2-mercaptoethanol. Effective amounts of BMP, for example, BMP4, may range from about 10 ng/ml to about 100 ng/ml, or from about 10 ng/ml to about 50 ng/ml, or about 20 ng/ml to about 80 ng/ml, or about 15 ng/ml, or about 25 ng/ml, or about 50 ng/ml, or about 75 ng/ml, or about 100 ng/ml. Effective amounts of FGF, for example, bFGF, may range from about 10 ng/ml to about 200 ng/ml, or from about 10 ng/ml to about 100 ng/ml, or about 20 ng/ml to about 80 ng/ml, or about 15 ng/ml, or about 25 ng/ml, or about 50 ng/ml, or about 75 ng/ml, or about 100 ng/ml, or about 120 ng/ml, or about 140 ng/ml or about 160 ng/ml, or about 180 ng/ml or about 200 ng/ml. Further, effective amounts of Activin A may range from about 10 ng/ml to about 200 ng/ml, or from about 10 ng/ml to about 100 ng/ml, or about 20 ng/ml to about 80 ng/ml, or about 15 ng/ml, or about 25 ng/ml, or about 50 ng/ml, or about 75 ng/ml, or about 100 ng/ml, or about 120 ng/ml, or about 140 ng/ml or about 160 ng/ml, or about 180 ng/ml or about 200 ng/ml. In one embodiment, FAB medium contains 11 ng/ml bFGF, 100 ng Activin A, and 50 ng BMP4.

ITS medium may include about 5 µg/ml insulin, about 5 µg/ml transferrin, about 5 ng/ml selenous acid, and about 20 to about 100 ng/ml bFGF.

ITSFINE media may include about 5 µg/ml insulin, about 5 µg/ml transferrin, about 5 ng/ml selenous acid (selenium), about 10 ng/ml to about 100 ng/ml FGF7 (R&D), about 50 nM to about 500 nM INGAP (PSN-4765), about 10 mM nicotinamide (Sigma), about 1 nM to about 100 nM exendin-4 (Sigma), about 4 µg/ml to about 15 µg/ml insulin (Gibco), and about 2 g/L BSA (Sigma).

Extracellular Matrix Components

Growth-factor depleted Matrigel™ (BD) may be used in the present disclosure as one example of an extracellular matrix that may help cells form three dimensional structures to promote cell-cell contact and create a more islet-like environment. It is further contemplated that various other extracellular matrix components that form an extracellular matrix gel may be used, including combinations of extracellular matrix components, gelling agents, proteins, and optionally growth factors. For example, combinations of laminins (for example, laminin-111 and laminin-511), collagen IV, and entactin may be used. Further, extracellular matrices contemplated may include growth factors such as bFGF, epidermal growth factor, insulin-like growth factor 1, platelet derived growth factor, nerve growth factor, and TGF-β.

Differentiation Markers

By measuring expression of particular genes and proteins, progress of differentiation of pluripotent stem cells, such as hESCs and iPS cells, toward the pancreatic lineage may be detected and their progression monitored. For example, pancreatic duodenal homeobox 1 (PDX1) is a transcription factor specifying the pancreatic lineage. forkhead/winged helix transcription factor FoxA2 (formerly HNF-3β) is an upstream regulator of PDX1 and is a marker of definitive endoderm. The Sry/HMG box transcription factor Sox9 is expressed in the early pancreatic epithelium (uncommitted pancreatic progenitor cells). Earlier in differentiation, Sox17 is a marker of the definitive endoderm, but is not expressed later in differentiation. Sox17 is also expressed in primitive endoderm. Hepatocyte nuclear factor-1β (HNF-1β) appears to be a critical transcription factor in pancreatic development, and therefore is an early indicator of pancreas-specific differentiation. Transcription factor hepatocyte nuclear factor 6 (HNF6) regulates pancreatic endocrine cell differentiation and controls expression of the proendocrine gene neurogenin 3. Neurogenin 3 (ngn3) is an indicator of endocrine cell specification in the embryonic pancreas and induction of a neuroendocrine cell differentiation. Brachyury ("T") is a T-box transcription factor essential to the differentiation of the posterior mesoderm. When expressed earlier during development, T is considered a marker of mesendoderm, as $T^+$ cells are the common progenitors of both mesoderm and definitive endoderm. Goosecoid (gsc) and Mix1 homeobox-like 1 (Mixl1) are homeobox and homeobox-like proteins, respectively, that are expressed in the mesendoderm. NKX6.1 is a homeobox protein required for the development of 3 cells in the pancreas. Pancreas transcription factor 1 subunit alpha (PTF1A) is an indicator of pancreatic cell lineage commitment. Carboxypeptidase A is a pancreas-specific exopeptidase, and therefore an indicator of pancreas lineage differentiation. Ki67 is a nuclear protein that is associated with and may be necessary for cellular proliferation. Epithelial cell adhesion molecule (EpCAM) is a marker of fetal pancreas differentiation.

As used herein, mesendoderm cells were defined by the expression of Brachyury ("T"), expression of goosecoid (Gsc), Mixl1, and FoxA2, and Sox17. As used herein, embryoid bodies ("EBs") are three dimensional structures of groups of cells which interact in such a way to induce further differentiation of the cells within the EBs. EBs include definitive endoderm cells with duct-like structures, which include cells expressing FoxA2, Sox17, and PDX1. As used herein, pancreatic lineage cells include, for example, cells co-expressing PDX1 and NKX6.1, which are well known to represent either pancreatic epithelial progenitor cells or β cells. These cells are the only two cell types in the body expressing this combination of markers or PDX1, insulin, and C-peptide, which are well known to be simultaneously expressed in normal β cells; or cells expressing somatostatin generally understood to represent delta cells. Cells expressing Ki67 are proliferative.

Suitable terminally differentiated cells were characterized by the simultaneous expression of insulin, C-peptide and PDX1. Other cell types of the endocrine lineage, such as glucagon-expressing cells (for example, α-cells) and somatostatin-expressing delta cells also appeared in this context and in these regions of the cultures. A significant proportion of PDX1$^+$ terminally differentiated cells were found to co-express the cell surface marker epithelial cell adhesion molecule (EpCAM).

Table No. 1 defines terms, phrases, and abbreviations used throughout the specification.

TABLE NO. 1

Abbreviations.

| Abbreviation | Common Name |
|---|---|
| APS | Anterior primitive streak |
| bFGF | Basic fibroblast growth factor |
| BMP | Bone morphogenetic protein |
| BR | Bone morphogenetic protein receptor |
| CDM | Chemically defined medium |
| CM | Conditioned medium (Mouse embryonic fibroblast-conditioned media) |
| CMBF | Conditioned medium with BMP4 and bFGF |
| CPA1 | Carboxypeptidase A1, pancreatic |
| CT | Cycle threshold |
| CXCR4 | Chemokine (C—X—C motif) receptor 4 |
| DE | Definitive endoderm |
| DMEM/F12 | Dulbecco's modified eagle medium: nutrient mixture F-12 |
| DNMT3B | DNA methyltransferase 3b |
| EB | Embryoid body |
| EpCAM | Epithelial cell adhesion molecule |
| ES | Embryonic stem |
| ESC | Embryonic stem cell |
| Ex-4 | Exendin 4 |
| FAB medium | Medium containing fibroblast growth factor, Activin A, and bone morphogenetic protein |
| FOXA2 | Forkhead box protein A2 |
| GDF3 | Growth differentiation factor-3 |
| GLP-1 | Glucagon-like peptide-1 |
| Glut2 | Glucose transporter 2 |
| Gsc | Goosecoid |
| hCG | Human chorionic gonadotropin |
| hESC | Human embryonic stem cell |
| HNF1β | Hepatocyte nuclear factor 1beta |
| HNF6 | Hepatocyte nuclear factor 6 |
| hPSC | Human pluripotent stem cells |
| hTERT | Human telomerase reverse transcriptase |
| INGAP | Islet neogenesis associated peptide |
| iPS | Induced pluripotent stem cell |
| ITS/FGF medium | Medium containing insulin, transferrin, selenium and fibroblast growth factor |
| ITSFAB medium | Medium containing insulin, transferrin, selenium, fibroblast growth factor, Activin A, and bone morphogenetic protein |
| ITSFINE medium | Medium containing insulin, transferrin, selenium, fibroblast growth factor 7, islet neogenesis associated peptide, and exendin 4 (a long-acting GLP-1 agonist) |
| KDR | Kinase insert domain receptor |
| MEF | Mouse embryonic fibroblast |
| Meox1 | Mesenchyme homeobox 1 |
| MG | Matrigel ™ |
| Mixl1 | Mix1 homeobox-like 1 |
| Nanog | Nanog homeobox |
| NB media | Nicotinamide and B27 |
| NGN3 | Neurogenin-3 |
| Nic | Nicotinamide |
| Nkx2.5 | NK2 transcription factor related, locus 5 |
| NKX6.1 | NK6 homeobox 1 |
| Oct-4 | Octamer-binding transcription factor 4 |
| PDX1 | Pancreatic duodenal homeobox 1 |

TABLE NO. 1-continued

Abbreviations.

| Abbreviation | Common Name |
|---|---|
| PTF1A (P48) | Pancreas transcription factor 1 subunit alpha |
| REX1 | Reduced expression-1 |
| RPMI | Roswell Park Memorial Institute medium |
| Sox9 | SRY-box containing gene 9 |
| SR | Serum replacement |
| Sry/HMG | Sex determining region Y/high mobility group |
| SSEA-3 | Stage-specific embryonic antigen 3 |
| SSEA-4 | Stage-specific embryonic antigen 4 |
| T | Brachyury (T-box transcription factor) |
| Tbx6 | T-box 6 |
| TGF-β | Transforming growth factor beta |
| TITF1 | Thyroid transcription factor 1 |
| Tra 1-60 | Tumor-related antigen 1-60 |
| Tra 1-81 | Tumor-related antigen 1-81 |
| TWFAB | Simplified Protocol cells at Stage 1 seeded on Transwell ™ inserts |
| VEGF | Vascular endothelial growth factor |

The following examples are provided as further non-limiting illustrations of particular embodiments of the invention.

EXAMPLES

Example 1

Standard Protocol

The genes and intercellular signaling molecules controlling definitive endoderm and pancreas development in vertebrates are rapidly being elucidated. This knowledge has informed the establishment of methods for generating such cells from human ES and iPS cells in vitro. Based on the defined roles of nodal/Activin signaling in definitive endoderm development, we have identified a protocol using Activin A, BMP4, and bFGF in chemically defined, serum-free media which efficiently directs human pluripotent stem cells into an enriched population of definitive endoderm that can be differentiated in EB suspension cultures to produce a homogeneous population of foregut and pancreatic progenitors, including PDX1 and Sox9 expressing cells. Under defined conditions, a proportion of progenitors ultimately give rise to insulin$^+$/C-peptide$^+$/PDX1$^+$/β-like cells as well as cells expressing other endocrine hormones in vitro.

Materials and Methods

Culture of undifferentiated hESCs or human iPS (hiPS) cells. Cell lines used were NIH-approved H1 (WA01) and H9 (WA09) between passage 18 and 42, though hiPS cell lines derived from iPS (IMR-90)-4-MCB-1, iPS (Foreskin)-1-MCB-1, and DF 19-9-7T-MCB-01 may be used, as well as mouse ES cells.

Chemically defined medium comprised 80% DMEM/F12 and 20% Knockout serum replacement supplemented with 1 mM L-glutamine, 1% nonessential amino acids, 0.1 mM 2-mercaptoethanol and 4 ng/ml bFGF (all from Invitrogen). hESCs were cultured in 6-well plates on a feeder layer of irradiated MEFs, and the medium was refreshed daily. When the cells were nearly confluent, the ES cell colonies were split and passaged by detaching them from the feeder layer with 2 mg/ml dispase (Invitrogen). The colonies were then rinsed off the plates and filtered through a 70 μm cell strainer to remove MEFs. The colonies remained in the strainer. The retained cells were rinsed, pipetted into small pieces, and plated on growth factor-depleted Matrigel™ (BD Biosciences) at a density of 70% to 80% confluence in MEF-conditioned media.

Matrigel™-coated plates were generally prepared the day before splitting by thawing one aliquot of Matrigel™ (2 mg/tube) and diluting it with 6 ml cold DMEM/F12. One milliliter of diluted Matrigel™ was added to each well of a 6-well plate, which was incubated overnight at 4° C. On the day of splitting, the plate was allowed to sit at room temperature for 1 h before use.

Stage 1. On the day after splitting, differentiation was initiated by replacing the medium with medium containing 100 ng/ml bFGF, 100 ng/ml Activin A and 50 ng/ml BMP4 (FAB) in DMEM/F12 supplemented with 2% BSA, 1 mM L-glutamine, 1% nonessential amino acids and 0.1 mM 2-mercaptoethanol for 3 to 4 days. The medium was refreshed daily.

Stage 2. FAB-treated cells were detached from the plate with 2 mg/ml dispase and grown in suspension as cell aggregates in MEF-conditioned medium (CM) for 2 days. On the third day, the medium was switched to DMEM/F12 with ITS supplement (BD, 5 µg/ml insulin+5 µg/ml transferrin+5 ng/ml selenous acid) and 50 ng/ml bFGF for 12 days in suspension culture dishes. The medium was refreshed every 2 days.

Stage 3. Cell aggregates were transferred to a 15 ml centrifuge tube and allowed to settle by gravity. The medium was aspirated, and the pellet-containing tube placed on ice. Two milligrams of Matrigel™ were diluted with 3 ml of cold DMEM/F12 added to the pellet at a density of 50 to 100 cell aggregates/ml. One half milliliter of this diluted Matrigel™/cell aggregate mixture was added onto a coverslip previously loaded into wells of a 24-well plate and incubated overnight at 37° C. in 5% $CO_2$.

Nongelled Matrigel™ was aspirated from the wells and ITSFINE medium, a serum-free medium comprised of DMEM/F12 with ITS, 10 ng/ml FGF7 (R&D), 200 nM INGAP (PSN-4765, sequence: IGLHDPSHGTLPNGS), 10 mM nicotinamide (Sigma), 10 nM exendin-4 (Sigma), 4 µg/ml insulin (Gibco) and 2 g/L BSA (Sigma) was added for 21 to 28 days. The medium was refreshed every other day. As an alternative to DMEM/F12 only, DMEM/F12 may be used for the first 14 days of culture followed by 14 days of RPMI1640 as the base medium.

Stage 4. The sphere-structured cell masses were washed and the medium was replaced with RPMI1640 supplemented with 1×B27 (Invitrogen) and 10 mM nicotinamide for 1 to 2 weeks. Alternatively, the sphere-structured cell masses may be dislodged with 2 mg/ml dispase (two hundred microliters of per well of a 24-well plate), rinsed off the plate, and placed in suspension culture dishes in DMEM/F12 supplemented with 1×B27 and 10 mM nicotinamide for 1 to 2 weeks.

A fraction of each culture from stage 3 and 4 was used for RT-PCR and QPCR, and the remaining cells were either embedded in OCT (EB14; Tissue-Tek) or fixed on coverslips for immunostaining. Media were collected at the end of stage 3 and 4 for the measurement of C-peptide levels.

Quantitative PCR, RT-PCR, and C-Peptide Measurement.

Total cellular RNA was extracted with Trizol (Invitrogen). cDNA was synthesized from 1 µg total RNA using a SuperScript First-Strand Synthesis kit (Invitrogen). Quantitative real time RT-PCR (QPCR) was performed using Assays-on-demand agents (Applied Biosystems) on an ABI PRISM 7700 Sequence Detection System (Applied Biosystems) for the following transcripts: foxa2, sox17, brachyury, ngn3, pdx1, insulin, glucagon, glut2 and an endogenous control, β-actin (see Table No. 2 for assay numbers). QPCR was performed according to the equipment manufacturer's instructions. Relative quantification was carried out using the comparative cycle threshold (CT) method recommended by the supplier. Fold change was calculated as: $2^{-\Delta\Delta CT}$. Mean ΔΔCT values from QPCR analyses were compared using the unpaired, two-tailed Student's t-test. P values <0.05 were considered significant. Table No. 3 shows average cycle time numbers from many of the experiments described. hCG was measured on the Dade Behring Dimension Clinical Chemistry System, according to the instructions of the manufacturer.

TABLE NO. 2

Amplicon Sequences for Expression Assays.

| Gene name | Assay number (Applied Biosystems) |
|---|---|
| Foxa2 | Hs00232764_m1 |
| Sox17 | Hs00751752_s1 |
| Brachyury | Hs00610080_m1 |
| Pdx1 | Hs00426216_m1 |
| Insulin | Hs00356618_m1 |
| Cdx2 | Hs00230919_m1 |
| Tbx6 | Hs99365539_m1 |
| Meox1 | Hs00244943_m1 |
| KDR | Hs00176676_m1 |
| CXCR4 | Hs00607978_s1 |
| Sox9 | Hs00165814_m1 |
| HNF6 | Hs00413554_m1 |
| CPA1 | Hs00156992_m1 |
| Ngn3 | Hs00355773_m1 |
| Gsc | Hs00418279_m1 |
| Mixl1 | Hs00430824_g1 |
| Nkx2.5 | Hs00231763_m1 |
| TAT | Hs00356930_m1 |
| CDX1 | Hs00156451_m1 |
| TITF1 | Hs00163037_m1 |
| b-actin | Hs99999903_m1 |
| hCG | Hs00360700_g1 |

TABLE NO. 3

Average Cycle Time for Assayed Transcripts
Q-PCR CTs of pancreas-associated transcripts

| | hESC | hESC + BMP4 | EB14 | BMP4-treated, differentiated | | | human islet prep* |
|---|---|---|---|---|---|---|---|
| | | | | EB14 + 14 | EB14 + 21 | EB14 + 28 | |
| β-actin | 16.0 | 15.0 | 15.0 | 14.7 | 14.9 | 15.4 | 18.2 |
| Pdx1 | >50 | 36.4 | 26.7 | 23.9 | 24.3 | 23.0 | 26.7 |
| Insulin | >50 | >50 | 34.6 | 28.4 | 27.8 | 26.0 | 13.7 |
| Glucagon | >50 | >50 | 28.7 | 22.0 | 21.0 | 20.2 | 17.1 |
| Glut2 | >50 | 32.8 | 23.0 | 22.0 | 21.1 | 20.4 | 27.1 |
| Foxa2 | 29.9 | 25.6 | 24.0 | 23.1 | 23.0 | 22.7 | 22.0 |
| T | 34.0 | 25.6 | 25.4 | 27.9 | 28.4 | 28.5 | 39.3 |

*Approximately 50% pure

For non-quantitative RT-PCR, oligonucleotide primer pairs were generated against human transcripts using Genbank sequences. Primers were selected from two exons that spanned at least one intronic sequence. PCR was performed using HotStarTaq DNA polymerase (Qiagen) and reaction conditions were as follows: initial denaturation at 95° C. for 15 min, then cycles of 94° C. for 30 sec, 30 sec at annealing temperature, 1 min at 72° C., and a final 10 min extension at 72° C. Primers were annealed at 53° C. except for pdx1 (56° C.), sox/7 (55° C.) and foxa2 (50° C.; with Qiagen's Q-solution). A control sample without reverse transcriptase (-RT) was amplified with GAPDH primers in all cases, and human adult pancreas RNA was used as a positive control. C-peptide levels in media from stage 3 or 4 cultures were measured using the ultrasensitive C-peptide ELISA (Mercodia).

Immunofluorescence Staining.

Immunofluorescence staining of coverslips was carried out as previously described (Kahan et al., 2003). The following primary antibodies were used at the indicated concentrations: PDX1 rabbit anti-mouse serum 1:4000 (gift of C. Wright); insulin guinea pig anti-human 1:200 (Linco); glucagon mouse monoclonal 1:2000 (Sigma); somatostatin mouse monoclonal 1:2000 (Novo Nordisk); amylase rabbit 1:2000 (Accurate); Ki-67 mouse monoclonal 1:25 (BD Pharmingen); C-peptide rat monoclonal 1:3000 (BCBC 1921); Brachyury goat anti-human 1:20 (R&D); OCT4 mouse anti-human 1:100 (Santa Cruz); Sox17 goat anti-human 1:40 (R&D); Sox17 rat anti-human 1:400 (Gift of K. D'Amour); FOXA2 rabbit anti-rat1:4000 (Gift of R. Costa); HNF6 rabbit anti human 1:100 (Santa Cruz); HNF1β goat 1:100 (Santa Cruz); CPA1 rabbit anti-bovine 1:200 (AbD); ngn3 rabbit 1:2000 (Gift of M. German); Ptf1a rabbit 1:800; NKX6.1 mouse anti-rat 1:10 (Developmental Studies Hybridoma Bank); Sox9 rabbit 1:500 (Chemicon). Secondary antibodies (Goat anti-mouse IgG Alexa Fluor 488, 1:2000; Goat anti-rabbit Alexa Fluor 568, 1:4000; Goat anti-rat Alexa Fluor 488, 1:2000; Goat anti-rabbit, Alexa Fluor 647, 1:4000; Goat anti-mouse 568, 1:2000; Donkey anti-goat Alexa Fluor 568, 1:2000; Donkey anti-mouse Alexa Fluor 488, 1:2000) were obtained from Invitrogen/Molecular probes (Eugene, Oreg.).

Results

Cell differentiation was monitored at key time points: (1) after 3 days of FAB treatment (Stage 1); (2) after 14 days of suspension culture with bFGF+ITS following FAB treatment (Stage 2, EB formation); (3) 21 to 28 days after initiating EB adherent culture on coverslips in ITSFINE media (Stage 3); and (4) 1 to 2 weeks after cell aggregates were further grown in suspension culture (Stage 4). Gene and protein expression were assessed at the indicated time points, most commonly by quantitative RT-PCR and immunostaining.

Figure 3:
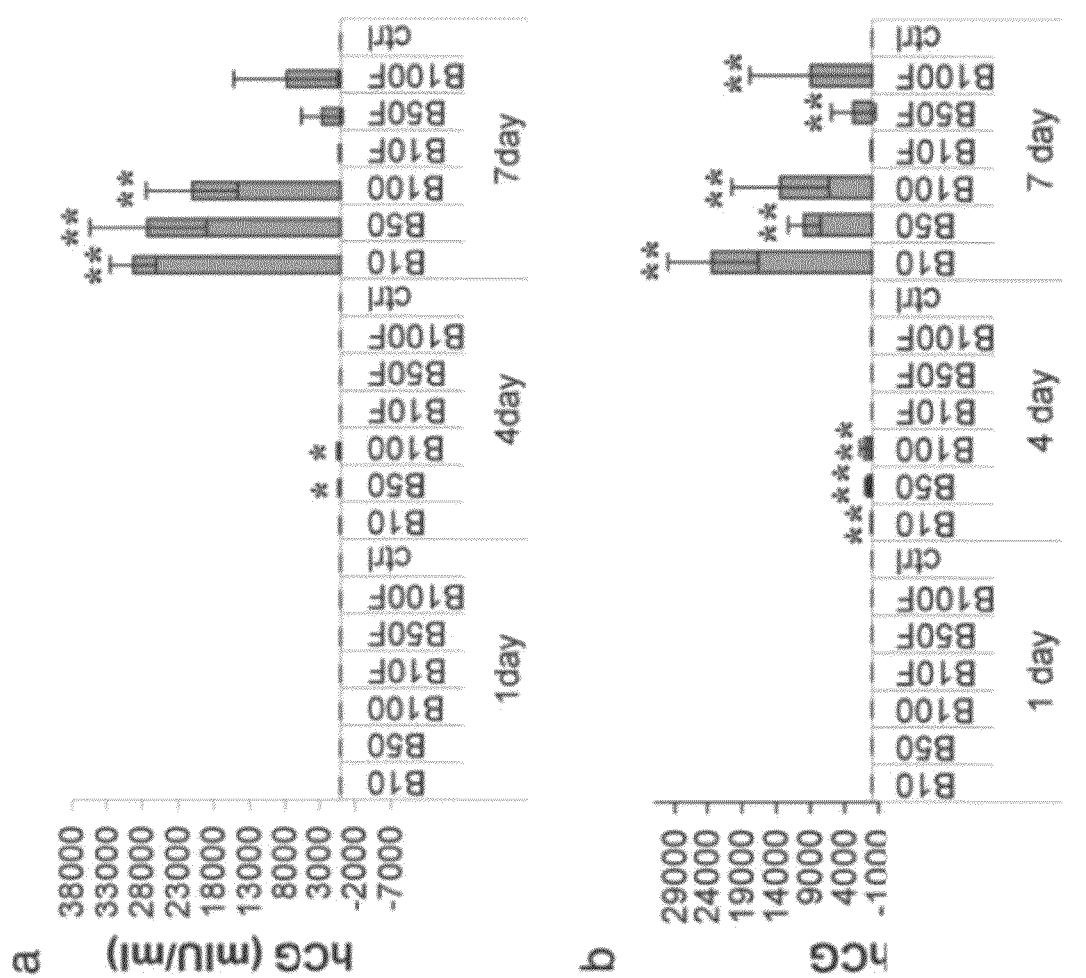
FIG. 3 illustrates how treatment of hESCs with BMP4 and/or bFGF influences cell fate. Cultures of adherent, undifferentiated hESCs grown in MEF-conditioned media were treated for 1, 4, or 7 days and then assayed for human chorionic gonadotropin (hCG) protein expression (a) or hCG transcript accumulation by QPCR (b). For QPCR results, the fold change values and statistical analyses were calculated by comparing treated cells with cells grown to the same time point but without added growth factors (ctrl). B10, 10 ng/ml BMP4; B50, 50 ng/ml BMP4; B100, 100 ng/ml BMP4; B10F, 10 ng/ml BMP4+100 ng/ml bFGF; B50F, 50 ng/ml BMP4+100 ng/ml bFGF; B100F, 100 ng/ml BMP4+100 ng/ml bFGF. *, $p<0.05$; **, $p<0.01$.

In Stage 1, cells were expected to differentiate towards mesendoderm/primitive streak and definitive endoderm fates. Compared to the undifferentiated state, FAB treatment induced significant upregulation of genes associated with primitive streak (mixl1, 363 fold; gsc, 335 fold), mesendoderm (T, 335 fold), and definitive endoderm (Sox17, 2485 fold; FoxA2, 471 fold) Immunostaining showed the intermingling of Brachyury (T)$^+$ cells with Sox17$^+$/FOXA2$^+$ costained cells. While treatment of hESCs with higher concentrations of BMP4 alone for 7 days yields a high proportion of trophoblast differentiation as manifested by human chorionic gonadotropin and CDX2 expression (FIGS. 3 and 4, respectively), treatment with a lower dose of 50 ng/ml BMP4 in combination with bFGF resulted instead in significant increases in anterior primitive streak (APS) and definitive endoderm (DE) gene expression, including GSC ($p=0.0002$), MIXL1 ($p<0.0001$), Brachyury (T) ($p<0.0001$), SOX17 ($p<0.0001$), and FOXA2 ($p=0.0005$), when compared with undifferentiated hESCs (FIG. 5). Presence of the trophectoderm marker CDX2 suggests that not all cells have adopted an anterior primitive streak fate.

Figure 6:
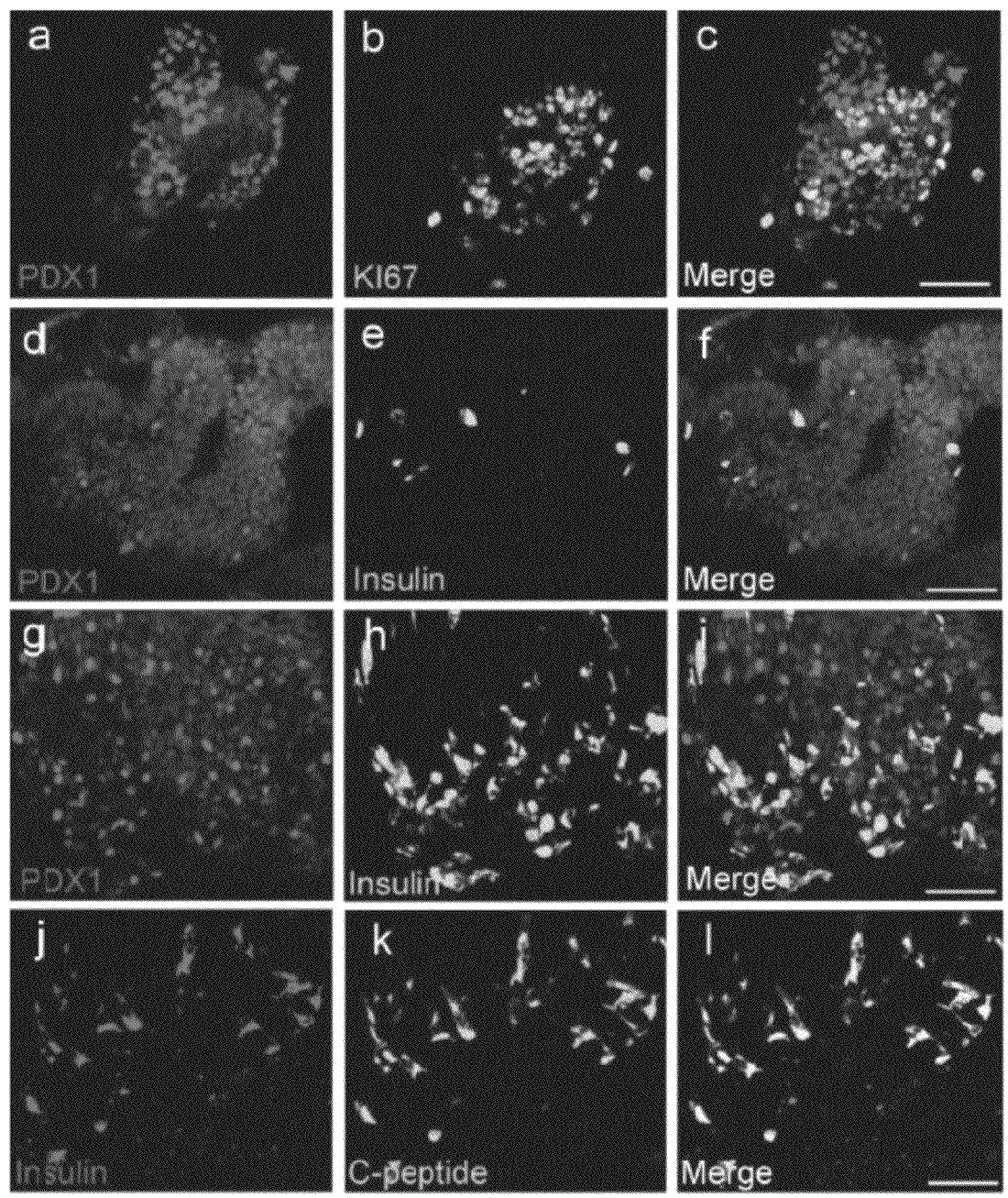
FIG. 6 shows that PDX1$^+$/Insulin$^+$ cells are present in cultures following BMP4/bFGF treatment of undifferentiated cells, a 14 day EB formation period, and further differentiation as plated EBs. (a-c) Most PDX1$^+$ cells no longer co-stain with Ki67 after plated EBs are grown in ITSFINE medium for 14 days (EB14+14). (d-f) Some PDX1$^+$ cells co-express Insulin at EB14+14. (g-i) Larger clusters of PDX1$^+$Insulin$^+$ co-staining cells appear at EB14+28. (j-l) Cells co-stain for Insulin and C-peptide at EB14+28. Scale bars 50 μm.
Figure 7:
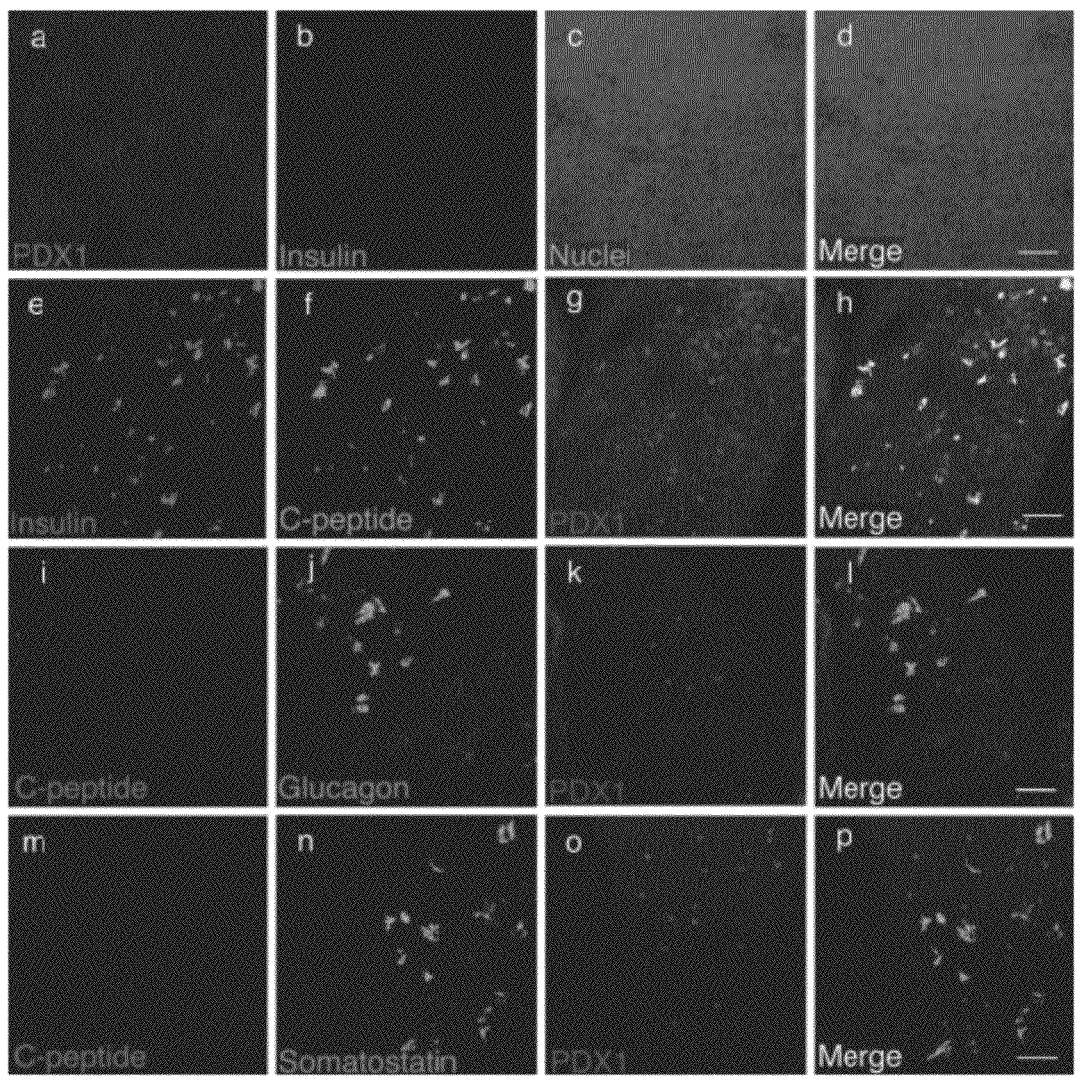
FIG. 7 shows that hormone-positive cells are present at EB14+28 in cultures previously treated with BMP4/bFGF. (a-d) No PDX1 or insulin staining is observed in cultures not treated with BMP4. (e-h) In treated cultures, cells co-express Insulin, C-peptide and PDX1. (i-l) Glucagon$^+$ cells do not co-stain for C-peptide or PDX1. (m-p) Somatostatin$^+$ cells do not co-express C-peptide, but some appear to co-stain for PDX1. Scale bars 50 μm.
Figure 8:
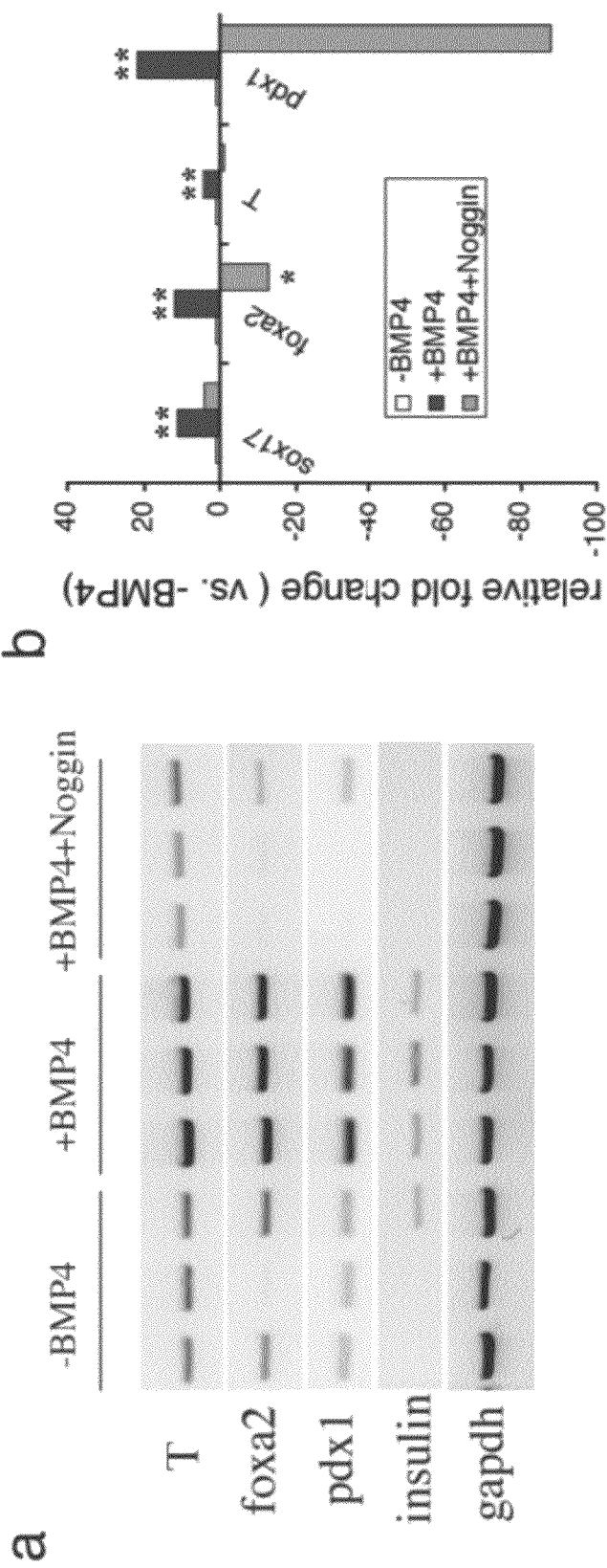
FIG. 8 shows the effects of BMP4 and bFGF treatment of hESCs on endoderm- and pancreas-associated gene expression. (a) RT-PCR and (b) QPCR analyses indicate that endoderm-(sox17, foxa2, pdx1) and pancreas-associated (pdx1, insulin) transcripts are increased in EBs made from hESCs grown on MEFs and treated with 50 ng/ml BMP4. The effect is eliminated when otherwise identical cultures are simultaneously incubated with 300 ng/ml noggin, a known BMP antagonist. EBs made from untreated hESCs demonstrate much less or no accumulation of the transcripts examined.

Further differentiation of BMP4/bFGF treated cells through Stage 2 and Stage 3 resulted in cultures containing cells positive for PDX1/Insulin/C-peptide (FIG. 6), as well as cells expressing somatostatin or glucagon (FIG. 7). Addition of the BMP4 antagonist noggin during Stage 1 led to significantly reduced levels of expression of SOX/7, FOXA2, Brachyury, and PDX1 at the end of Stage 2, suggesting that the observed differentiation requires BMP4 signaling (FIG. 8).

These observations suggested that BMP4 and bFGF were sufficient to induce DE from hESCs; however, the role of Activin A in this process was demonstrated by adding the Activin receptor inhibitor SB431542 to cells treated with bFGF+BMP4 in CM. This treatment completely inhibited expression of gsc ($p=0.4204$), Mixl1 ($p=0.89710$, Brachyury ($p=0.2113$), and FOXA2 ($p=0.1271$) (FIG. 5), which was not significantly different from that of undifferentiated hESCs. This finding indicates that differentiation to a mesendoderm fate occurs through the Activin pathway. Although no exogenous Activin A was added to our media, both CM and Matrigel contain Activin A/TGFβ activity (Vukicevic et al., 1992; Beattie et al., 2005). Indeed, when unconditioned media (UM) was substituted for CM, the induction effect of bFGF+BMP4 on SOX/7, FOXA2, and Brachyury was lost (data not shown).

Figure 9:
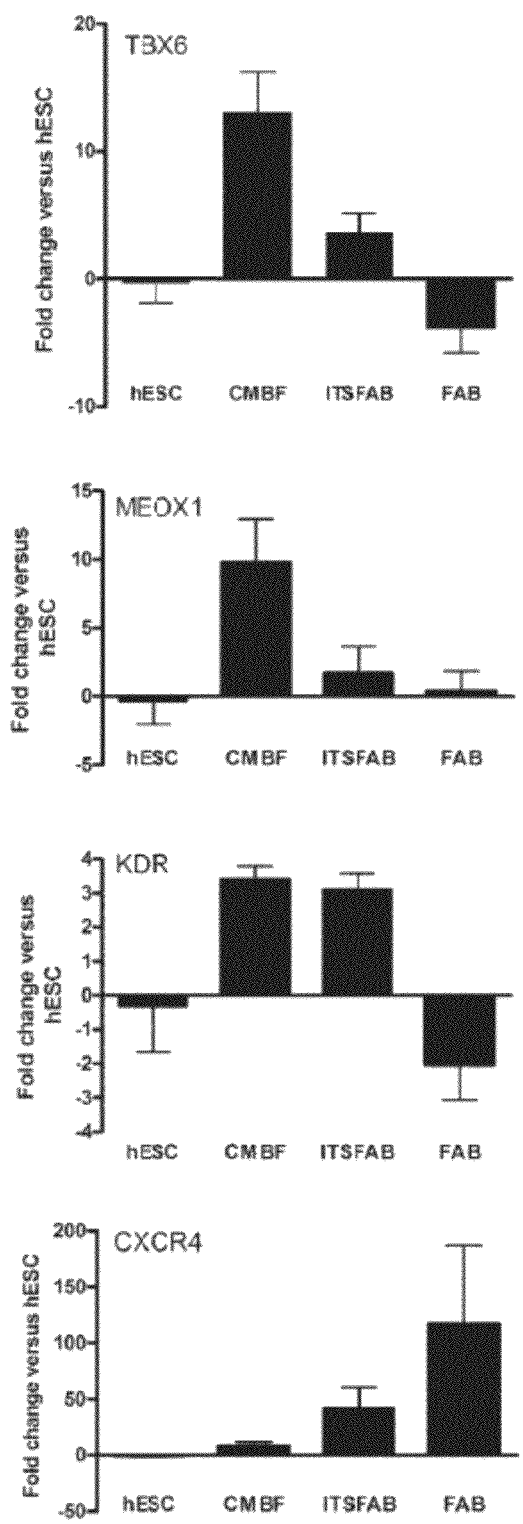
FIG. 9 reveals that the addition of insulin to Stage 1 cultures appears to increase differentiation of cells toward a mesoderm phenotype, while inhibiting DE differentiation. Fold change values of transcript accumulation are shown compared with undifferentiated hESCs. FAB-treated cells have lower expression of mesoderm genes tbx6, meox1, and kdr compared with cells grown in ITSFAB. Conversely, ITS-FAB treatment results in a lower expression of CXCR4, an identified definitive endoderm marker.

Unlike UM, CDM contains no serum or serum-replacement, both of which contain relatively high levels of insulin. Recent papers have shown that Activin A promotes DE differentiation from hESCs but that this occurs only when PI3K signaling pathway is inhibited (McLean et al., 2007). We found that adding Activin A to CM did not improve the differentiation of hESCs to mesendoderm, perhaps due to the presence of insulin, a PI3K agonist, which is a component of SR, contained in this medium. When Activin A is combined with insulin, the induction of SOX/7 is significantly decreased ($p=0.0154$) and at same time, induction of Brachyury is significantly increased ($p=0.0017$). It appears insulin promotes mesendoderm (T) and further mesoderm differentiation (MEOX1 and TBX6 and KDR) but inhibits DE differentiation (CXCR4; FIG. 9).

Figure 4:
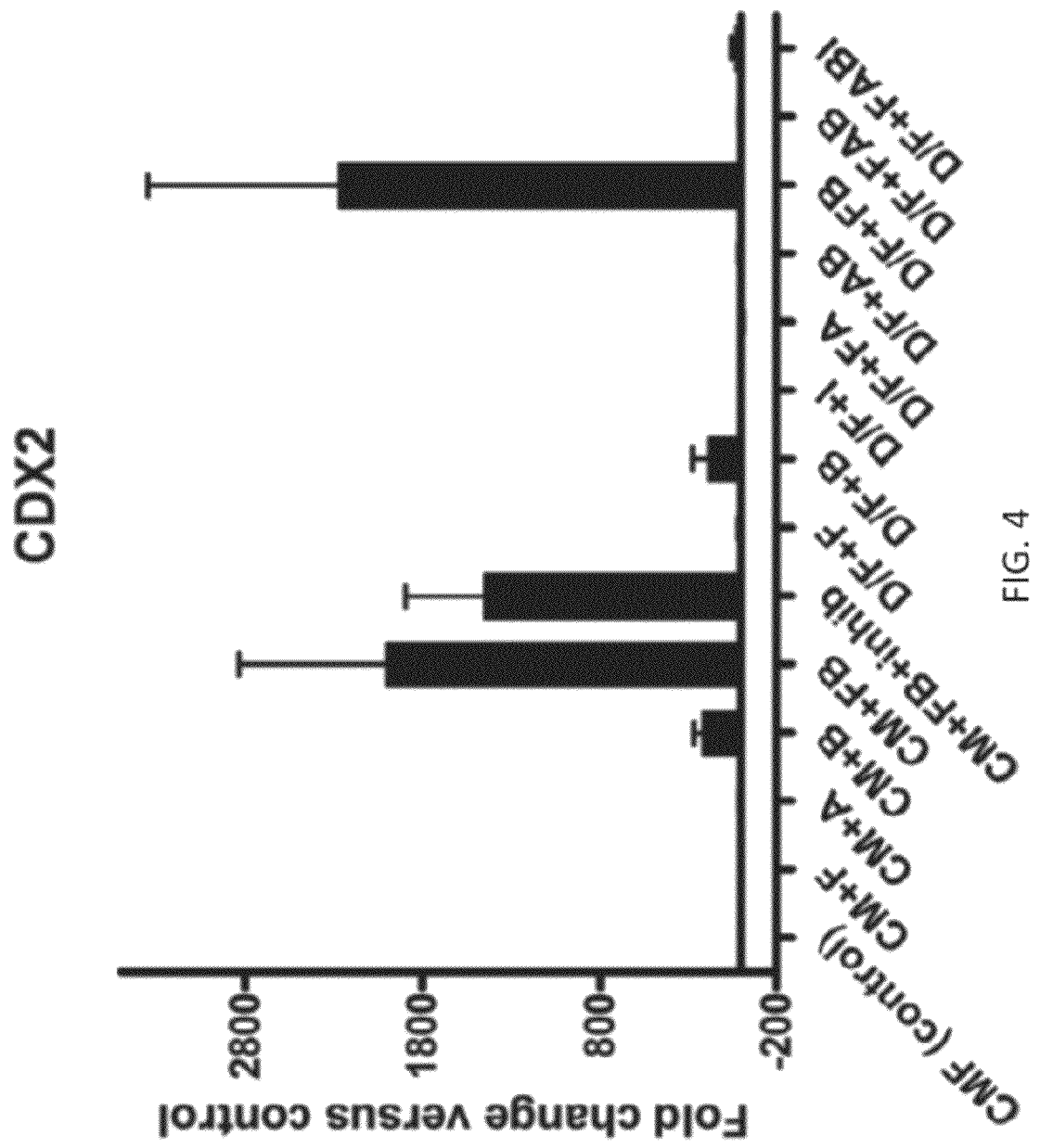
FIG. 4 illustrates the expression of cdx2 transcript at Stage 1. Fold change values compared to undifferentiated hESCs are shown. Treatment of cells with BMP4 alone results in an increase in cdx2 expression, suggesting that some cells have differentiated into trophectoderm. Addition of Activin A to these cultures essentially eliminates expression of cdx2, indicating that trophoblast differentiation is not occurring. CM, conditioned media; F, bFGF; A, Activin A; B, BMP4; inhib, SB431542 Activin signaling inhibitor; D/F, DMEM/F12; I, insulin. See Materials and Methods for growth factor concentrations.
Figure 10:
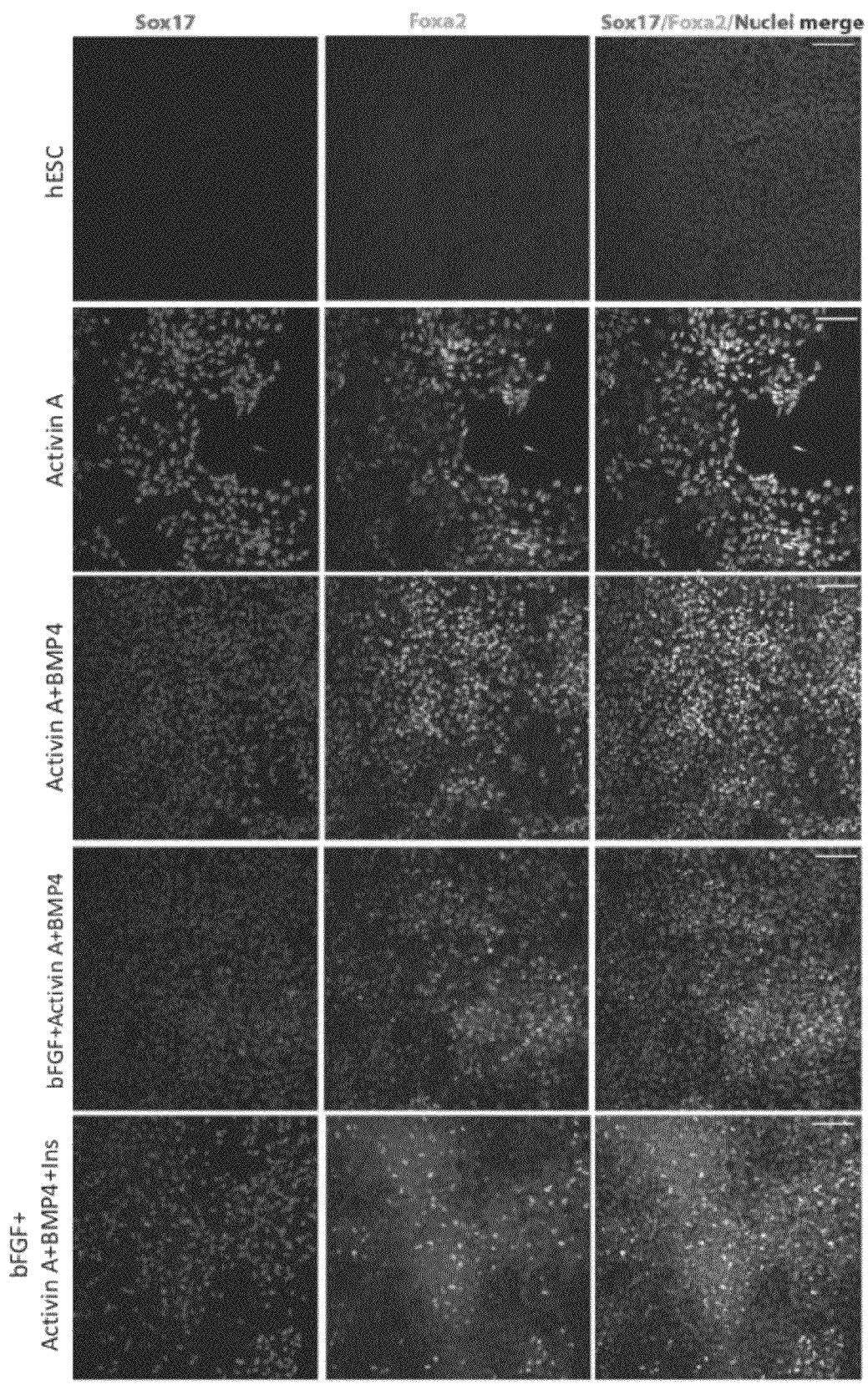
FIG. 10 depicts differentiation of hESCs to DE following growth factor treatment. Cells were differentiated for 4 days (Stage 1) and then stained for SOX17 (red) and FOXA2 (green). Topro3 (blue) marks nuclei. Growth factors as indicated are delivered in the following concentrations: bFGF, 100 ng/ml; Activin A, 100 ng/ml; BMP4, 50 ng/ml; insulin: 5 µg/ml. hESC=undifferentiated human ESCs grown in CM. Addition of insulin to FAB treatment results in lower levels of co-expression of FoxA2 and Sox17, representing DE, compared with FAB treatment. Scale bars 50 µm.
Figure 11:
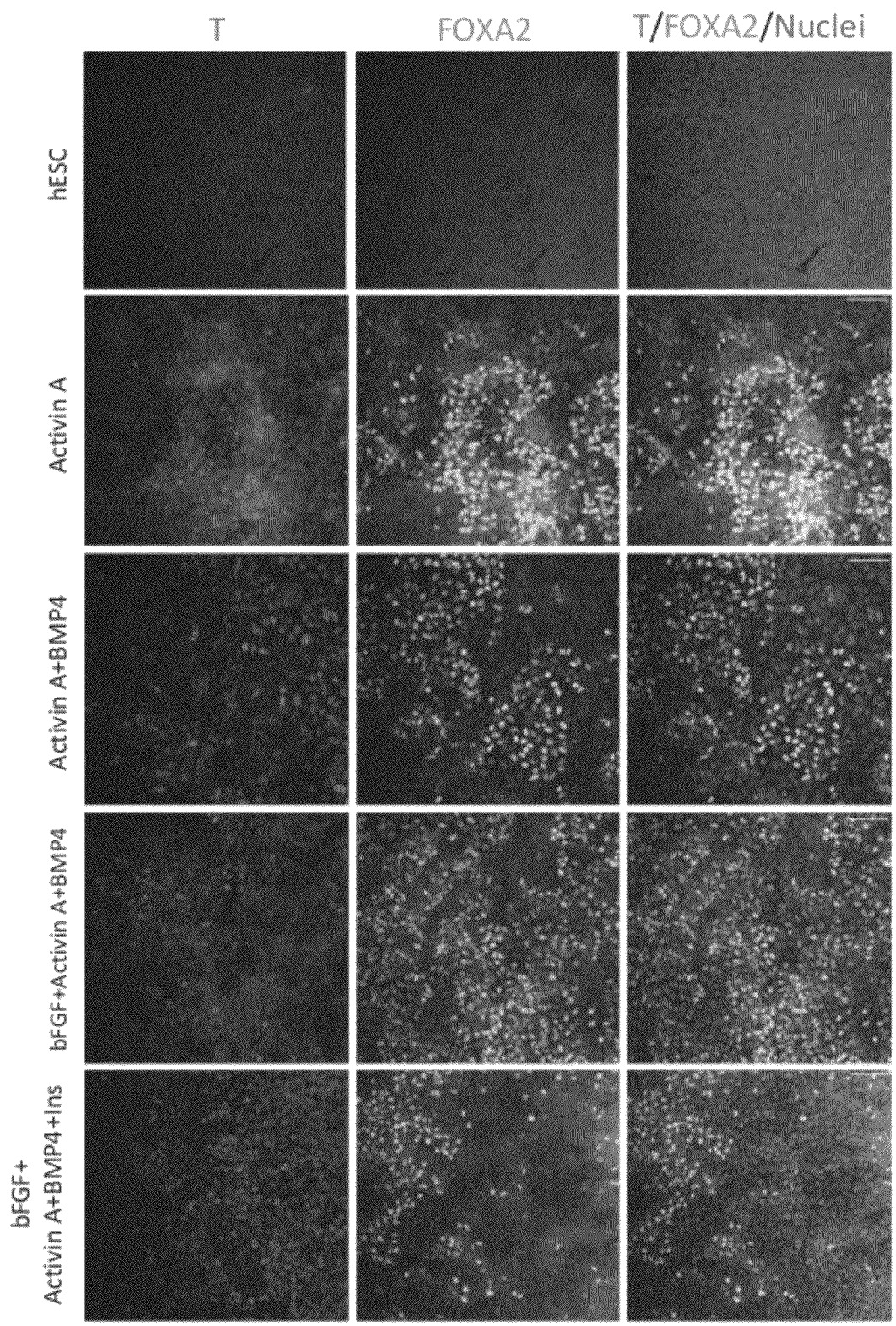
FIG. 11 depicts differentiation of hESCs following growth factor treatment as in FIG. 10 for 4 days (Stage 1) and then stained for Brachyury (T, red) and FOXA2 (green). Topro3 (blue) marks nuclei. Growth factor concentrations: bFGF, 100 ng/ml; Activin A, 100 ng/ml; BMP4, 50 ng/ml; insulin: 5 µg/ml. hESC=undifferentiated human ESCs grown in CM. Insulin and FAB treatment yields a reduced proportion of FoxA2$^+$ cells and a greater percentage of T$^+$ cells compared to FAB treatment alone. Scale bars 50 µm.

To determine whether treatment with Activin A alone is sufficient to promote differentiation from anterior primitive streak through pancreatic endoderm to pancreatic endocrine cells in our protocol, a chemically-defined serum free medium (CDM) was developed. Cells grown in CDM supplemented with Activin A alone showed significant induction of MIXL1, GSC, T, SOX17 and FOXA2 ($p<0.0001$ compared to undifferentiated cells in CM; FIG. 5). Despite this promising early differentiation, EBs formed from Activin A-treated hESCs failed to develop. Thus, it was impossible to assess these cells in later stages of differentiation. We next tried treating cells with bFGF+BMP4 in CDM, and found good expression of SOX17 and T, although levels of MIXL1, GSC, and FOXA2 expression were much lower than in cultures treated with Activin A (FIG. 5). However, when the three growth factors were combined bFGF+Activin A+BMP4 (FAB), expression levels of all five transcripts were comparable to or greater than those seen with Activin A alone (FIG. 5) Immunostaining confirms the expression of FOXA2, SOX17, and T at the protein level (FIGS. 10 and 11) following this treatment. Activin A also inhibits the ability of BMP4 to induce differentiation of hESCs to trophoblasts. CDX2, an early marker of trophoblast differentiation induced by treatment with bFGF+BMP4, is not expressed when cultures are grown in FAB (FIG. 4). Furthermore, EBs can be readily generated from FAB-treated human ES cells, enabling further differentiation to pancreatic endoderm and endocrine cells. We therefore used FAB treatment in CDM for Stage 1 differentiation of hESCs to DE to test further differentiation strategies to pancreatic lineages.

Figure 12:
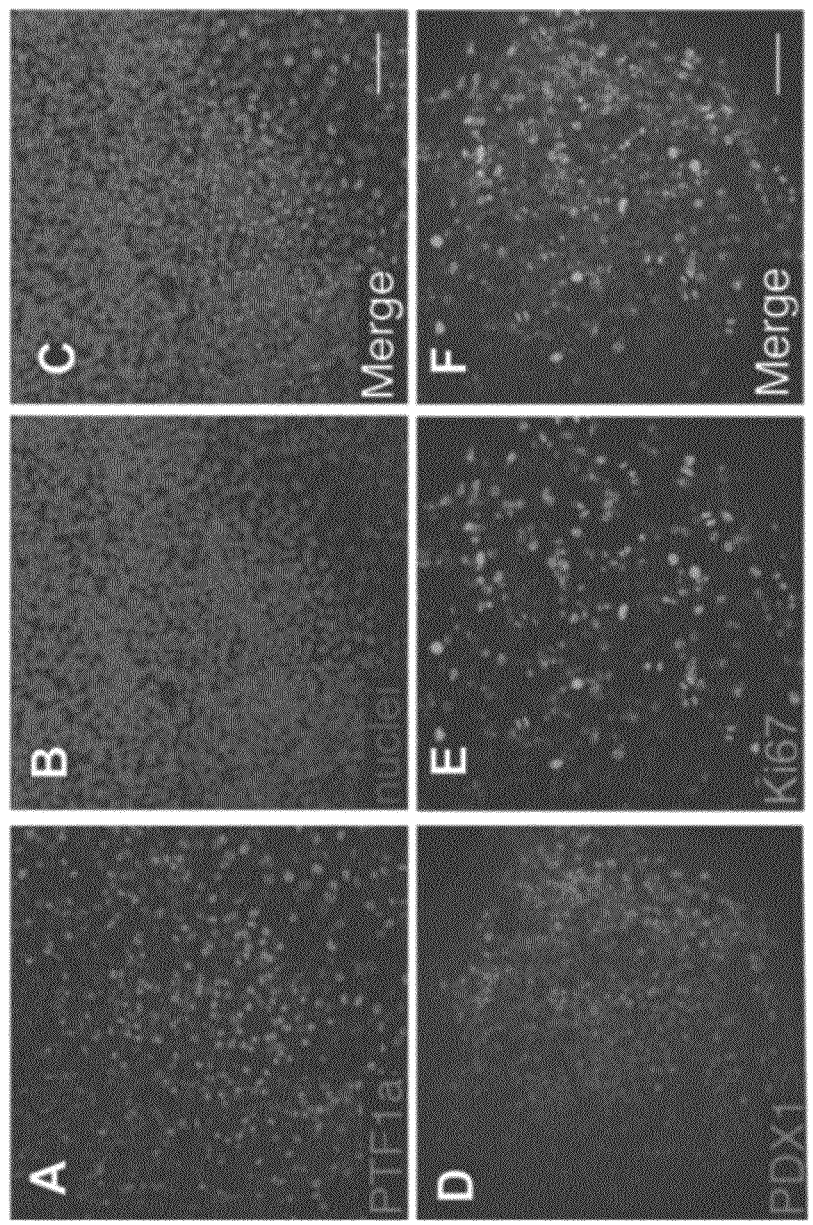
FIG. 12 shows a suspension culture (Stage 2) of BMP4/bFGF-treated hESCs with bFGF promotes endoderm and pancreas lineage cell differentiation. EB14s made from BMP4/bFGF-treated ESCs and grown with bFGF supplementation during the EB stage were plated in serum-free ITSFINE medium for 14 days, then plated, fixed, and stained. A large percentage of the cells express PTF1a (a-c). A majority of cells are PDX1$^+$, and many of these cells remain proliferative and express Ki67 (d-f). Scale bars 50 µm.

Previous experiments have shown that differentiation through an EB stage, in which inductive tissue interactions may occur in three dimensions among the early embryonic germ layers, positively influences development of pancreatic lineage cells, compared to differentiation under two-dimensional conditions (Xu et al., 2006). Different combinations of growth factors were tried at different stages to get maximum expression of PDX1 and Insulin. Cells differentiated following an initial protocol of treatment with BMP4+bFGF in CM in Stage 1 followed by growth as EBs in CM+bFGF (bFGF concentrations ranging from 20 ng/ml to 100 ng/ml) during Stage 2 resulted in a maximum level of PDX1 transcript accumulation at EB14 (14 days of suspension culture). In these cultures, the delta Ct of PDX1 was between 5 and 6, comparable to the level of PDX1 expression in a 50% pure adult human islet preparation. Immunostaining showed a greatly increased number of PDX1$^+$ cells, and some of these cells also expressed Ki67, suggesting PDX1$^+$ cells are proliferative at this stage (FIG. 12). In addition, many cells in these cultures expressed PTF1a. However, this extremely strong expression of PDX1, even in conjunction with expression of PTF1a, did not lead to robust Insulin expression at later stages (data not shown).

Figure 13:
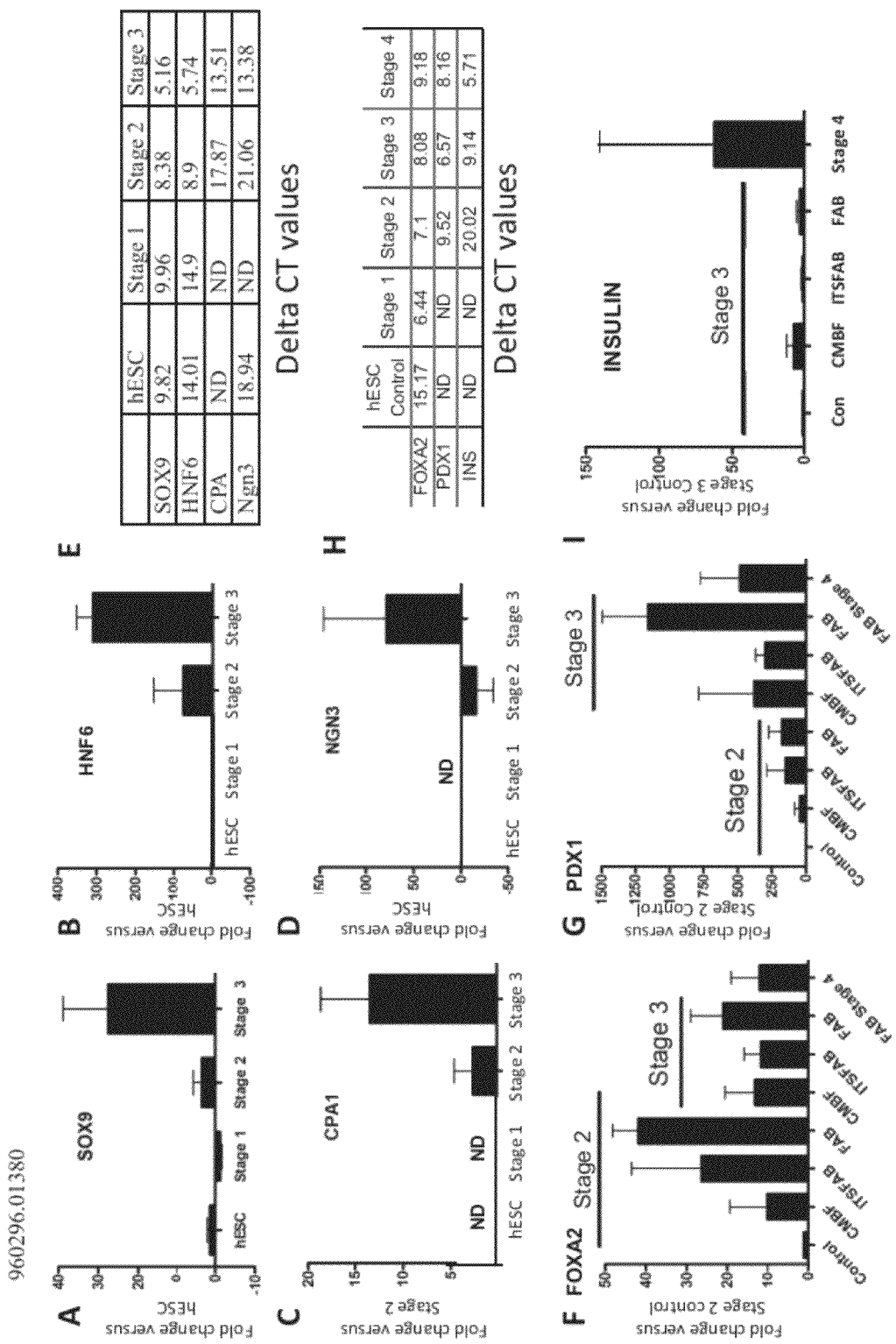
FIG. 13 depicts a time-course transcript accumulation of sox9, hnf6, cpa1, ngn3, foxa2, pdx1 and insulin by QPCR. (a-d) Fold change in transcript accumulation for FAB-treated cells versus hESCs (a, b, d) or Stage 2 FAB-treated cells (c) during Stages 1-3 of the protocol for Sox9, HNF6, CPA1, and NGN3. (e) Average delta Ct values are shown for the same transcripts and stages shown in a-d. (f, g) Fold change values of foxa2 (f) and pdx1 (g) transcripts at Stage 2 and 3 for cells treated at Stage 1 with either CMBF, ITSFAB or FAB compared to spontaneously-differentiated control cells at stage 2. Cells treated at Stage 1 with FAB yield higher levels of Foxa2 and PDX1 expression at Stage 2 and 3 compared to CMBF- and ITSFAB-treated cells. (h) Fold change values of insulin transcripts at Stage 3 for cells treated initially treated in Stage 1 with either CMBF, ITSFAB or FAB versus spontaneously differentiated control cells at stage 3. Fold change of Stage 4 cells treated at stage 1 with FAB versus Stage 3 spontaneously differentiated cells is also shown. (i) Average delta Ct values for Foxa2, Pdx1, and insulin in FAB treated cells at Stages 1-4 are listed. CMBF: hESCs at stage 1 treated with conditioned media with BMP4+bFGF; ITSFAB: hESCs at stage 1 treated with ITS+bFGF+Activin A+BMP4; FAB: hESCs at stage 1 are treated with bFGF+Activin A+BMP4. ND: Not detected.
Figure 14:
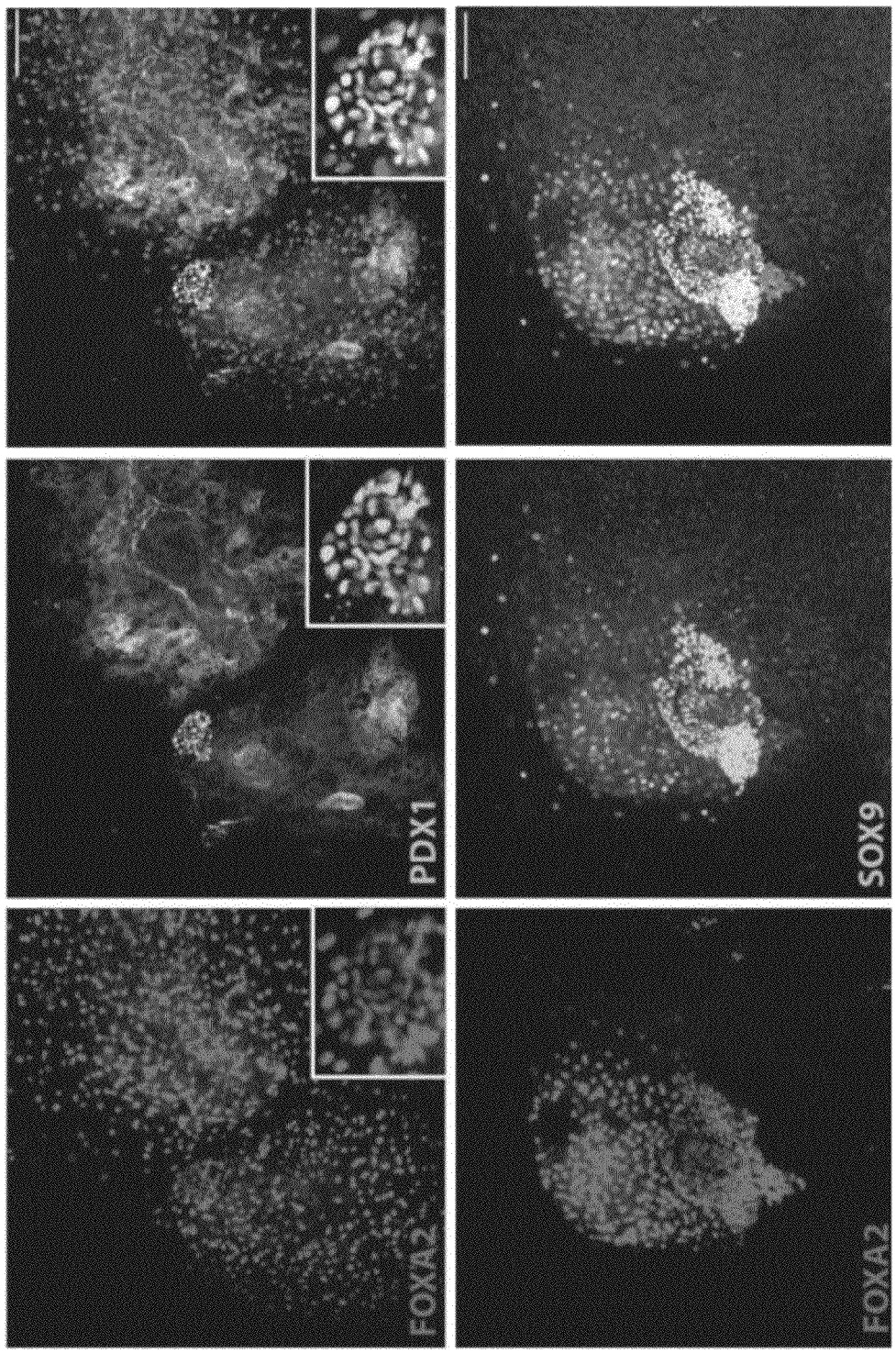
FIG. 14 reveals the expression of FOXA2, PDX1, and SOX9 at the end of Stage 2. Stage 2 EBs were plated overnight and then stained for FOXA2 (red) and PDX1 or SOX9 (green). Nuclei are marked with Topro3 (blue). Small focal areas of cells stain for PDX1 or SOX9; the majority of these cells also express FOXA2. Scale bars 50 µm.

On the other hand, cells treated with FAB in Stage 1 and then grown with ITS+bFGF in suspension culture during Stage 2 have a relatively later peak of PDX1$^+$ expression and display strong Insulin expression at later times. At the end of Stage 2, QPCR showed a significant increase in PDX1 transcripts in EBs made from FAB-treated cells compared to EBs grown from untreated hESCs (fold change of 175, FIG. 13, panel G), with a delta Ct value of 8-10 (FIG. 13, panel H). Transcript expression levels of FOXA2 were increased by 40-fold in FAB-treated cultures versus untreated controls. The increased expression of SOX9, HNF6, CPA1, and NGN3 in FAB-treated cells (FIG. 13, panel E) suggest that cells have differentiated into foregut progenitor cells, which is supported further by immunostaining. At the end of Stage 2, FAB-treated hESCs express FOXA2, SOX9 and PDX1 (FIG. 14). FOXA2 appeared widely distributed, and some cells also expressed SOX9. PDX1$^+$ cells appeared in small clusters among FOXA2$^+$ cells. Thus, there is a transition from endoderm-committed cells to pancreatic progenitors from Stage 1 to the end of Stage 2 during suspension culture.

Figure 15:
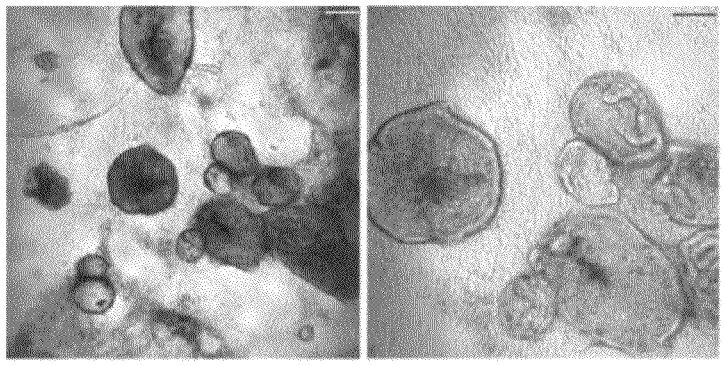
FIG. 15 reveals the expression of endoderm and pancreatic markers in Stage 3 cells. Top, bright field image of Stage 3 cells; panels are the same field at different magnifications. Scale bars 50 µm.

To further investigate the differentiation potential of cells grown through Stages 1 and 2, Stage 2 cells were plated in Matrigel (MG) on coverslips in serum-free ITSFINE medium containing insulin, transferrin, selenium, FGF7, INGAP, nicotinamide, and exendin-4 for an additional 21-28 days (Stage 3). By 2 weeks into Stage 3, duct-like structures began to appear, gradually becoming larger and forming into spheroids (pancreas spheres/cell-clusters). These spheroids became more numerous and eventually were found in all areas of the cultures by the end of this stage (see FIG. 15).

Figure 16:
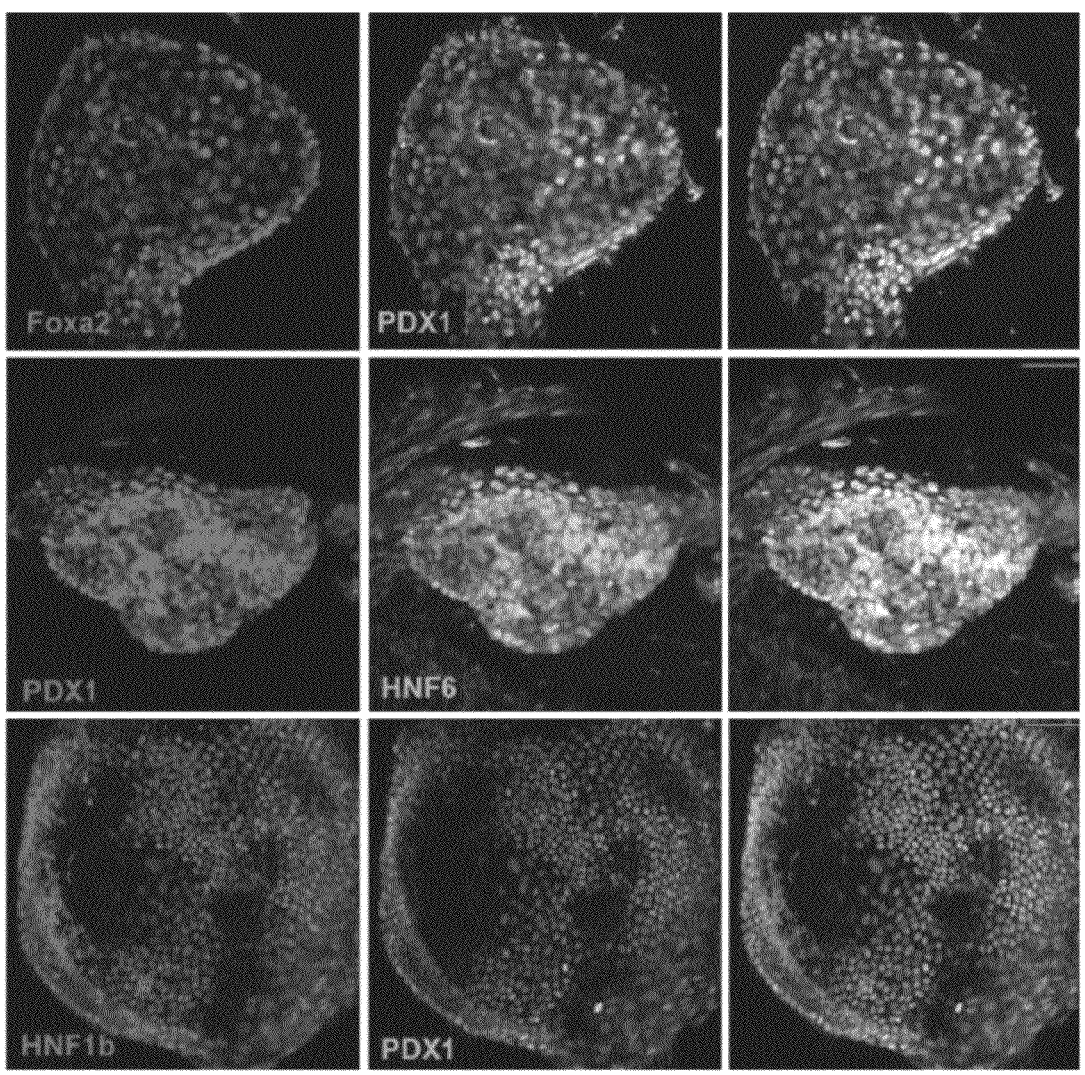
FIG. 16 reveals the expression of endoderm and pancreatic markers in Stage 3 cells. Cells were stained for FOXA2, PDX1, HNF6, and HNF1beta, as shown. Topro 3 (blue) marks nuclei. Scale bars 50 µm.
Figure 17:
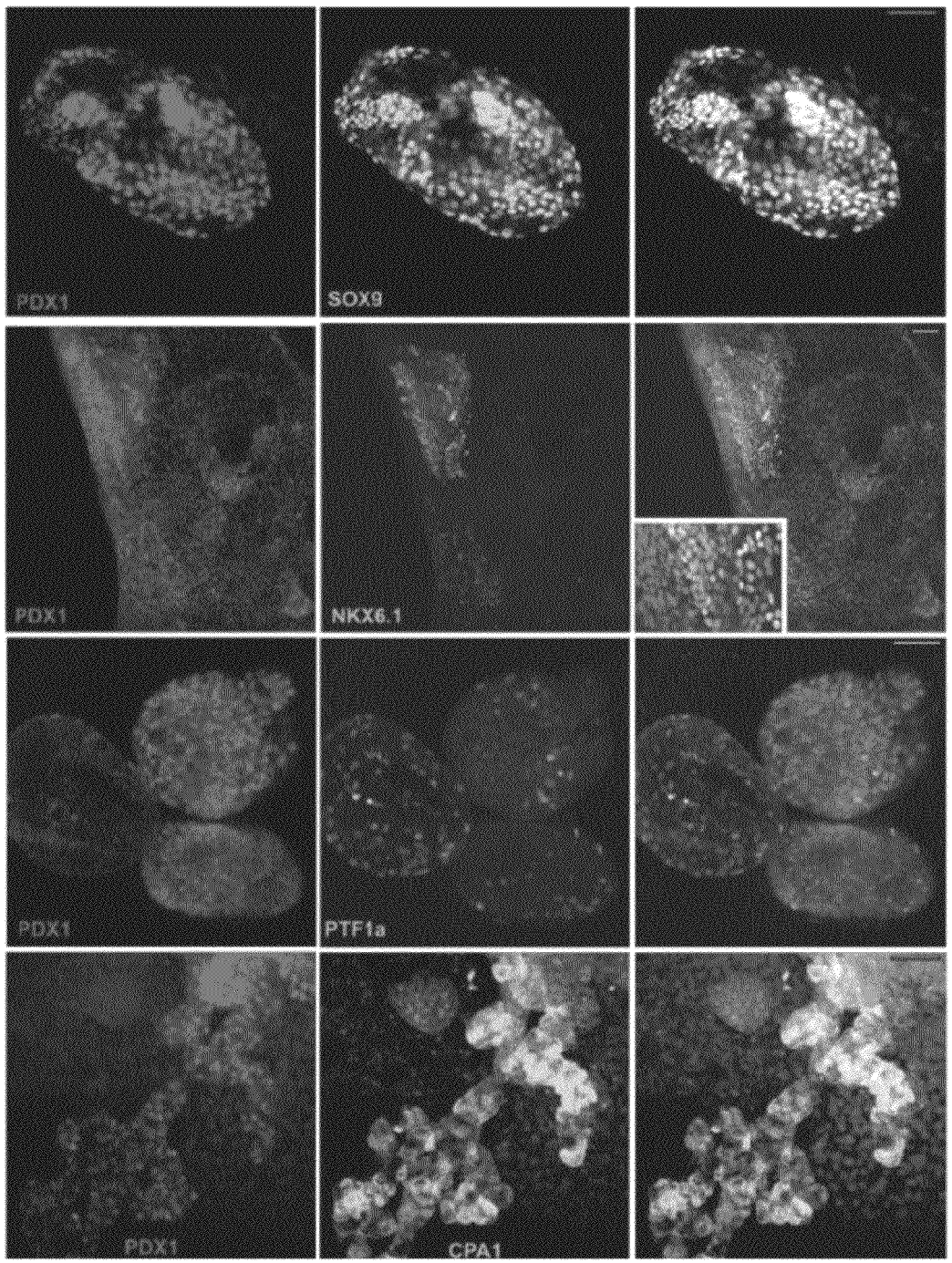
FIG. 17 reveals the expression of pancreatic markers in Stage 3 cells. Cells were stained for PDX1, SOX9, NKX6.1, PTF1a, and carboxypeptidase A1 (CPA1). Nuclei (blue) were marked by Topro 3. Scale bars 50 µm.
Figure 18:
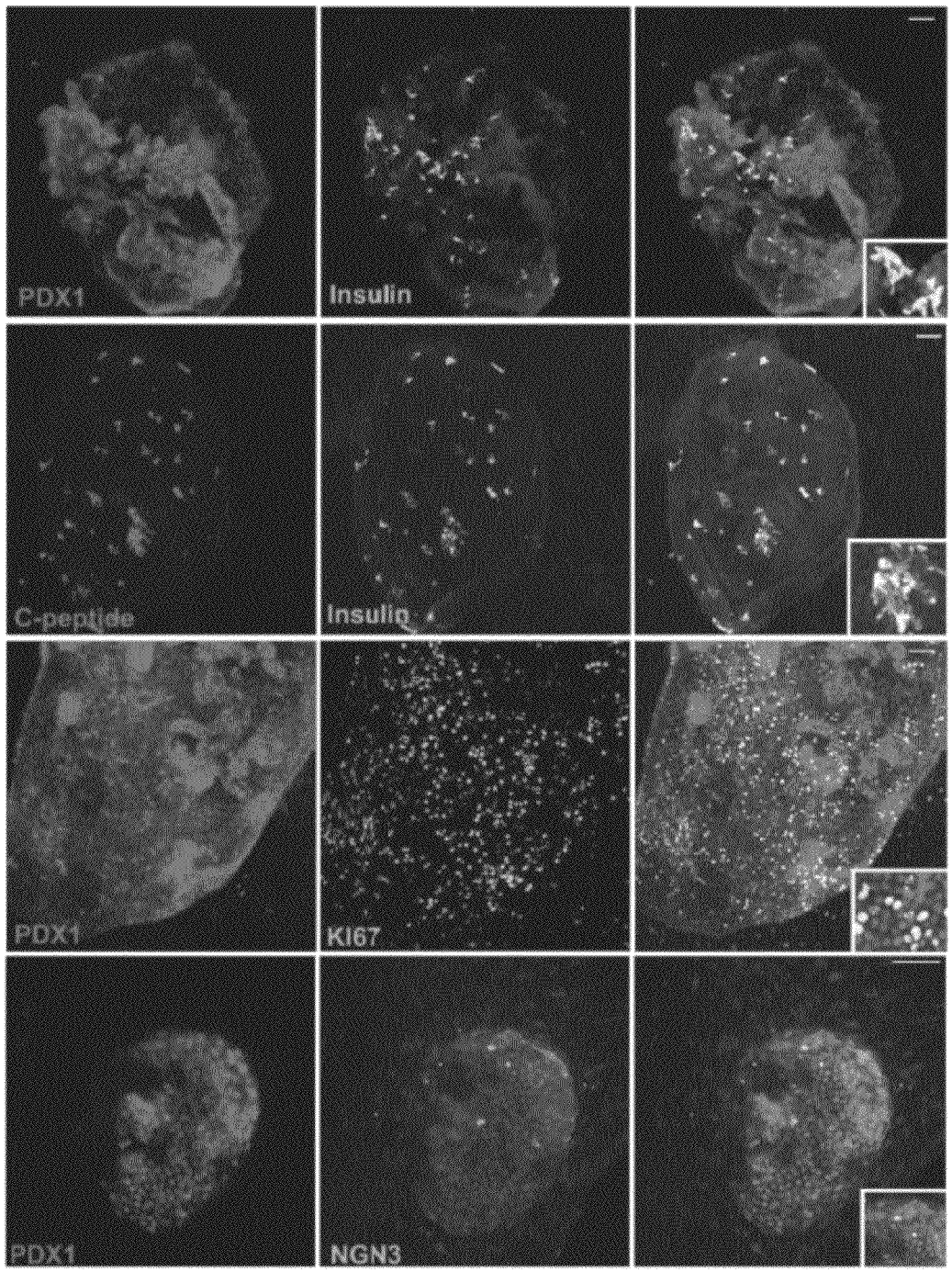
FIG. 18 reveals the expression of endocrine and late stage pancreas markers in Stage 3 cells. Many cells coexpress PDX1 and insulin, or C-peptide and insulin. Many PDX1$^+$ cells at this stage are proliferative, as shown by co-expression of PDX1 and Ki67. In some pancreas-spheres, most PDX1$^+$ cells also express NGN3. Scale bars 50 µm.

Immunostaining revealed that the cell clusters were almost 100% positive for FOXA2, SOX9, HNF6, HNF1β and PDX1 (FIGS. 16 and 17). The significant increase in the number of PDX1$^+$ cells from stage 2 to stage 3 (e.g., compare FIG. 14 with FIGS. 17 and 18) suggests either that Stage 3 medium is selective for growth of this population or that the subset of Stage 2 cells that were not PDX1$^+$ progressively differentiated into PDX1$^+$ cells. Within these large areas of PDX1$^+$ cells, some cells also co-express NKX6.1, PTF1a (FIG. 17), or Insulin (FIG. 18). Branch-like structures sometimes appear within cell-clusters, and are co-stained with PDX1 and CPA1 (FIG. 17). Cells outside of the cell clusters were never found to express these markers. Proliferating Ki67-positive cells were found both within and outside of pancreas-sphere cells (FIG. 18). In many areas of PDX1$^+$ cells, there is co-expression of MafA, which is not seen outside the PDX1$^+$ regions (data not shown). Mature beta cells express MafA but not MafB (Nishimura et al., 2006). In our hands, MafB staining has not been successful, so full interpretation of MafA staining is not possible. Insulin-positive cells were found within cell clusters throughout Stage 3, and co-stain with both PDX1 and C-peptide (not shown). At the end of Stage 3, the mean number of positive cells per culture well (in 24-well plates) was 168.

The expression of PDX1 in the cell clusters is considerably greater than previous techniques, such as those disclosed in U.S. Patent Application Publication No. 2011/0081720 (40-50% PDX1$^+$/Sox9$^+$ cells). In fact, PDX1 expression was comparable to that found in 50% pure human islets. Also, almost all cells are EpCAM$^+$ (data not shown).

QPCR data suggest that Stage 1 treatment of hESCs influences their differentiation capacities at subsequent stages. For example, FAB treatment results in higher expression of PDX1 and FOXA2 at Stages 2 and 3 compared to CMBF or ITSFAB treatment (FIG. 13). The level of FOXA2 transcripts in FAB-treated cultures diminishes from Stage 2 to 3 (41 and 21 fold changes versus untreated spontaneously differentiated EBs, respectively), whereas PDX1 transcripts increase from 175 to 1158 fold change in Stage 2 and 3, respectively, as would be expected if endoderm is further differentiating to the foregut/pancreas lineage. A timecourse of gene expression reveals that SOX9, HNF6, CPA1, and NGN3 transcript levels are very low or undetectable in undifferentiated hESCs and Stage 1 cells. At Stage 2 there is a modest increase in SOX9 transcripts, and a 73 fold increase in HNF6 expression, compared with hESCs. By Stage 3, expression levels of each of these transcripts have increased compared to the baseline expression level: SOX9, 27.5 fold; HNF6, 311 fold; CPA1, 13 fold; NGN3, 78 fold (FIG. 13).

For Stage 4, ITSFINE medium was switched to NB medium (nicotinamide and B27) for an additional 5-14 days in order to promote endocrine differentiation. At the end of this stage, the insulin content increased dramatically, both at transcript level (delta CT went from 9 to 5) and at protein level (see FIGS. 13 and 19) compared to Stage 3. The mean number of Insulin$^+$ cells per culture well (in a 24-well plate) was 1795, ten times the number seen at the end of Stage 3. In Stage 3 cultures, Insulin$^+$ cells were more scattered, whereas by the end of the fourth stage, some Insulin$^+$ cells are found clustered together. The clustering and increase in number of cells suggests the possibility that these new Insulin$^+$ cells arose by either proliferation of existing Insulin$^+$ cells or differentiation from some type of progenitor cell, or both Immunostaining of cells at the end of Stage 3 demonstrated that some Insulin$^+$ cells co-expressed Ki67, suggesting that some Insulin$^+$ cells were dividing at this time. However, the majority of Insulin$^+$ cells do not stain with Ki67, and in the 4th stage, virtually no Insulin$^+$/Ki67$^+$ co-stained cells were observed (not shown). Therefore, it is likely that most Insulin$^+$ cells in these late stage cultures arise by differentiation from Insulin-negative cells.

Figure 19:
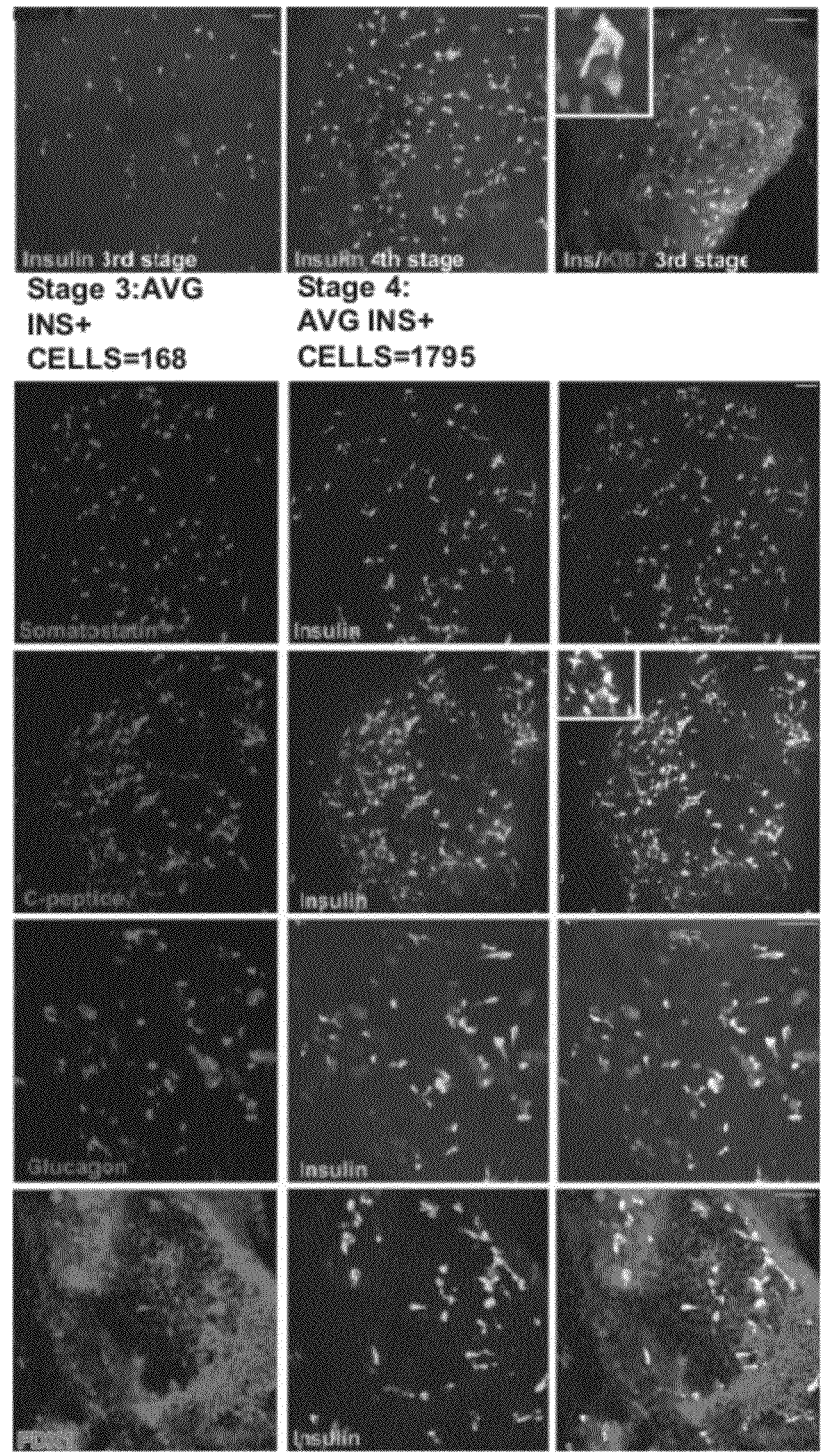
FIG. 19 reveals expression of endocrine hormones in Stage 3 and Stage 4 cells. Insulin$^+$ cells per well in a 24-well plate were counted and an average number of insulin$^+$ cells from three wells was indicated under the representative figure. Some insulin$^+$ cells at 3rd stage are proliferative, as shown by co-expression of insulin and Ki67. Stainings of glucagon, C-peptide and somatostatin of cells at 4$^{th}$ stage are also shown here. Many cells coexpress PDX1 and insulin, or C-peptide and insulin. Scale bars 50 µn.

Insulin$^+$ cells in these cultures also co-express C-peptide (FIG. 19), demonstrating that the cells are synthesizing insulin and not taking it up from the medium. The cultures also have many somatostatin- and glucagon-expressing cells (FIG. 19). In some cases, these cells co-express insulin, revealing that they are immature endocrine cells. However, the vast majority of insulin$^+$ cells at this stage do not co-express other pancreatic hormone proteins. The literature (Cabrera et al., 2006) shows the ratio of Insulin$^+$:Glucagon$^+$: Somatostatin$^+$ cells in human islets as approximately 1:0.74: 0.19. In our cultures at Stage 4, the ratio is 1:0.46:1.09, revealing that our cultures have fewer glucagon$^+$ cells and many more somatostatin$^+$ cells than typically found in adult human islets. The average C-peptide concentration detected in media at the fourth stage is approximately 83±16 µM (n=8) and is similar to the amount of insulin detected in vitro in the study by D'Amour et al. (D'Amour et al., 2006). The presence of various endocrine cell types indicates the authenticity of pancreatic lineage differentiation.

Discussion

The procedure described above was developed for obtaining enriched pancreatic progenitors and islet-like cell clusters from hESCs. This protocol was developed by first taking a rational approach based on known developmental signals, followed by empirical testing to refine it. The stepwise differentiation process should be monitored at different time points for expression of stage-specific markers at both gene and protein levels. This method appears to work equally well for human ES cells and iPS cells. An important aspect of this procedure is to begin with healthy colonies of low passage, normal-appearing undifferentiated pluripotent stem cells, ideally at 80% confluence. If non-optimally maintained, some stem cell colonies exhibit spontaneous differentiation at the periphery of colonies. In our experience, even mild amounts of spontaneous differentiation within stem cell colonies can lead to significantly altered responses to growth factors and result in heterogeneity at later stages of differentiation.

The experimental results herein indicate that early cell fates are highly dependent on the combinatorial effects of Activin A, bFGF, and BMP4 growth factors. The induction of Gsc, Mixl1, Sox17 and Foxa2 expression by Activin A is not adversely affected by the addition of BMP4. Moreover, adding both BMP4 and bFGF to Activin A-treated cells in serum/ serum replacement-free defined media also maintains the expression of Gsc Mixl1, and Foxa2 induced by Activin A and further enhances the expression of T and Sox17. Importantly, hESCs grown in FAB medium survive better than if they are differentiated in Activin A alone. Not only do FAB-treated hESCs survive better and show enhanced DE gene expression compared to Activin A only treated cells, but they are able to further differentiate and form EBs.

Insulin also plays a significant inhibitory role in early differentiation. Adding insulin to Activin A does not affect the induction of Gsc and Mixl1, but significantly decreases the expression of Sox17 and Foxa2. Similar gene expression changes and reduced DE marker expression occurs when insulin is added to FAB. On the other hand, insulin enhances the expression of T and other mesoderm markers Tbx6, Meox1 and KGR. These gene expression changes can be interpreted as indicating that insulin signaling promotes hESC differentiation into primitive streak and mesendoderm, but not endoderm. Instead, early cells are pushed towards the mesoderm lineage.

Our protocol leads to reliable production of sphere-shaped cell clusters called "pancreas-spheres." These three dimensional cell clusters are almost 100% positive for HNF1b, HNF6, FOXA2, SOX9 and PDX1 and partly positive for Nkx6.1, Ptf1a, and CPA1 reminiscent of pancreatic progenitor epithelium (Oliver-Krasinski and Stoffers, 2008). The FAB-based culture protocol in chemically-defined media described here yields similar quantities of DE and pancreatic progenitors from three human iPS cell lines derived from iPS (IMR-90)-4-MCB-1, iPS (Foreskin)-1-MCB-1, and DF 19-9-7T-MCB-01 (data not shown), in addition to hESC lines H1 and H9.

Endocrine hormone-producing cells were also generated by this differentiation protocol. Insulin, glucagon, and somatostatin were all found in these cell clusters. Although a small percentage of cells are polyhormonal, most hormone-positive cells express a single hormone and are in close relationship with each other. Nearly all insulin$^+$ cells also were PDX1$^+$ and C-peptide$^+$, indicative of beta-like cells. Numerous functional studies suggest the importance of the three-dimensional structure of the islet and direct interactions between various islet endocrine cells, including beta cell-beta cell and beta cell-alpha cell interactions (Miller et al., 2009). Compared to a two dimensional hESC culture system, the pancreas-sphere is one step advanced in terms of promoting interactions among cells expressing different hormones. Notably, all pancreatic lineage-associated marker stained cells were expressed only in cells within pancreas-spheres, even though there were cells present in the cultures outside of the pancreas-spheres. This characteristic may facilitate the incorporation of straightforward methods for further purification.

Example 2

Alternate Protocol

Figure 2:
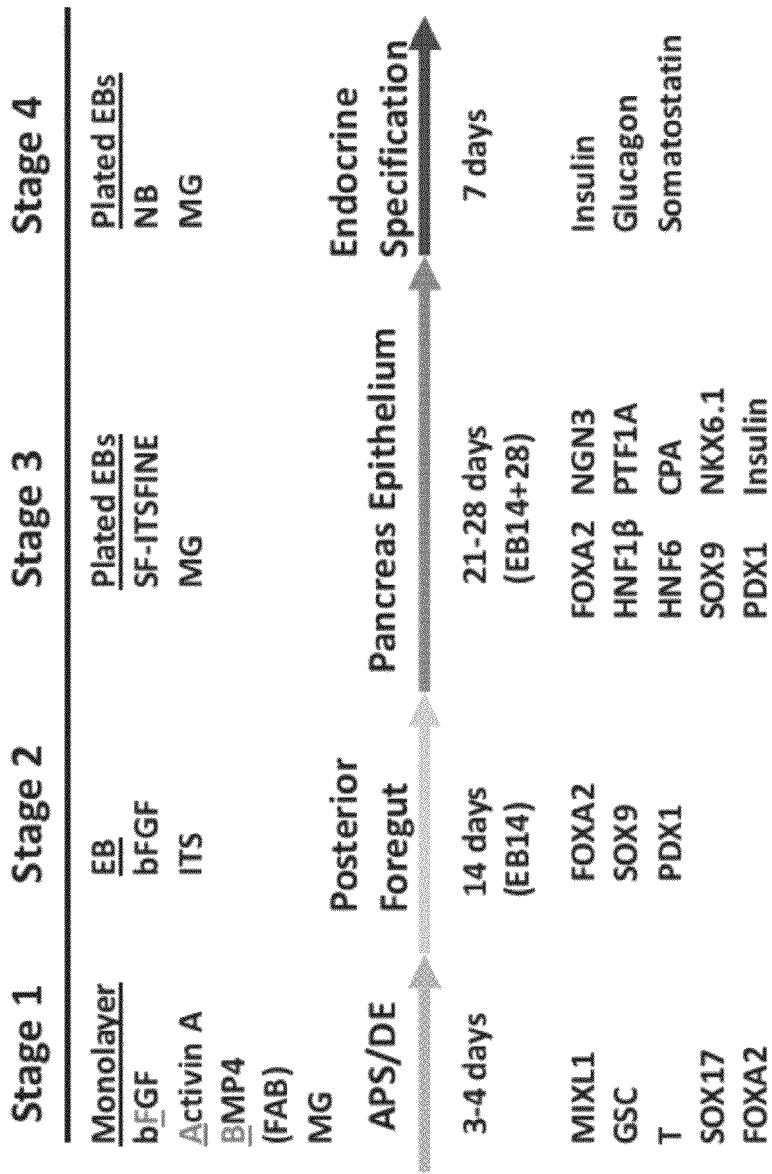
FIG. 2 is another flow chart depicting a method of in vitro differentiation of pancreatic cell lineages from pluripotent stem cells. APS—anterior primitive streak; DE—definitive endoderm; MG—Matrigel™; NB—nicotinamide- and B27-containing media.
Figure 20:
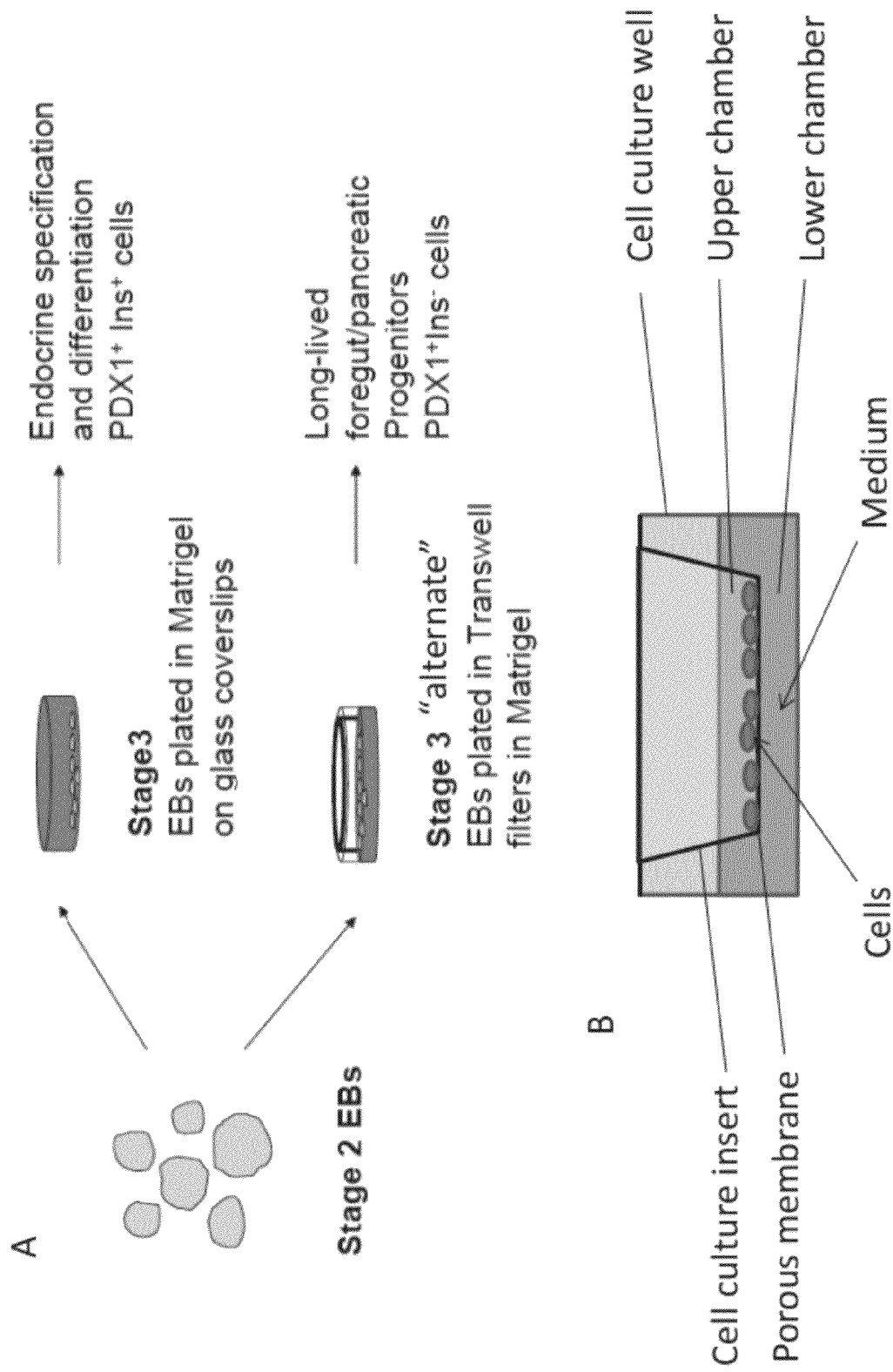
FIG. 20 includes FIGS. 20A and 20B.

As depicted in FIGS. 1 and 20, rather than suspending EBs from Stage 2 in Matrigel™ on coverslips, an alternate method has been developed to establish long-lived pancreatic/foregut progenitor cells. Here, EBs developed as described above in Example 1 were taken after Stage 2, prepared as described in Stage 3, but rather than seeding on coverslips, the Matrigel-embedded cells were seeded on Transwell™ inserts (Corning) in ITSFINE medium. Similar to Stage 3 under the Standard Protocol, medium was refreshed every other day.

Figure 21:
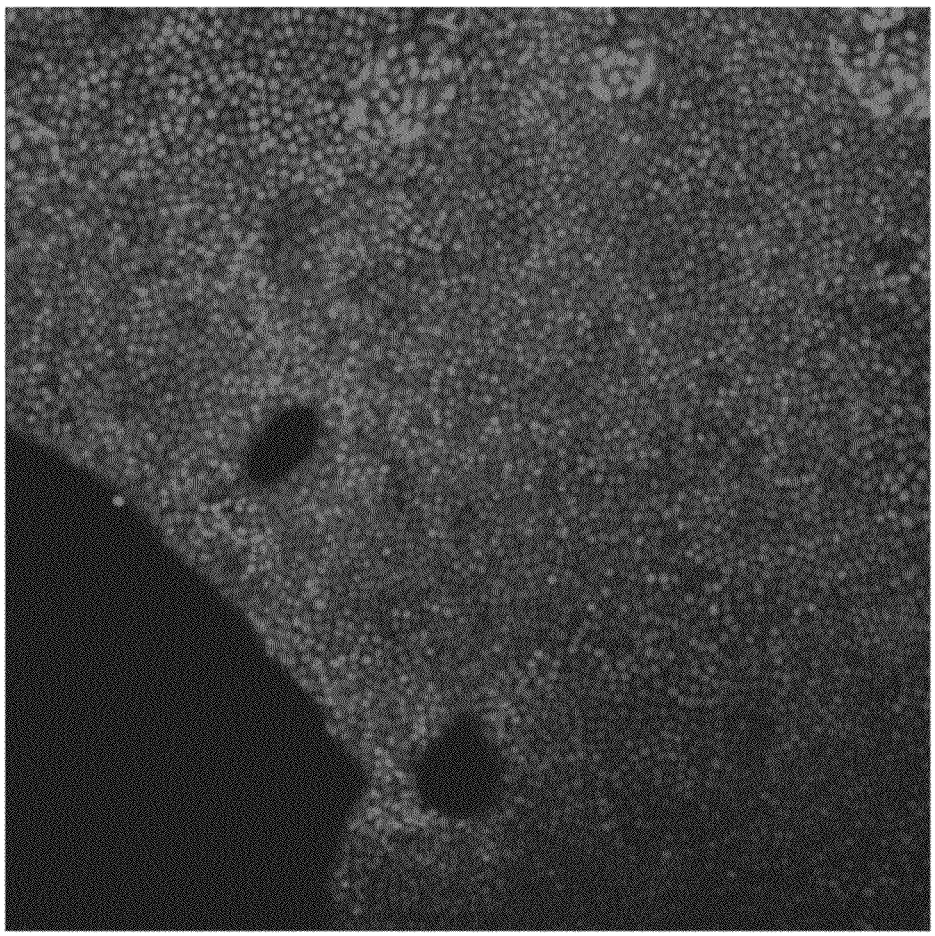
FIG. 21 shows cells cultured under the Alternate Protocol to maintain long-lived pancreatic/foregut progenitor cells, as described in FIG. 1 above. After 112 days of culture in Matrigel™ on Transwell™ inserts in the same medium as is used for the Standard Protocol Stage 3, cells were immunostained for PDX1 expression. Cells cultured in Transwell™ inserts using the Alternate Protocol maintain robust expression of PDX1 for over 100 days unlike cells cultured under the Standard Protocol's Stage 3 conditions. In addition, PDX1$^+$ cells do not go on to express insulin as is typically seen under the Standard Protocol's Stage 3 conditions.

It was discovered that EB-derived cells cultured in this way were enriched in PDX1$^+$/Ins$^-$ cells, which were maintained in a stable culture up to 112 days from Stage 1 (FIG. 21). In contrast, if cells are maintained in Stage 3 conditions of the Standard Protocol for more than 3-4 weeks, PDX1$^+$/Sox9$^+$ progenitors are lost (data not shown). It is believed that this Alternate Protocol may prove very useful for accelerating the process for supplying terminally differentiated cells for a given purpose. By maintaining a long-lived progenitor population, researchers or clinicians may be able to quickly derive terminally differentiated cells, as the need arises, within a matter of days (for example, the length of time to complete Stage 4 or similar step). Such an approach considerably shortens the length of time for deriving terminally differentiated cells compared to performing all of Stages 1-4 of the Standard Protocol each time terminally differentiated cells are required. Moreover, this approach may lead to considerable cost savings by avoiding the repetition of Stages 1-3 every time differentiated cells are required. Such time and cost savings may greatly increase the efficiency of providing "disease in a dish" assays, where terminally differentiated pancreatic lineage cells are required, like β cells.

It is further believed that the same and/or similar approaches may be utilized for maintaining long-lived progenitor cells of different lineages, such as liver, gut, cardiac, and neural progenitors among others. Therefore, this approach may provide considerable savings of time and money for directed stem cell differentiation techniques in general and not just for cells of the pancreatic lineage.

Example 3

Induced Pluripotent Cells

Figure 22:
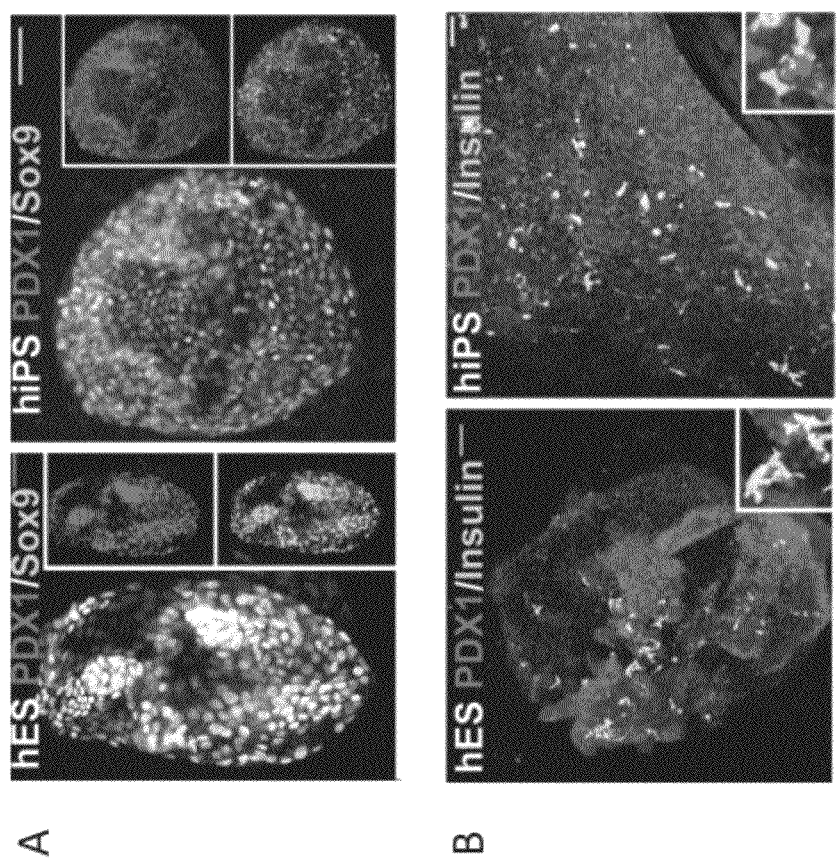
FIG. 22 is a representation of successful differentiation of human iPS cells through Stage 3. Comparison of hESC (left) and hiPS cells (right) costained for PDX1 and Sox9 (A) or PDX1 and Insulin (B). Human ESC and iPS Stage 3 pancreas spheres were indistinguishable morphologically and in their expression of the aforementioned markers. Scale bars 50 µm.

Similar to Example 1, which focused on hESCs, hiPS cells including iPS (Foreskin), clone 1, lot name: iPS (Foreskin)-1-DL-1, iPS (IMR90), clone4, lot name: iPS (IMR90)-4-DL-1, and iPS-DF19-9, clone 7T, lot number: iPS-DF19-9-7T-MCB-01 were successfully differentiated through Stage 3 following the Standard Protocol of Example 1. As seen in FIG. 22, immunostaining revealed that hiPS cell pancreas spheres expressed the same markers of differentiation and in the same temporal pattern as hESCs cultured in parallel.

Example 4

Simplified Protocol

Figure 23:
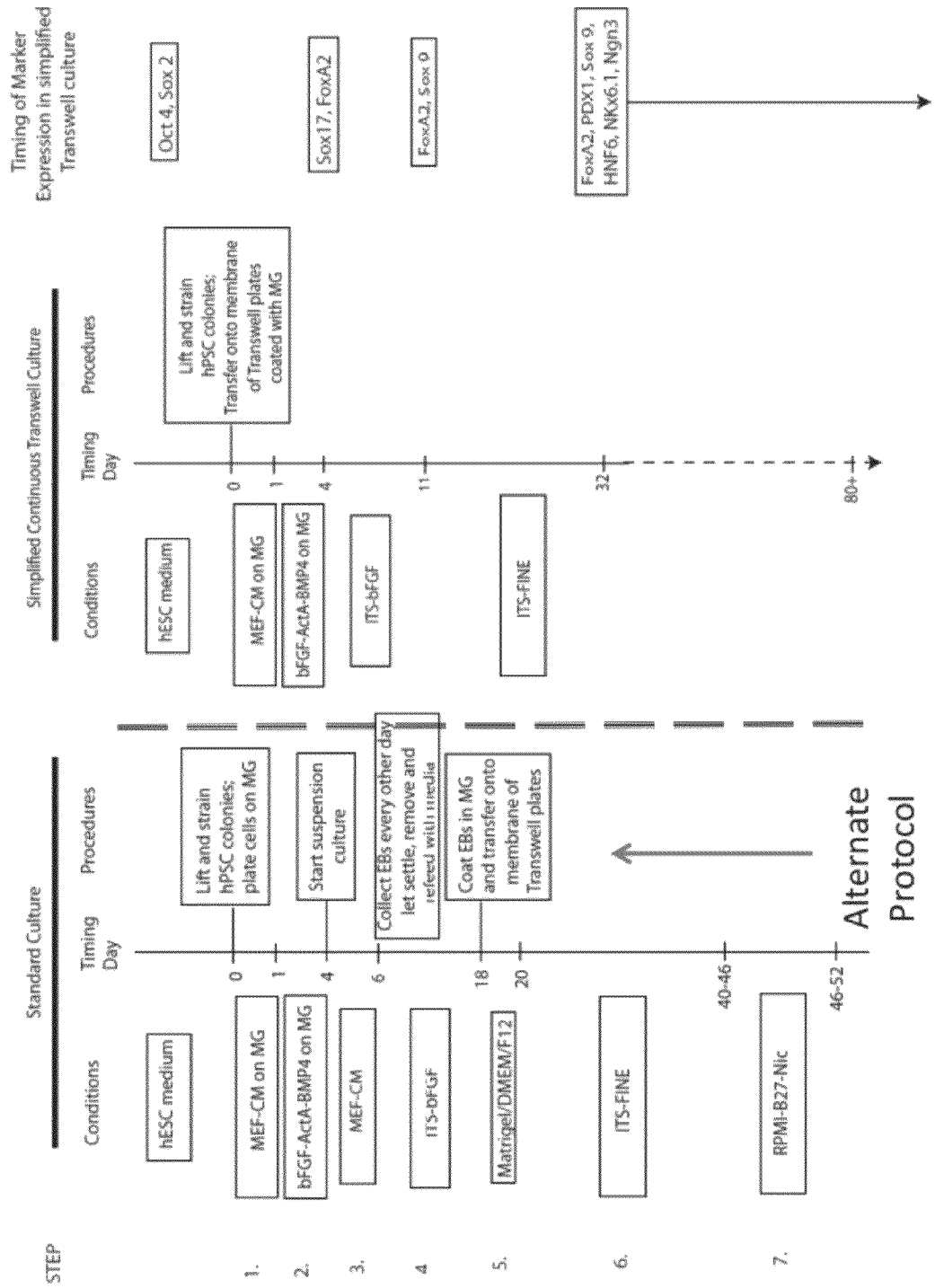
FIG. 23 illustrates a comparison of a Simplified Protocol for cultivating pancreatic progenitor cells where hPSCs are cultured ab initio on permeable substrates (right panel) versus the Standard/Alternate Protocols discussed with reference to FIGS. 1 and 21 above (left panel). Observations of cells cultured through Stages 1-3 for both Standard and Simplified Protocols include expression of Sox17 and FoxA2 at Stage 1, FoxA2 and Sox 9 at Stage 2, and FoxA2, PDX1, SOX9, HNF6, NKx6.1, and ngn3 at Stage 3.

In a further embodiment, a Simplified Protocol has been developed to establish long-lived pancreatic/foregut progenitor cells. A comparison of the Standard/Alternate Protocols (left panel) versus the Simplified Protocol (right panel) is shown in FIG. 23. In the Simplified Protocol, hESCs are seeded initially and thereafter maintained on MB-treated porous membranes, such as, for example, Transwell™ inserts. In this way, the Simplified Protocol avoids multiple substrate changes and requires fewer steps than either the Standard or Alternate Protocols. There are 3 stages to the Simplified Protocol.

Stage 1. Under the Simplified Protocol, human pluripotent stem cells, hESCs, were seeded on MG-treated Transwell™ inserts in MEF-conditioned medium following the same procedure disclosed Example 1. At the initial seeding, the hESCs express Oct 4 and Sox 2 (data not shown). After being cultured overnight, the hESCs were washed and incubated in FAB medium for 3 days.

Stage 2. The hPSCs were next cultured in ITS-bFGF medium for a period of 7 days.

Stage 3. From day 11 onward, the cells were maintained in ITS-FINE medium.

Figure 24A:
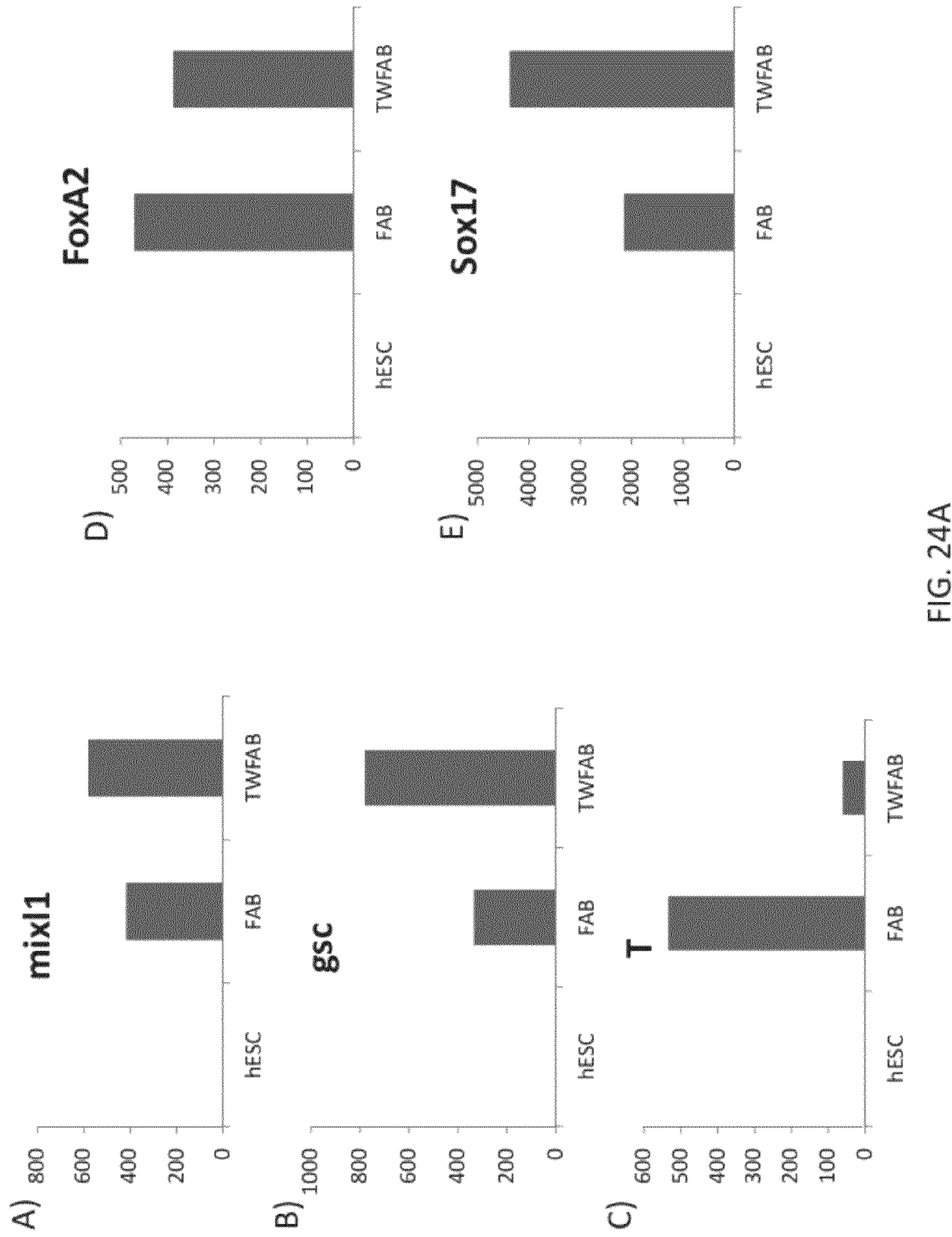
FIG. 24A illustrates a comparison of mesendodermal (A; T, brachyury), primitive streak (B; mixl1 and C; gsc), and definitive endoderm (D; FoxA2 and E; Sox17) markers between hESCs cultured according to the Standard (FAB) and Simplified Protocols (TWFAB) at Stage 1.

A comparison by stage of hESCs cultured according to the Standard and Simplified Protocols is shown in FIGS. 24A and B. In FIG. 24A, Stage 1 hESCs have comparable levels of mixl1 (A), though levels of gsc (B) appear higher, and levels of T (C) appear considerably lower under Simplified Protocol. Stage 1 hESCs have comparable levels of FoxA2 (D), though definitive endoderm marker Sox17 (E) appears higher under the Simplified Protocol.

Figure 24B:
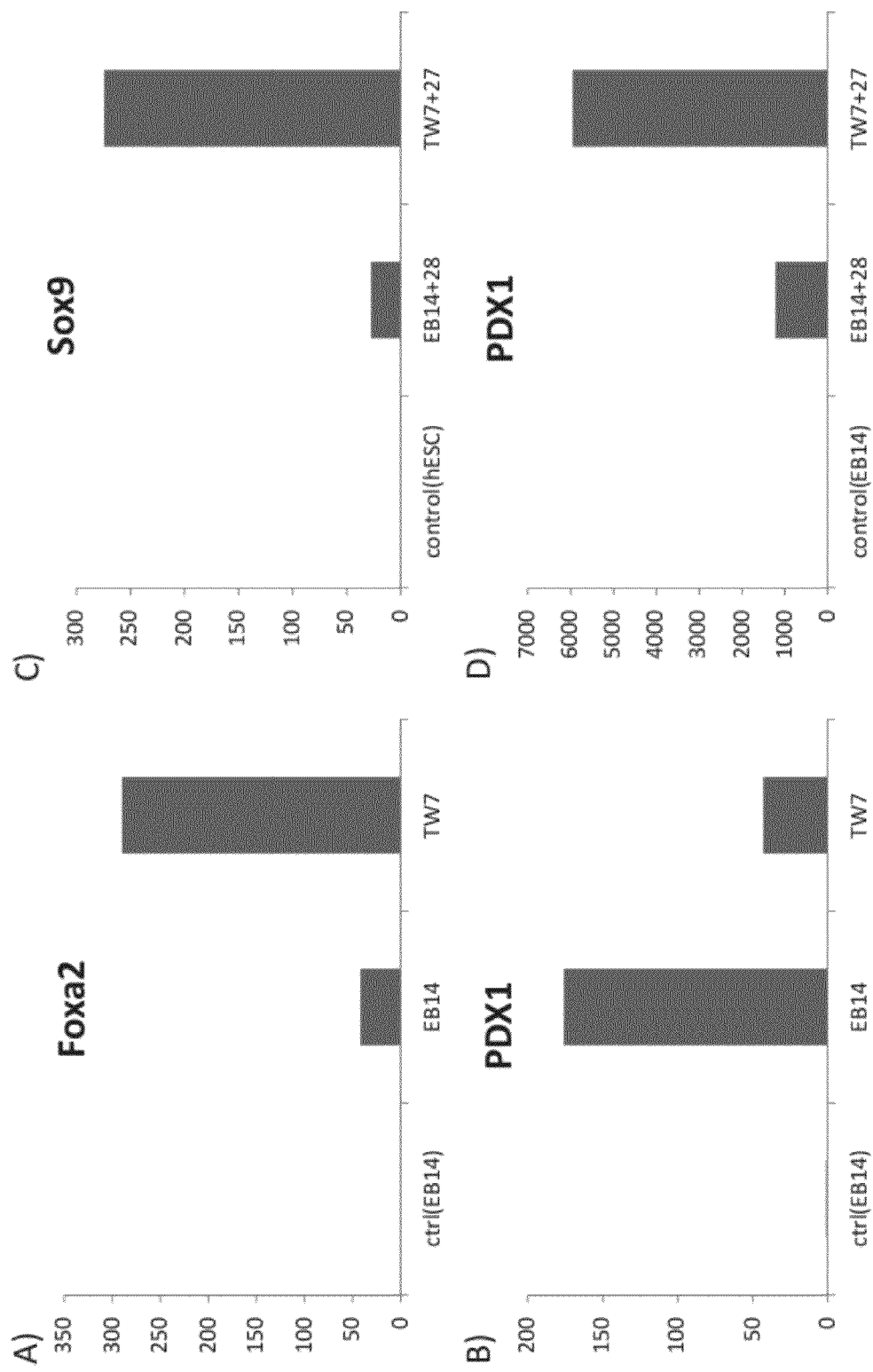
FIG. 24B illustrates a comparison of definitive endoderm (A; FoxA2) and pancreatic lineage (B; PDX1) markers between hESCs cultured according to the Standard (EB14) or Simplified (TW7) Protocols at Stage 2 and a comparison of pancreatic lineage (C; Sox9 and D; Pdx1) markers between hESCs cultured according to the Standard (EB14+28) or Simplified (TW7+27) Protocols at Stage 3.

In FIG. 24B, considerable contrasts appear between the Standard and Simplified Protocols in Stages 2 and 3. During stage 2, considerably higher levels of FoxA2 (A) are seen under the Simplified Protocol, though lower levels of PDX1 (B) are seen. However, by stage 3, both Sox9 (A) and PDX1 (B) expression levels under the Simplified Protocol appear much higher than under the Standard Protocol, suggesting a greater pancreatic progenitor enrichment under the Simplified Protocol versus the Standard Protocol. Similar trends are expected between the Alternate and Simplified Protocols. Under the Simplified Protocol, the cells maintained under Stage 3 conditions continue to express FoxA2, PDX1, Sox9, HNF6, NKx6.1, and Ngn3 for extended periods of time. At 87 days after the initiation of culture on ITS-FINE, PDX1 expression levels as measured by QT-PCR were 657 times higher than control (Day 14 EB from Standard Protocol).

While the Simplified Protocol offers advantages over the Alternate Protocol, both the Alternate and Simplified Protocols share certain characteristics. For example, either protocol may use a variety of porous substrates, including but not limited to Transwell™ inserts. Porous substrates contemplated include any physiologically acceptable substrate materials upon which human pluripotent stem cells may be cultured. Additionally, the porous substrates may be either a relatively soft material, such as a membrane or other pliable material, or a hard material that resists bending. Contemplated materials for the porous substrates include, for example, polyester and polycarbonate, but any suitable material may be used. Contemplated pore sizes may range from a size sufficient only to allow media components through to a size just below that through which a cell may migrate. For example, pore sizes may be between 0.01 μm and 3 μm (±10%), or 0.4 μm (±10%), or 3 μm (±10%). Moreover, it is contemplated that in certain embodiments, the porous substrates may incorporate or be coated with one or more growth factors, extracellular matrix components, nutrients, antibiotics, or other chemicals that may directly or indirectly help maintain cells cultured thereon or in proximity thereof, for example, if implanted into a subject.

Further, for both the Alternate and Simplified Protocols, co-culture of hESCs seeded in an upper (apical) chamber having a porous floor with vascular endothelial cells, such as cell line MS1 (a mouse pancreatic endothelial cell line; available from ATCC, ATCC No. CRL-2279) and/or VEGF seeded in a lower (basolateral) chamber and cultured with ITS-FINE medium during the latter stages of each protocol has been found to further support the growth of PDX1 expressing cells. Progenitor cells from both Protocols cultured under these conditions express PDX1, SOX9, and Ki67 (data not shown). On the other hand, the Simplified Protocol ultimately renders a more homogeneous $PDX1^+SOX9^+$ pancreatic progenitor cell population (data not shown).

Additional shared characteristics among the Standard, Alternate, and Simplified Protocols include the media that each Protocol uses, though the Simplified Protocol does not require a second stage with MEF-CM nor RPM1-B27-nicotinamide (see FIG. 23). However, each Protocol uses the same growth factors, as summarized in Table No. 4 below.

TABLE NO. 4

Comparison of Standard/Alternate and Simplified Protocols.

| Standard Protocol (Simplified Protocol) | Growth Factors | Concentration |
| --- | --- | --- |
| step 2(1) | bFGF | 100 ng/ml |
|  | Activin A | 100 ng/ml |
|  | BMP4 | 50 ng/ml |
| step 4 (2) | bFGF | 50 ng/ml |
| step 6 (3) | FGF7 | 10 ng/ml |
|  | Nicotinamide | 10 mM |
|  | ex-4 | 10 nM |

In addition, it is contemplated that ranges of the indicated growth factors described in Table No. 4 may be utilized, as described in Table No. 5 below.

TABLE NO. 5

Concentration Ranges of Growth Factors for Standard and Simplified Protocols.

| Standard Protocol (Simplified Protocol) | Growth Factors | Concentration ranges* |
|---|---|---|
| step 2 (1) | bFGF | 10-200 ng/ml |
| | Activin A | 10-100 ng/ml |
| | BMP4 | 10-50 ng/ml |
| step 4 (2) | bFGF | 10-200 ng/ml |
| step 6 (3) | FGF7 | 10-100 ng/ml |
| | Nicotinamide | 1-100 mM |
| | ex-4 | 1-100 nM |

*Values shown further contemplate a variation ±10%.

In summary, hESCs can be maintained in the same state for very long periods of time utilizing the Simplified Protocol. Compared to the culture conditions under the Standard Protocol or the Alternate Protocol, the Simplified Protocol involves fewer steps with steps 3, 5, 7 of the Standard Protocol being eliminated. Transitions back and forth between adherent plastic and suspension culture are not required in the Simplified Protocol. Further, in the Simplified Protocol, Stage 2 was shortened to 1 week instead of 2 weeks in the Standard Protocol. Ultimately, a more homogeneous population of $PDX1^+SOX9^+$ cells resulted with the Simplified Protocol (data not shown).

Example 5

Cell Culture Implant Platforms

It is further contemplated that cultured pancreatic progenitor implant platforms may be constructed with pancreatic progenitor cells seeded on porous membranes. In this example, the implant platforms are based on a bicameral cell culture system with an upper chamber and a lower chamber separated by a porous membrane. In one example, the porous membrane may be at least partially biodegradable. Contemplated porous membranes have a pore size that restricts migration of cells between upper and lower chambers. Suitable cells, such as hESCs or induced pluripotent cells are seeded in the upper chamber following the steps of either the Standard or Simplified Protocols described above. If the cells are seeded as in the Standard Protocol, then the Alternate Protocol is followed as described. If the cells are initially seeded in the upper chamber, then the Simplified Protocol is followed. Once pancreatic progenitor cells have been obtained following the protocols disclosed herein, then the cells may be further differentiated with, for example, Notch inhibitors including, for example, DAPT (N[N-(3,5-difluorophenacetyl)-1-alanyl]-S-phenylglycine t-butyl ester) (available from Sigma-Aldrich, St. Louis, Mo.) and/or removal of FGF7 from the medium or other methods, into insulin producing pancreatic lineage cells. Thereafter, the cells may be lifted from the porous membrane and implanted into a subject in need thereof. Alternatively, the porous membrane harboring the progenitor cells may be implanted into the subject as a unit. In one embodiment, the stems cells may be treated in a single step to differentiate into insulin producing cells of the pancreatic lineage and either removed from the platform for implantation into a subject or implanted into a subject along with the porous substrate. It is further contemplated that terminal differentiation into pancreatic lineage cells may be affected by transplantation of the implant or lifted cells by the recipient subject's own tissues.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

Ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

INCORPORATION BY REFERENCE

All publications and patents mentioned herein are hereby incorporated by reference in their entirety as if each individual publication or patent was specifically and individually indicated to be incorporated by reference.

RELATED PUBLICATIONS

1. Assady, S. et al. Insulin production by human embryonic stem cells. *Diabetes*, 50, 1691-1697 (2001).
2. Segev, H., Fishman, B., Ziskind, A., Shulman, M., and Itskovitz-Eldor, J. Differentiation of human embryonic stem cells into insulin-producing clusters. *Stem Cells* 22, 265-274 (2004).
3. Jonsson, J., Carlsson, L., Edlund, T., & Edlund, H. Insulin-promoter-factor 1 is required for pancreas development in mice. *Nature* 371, 606-609 (1994).
4. Sipione, S., Eshpeter, A., Lyon, J. G., Korbutt, G. S., & Bleackley, R. C. Insulin expressing cells from differentiated embryonic stem cells are not beta cells. *Diabetologia* 47, 499-508 (2004).
5. Rajagopal, J., Anderson, W. J., Kume, S., Martinez, O. I., & Melton, D. A. Insulin staining of ES cell progeny from insulin uptake. *Science*. 299, 363 (2003).
6. Brolen, G. K., Heins, N., Edsbagge, J., & Semb, H. Signals from the embryonic mouse pancreas induce differentiation of human embryonic stem cells into insulin producing beta-cell-like cells. *Diabetes* 54, 2867-2874 (2005).
7. Schuldiner, M., Yanuka, O., Itskovitz-Eldor, J., Melton, D. A., & Benvenisty, N. Effects of eight growth factors on the differentiation of cells derived from human embryonic stem cells. *Proc Natl Acad Sci USA* 97, 11307-11312 (2000).
8. D'Amour, K. A. et al. Efficient differentiation of human embryonic stem cells to definitive endoderm. *Nat. Biotechnol.* (2005).
9. Wells, J. M. & Melton, D. A. Early mouse endoderm is patterned by soluble factors from adjacent germ layers. *Development* 127, 1563-1572 (2000).
10. Kumar, M., Jordan, N., Melton, D., & Grapin-Botton, A. Signals from lateral plate mesoderm instruct endoderm toward a pancreatic fate. *Dev. Bioi.* 259, 109-122 (2003).
11. Kahan, B. W., Jacobson, L. M., Hullett, D. A., Oberley, T. D., & Odorico, J. S. Pancreatic precursors and differentiated islet cell types from murine embryonic stem cells: an in vitro model to study islet differentiation. *Diabetes* 52, 2016-2024 (2003).
12. Niwa, H., Miyazaki, J., & Smith, A. G. Quantitative expression of Oct-3/4 defines differentiation, dedifferentiation or self-renewal of ES cells. *Nat. Genet.* 24, 372-376 (2000).
13. Beattie, G. M. et al. Activin A maintains pluripotency of human embryonic stem cells in the absence of feeder layers. *Stem Cells* 23, 489-495 (2005).
14. Finley, M. F., Devata, S., & Huettner, J. E. BMP-4 inhibits neural differentiation of murine embryonic stem cells. *J. Neurobiol.* 40, 271-287 (1999).
15. Bonner-Weir, S., Taneja, M., Weir, G. C., Tatarkiewicz, K., Song, K. H., Sharma, A., O'Neil, J. O., 2000. In vitro cultivation of human islets from expanded ductal tissue. Proc. Natl. Acad. Sci. U.S.A. 97, 7999-8004.
16. Cabrera, O., Berman, D. M., Kenyon, N. S., Ricordi, C., Berggren, P. O., Caicedo, A., 2006. The unique cytoarchitecture of human pancreatic islets has implications for islet cell function. Proc. Natl. Acad. Sci. U.S.A 103, 2334-2339.
17. D'Amour, K. A., Bang, A. G., Eliazer, S., Kelly, O. G., Agulnick, A. D., Smart, N. G., Moorman, M. A., Kroon, E., Carpenter, M. K., Baetge, E. E., 2006. Production of pancreatic hormone-expressing endocrine cells from human embryonic stem cells. Nat. Biotechnol. 24, 1392-1401.
18. Gamer, L. W., Wright, C. V., 1995. Autonomous endodermal determination in Xenopus: regulation of expression of the pancreatic gene XIHbox 8. Dev. Biol. 171, 240-251.
19. Gao, R., Ustinov, J., Pulkkinen, M. A., Lundin, K., Korsgren, O., Otonkoski, T., 2003. Characterization of endocrine progenitor cells and critical factors for their differentiation in human adult pancreatic cell culture. Diabetes 52, 2007-2015.
20. Gradwohl, G., Dierich, A., LeMaur, M., Guillemot, F., 2000. neurogenin 3 is required for the development of the four endocrine cell lineages of the pancreas. Proc. Natl. Acad. Sci. U.S.A. 97, 1607-1611.
21. Greber, B., Lehrach, H., Adjaye, J., 2007. Fibroblast growth factor 2 modulates transforming growth factor beta signaling in mouse embryonic fibroblasts and human ESCs (hESCs) to support hESC self-renewal. Stem Cells 25, 455-464.
22. Greber, B., Wu, G., Bernemann, C., Joo, J. Y., Han, D. W., Ko, K., Tapia, N., Sabour, D., Sterneckert, J., Tesar, P., Scholer, H. R., 2010. Conserved and divergent roles of FGF signaling in mouse epiblast stem cells and human embryonic stem cells. Cell Stem Cell 6, 215-226.
23. Gu, G., Dubauskaite, J., Melton, D. A., 2002. Direct evidence for the pancreatic lineage: NGN3+ cells are islet progenitors and are distinct from duct progenitors. Development 129, 2447-2457.
24. Hansson, M., Olesen, D. R., Peterslund, J. M., Engberg, N., Kahn, M., Winzi, M., Klein, T., Maddox-Hyttel, P., Serup, P., 2009. A late requirement for Wnt and FGF signaling during activin-induced formation of foregut endoderm from mouse embryonic stem cells. Dev. Biol. 330, 286-304.
25. Jackson, S. A., Schiesser, J., Stanley, E. G., Elefanty, A. G., 2010. Differentiating embryonic stem cells pass through 'temporal windows' that mark responsiveness to exogenous and paracrine mesendoderm inducing signals. PLoS.ONE. 5, e10706.
26. Jiang, F. X., Cram, D. S., DeAizpurua, H. J., Harrison, L. C., 1999. Laminin-1 promotes differentiation of fetal mouse pancreatic beta-cells. Diabetes 48, 722-730.
27. Kroon, E., Martinson, L. A., Kadoya, K., Bang, A. G., Kelly, O. G., Eliazer, S., Young, H., Richardson, M., Smart, N. G., Cunningham, J., Agulnick, A. D., D'Amour, K. A., Carpenter, M. K., Baetge, E. E., 2008. Pancreatic endoderm derived from human embryonic stem cells generates glucose-responsive insulin-secreting cells in vivo. Nat. Biotechnol. 26, 443-452.
28. Laflamme, M. A., Chen, K. Y., Naumova, A. V., Muskheli, V., Fugate, J. A., Dupras, S. K., Reinecke, H., Xu, C., Hassanipour, M., Police, S., O'sullivan, C., Collins, L., Chen, Y., Minami, E., Gill, E. A., Ueno, S., Yuan, C., Gold, J., Murry, C. E., 2007. Cardiomyocytes derived from human embryonic stem cells in pro-survival factors enhance function of infarcted rat hearts. Nat. Biotechnol. 25, 1015-1024.
29. Lammert, E., Cleaver, O., Melton, D., 2001. Induction of pancreatic differentiation by signals from blood vessels. Science 294, 564-567.
30. Lau, J., Kawahira, H., Hebrok, M., 2006. Hedgehog signaling in pancreas development and disease. Cell Mol. Life. Sci. 63, 642-652.
31. McLean, A. B., D'Amour, K. A., Jones, K. L., Krishnamoorthy, M., Kulik, M. J., Reynolds, D. M., Sheppard, A. M., Liu, H., Xu, Y., Baetge, E. E., Dalton, S., 2007. Activin A efficiently specifies definitive endoderm from human embryonic stem cells only when phosphatidylinositol 3-kinase signaling is suppressed. Stem Cells 25, 29-38.
32. Micallef, S. J., Li, X., Janes, M. E., Jackson, S. A., Sutherland, R. M., Lew, A. M., Harrison, L. C., Elefanty, A. G., Stanley, E. G., 2007. Endocrine cells develop within pancreatic bud-like structures derived from mouse ES cells differentiated in response to BMP4 and retinoic acid. Stem Cell Res. 1, 25-36.
33. Miller, K., Kim, A., Kilimnik, G., Jo, J., Moka, U., Periwal, V., Hara, M., 2009. Islet formation during the neonatal development in mice. PLoS ONE. 4, e7739.
34. Morrison, G. M., Oikonomopoulou, I., Migueles, R. P., Soneji, S., Livigni, A., Enver, T.,
35. Brickman, J. M., 2008. Anterior definitive endoderm from ESCs reveals a role for FGF signaling. Cell Stem Cell 3, 402-415.
36. Nikolova, G., Jabs, N., Konstantinova, I., Domogatskaya, A., Tryggvason, K., Sorokin, L., Fassler, R., Gu, G., Gerber, H. P., Ferrara, N., Melton, D. A., Lammert, E., 2006. The vascular basement membrane: a niche for insulin gene expression and Beta cell proliferation. Dev. Cell 10, 397-405.

37. Ninomiya, H., Takahashi, S., Tanegashima, K., Yokota, C., Asashima, M., 1999. Endoderm differentiation and inductive effect of activin-treated ectoderm in Xenopus. Dev. Growth Differ. 41, 391-400.
38. Nishimura, W., Kondo, T., Salameh, T., El, K., I, Dodge, R., Bonner-Weir, S., Sharma, A., 2006. A switch from MafB to MafA expression accompanies differentiation to pancreatic beta-cells. Dev. Biol. 293, 526-539.
39. Nostro, M. C., Cheng, X., Keller, G. M., Gadue, P., 2008. Wnt, activin, and BMP signaling regulate distinct stages in the developmental pathway from embryonic stem cells to blood. Cell Stem Cell 2, 60-71.
40. Oliver-Krasinski, J. M., Stoffers, D. A., 2008. On the origin of the beta cell. Genes Dev. 22, 1998-2021.
41. Otonkoski, T., Banerjee, M., Korsgren, O., Thornell, L. E., Virtanen, I., 2008. Unique basement membrane structure of human pancreatic islets: implications for beta cell growth and differentiation. Diabetes Obes. Metab 10 Suppl 4, 119-127.
42. Pera, M. F., 2004. Unnatural selection of cultured human ES cells? Nature Biotechnology. 22, 42-43.
43. Pera, M. F., Andrade, J., Houssami, S., Reubinoff, B., Trounson, A., Stanley, E. G., Ward-van Oostwaard, D., Mummery, C., 2004. Regulation of human embryonic stem cell differentiation by BMP-2 and its antagonist noggin. J. Cell Sci. 117, 1269-1280.
44. Phillips, B. W., Hentze, H., Rust, W. L., Chen, Q. P., Chipperfield, H., Tan, E. K., Abraham, S., Sadasivam, A., Soong, P. L., Wang, S. T., Lim, R., Sun, W., Colman, A., Dunn, N. R., 2007. Directed differentiation of human embryonic stem cells into the pancreatic endocrine lineage. Stem Cells Dev. 16, 561-578.
45. Seymour, P. A., Freude, K. K., Tran, M. N., Mayes, E. E., Jensen, J., Kist, R., Scherer, G., Sander, M., 2007. SOX9 is required for maintenance of the pancreatic progenitor cell pool. Proc. Natl. Acad. Sci. U.S.A 104, 1865-1870.
46. Smith, J. C., Price, B. M., Van, N. K., Huylebroeck, D., 1990. Identification of a potent Xenopus mesoderm-inducing factor as a homologue of activin A. Nature 345, 729-731.
47. Stafford, D., Hornbruch, A., Mueller, P. R., Prince, V. E., 2004. A conserved role for retinoid signaling in vertebrate pancreas development. Dev. Genes Evol. 214, 432-441.
48. Tada, S., Era, T., Furusawa, C., Sakurai, H., Nishikawa, S., Kinoshita, M., Nakao, K., Chiba, T., Nishikawa, S., 2005. Characterization of mesendoderm: a diverging point of the definitive endoderm and mesoderm in embryonic stem cell differentiation culture. Development 132, 4363-4374.
49. Tam, P. P., Loebel, D. A., Tanaka, S. S., 2006. Building the mouse gastrula: signals, asymmetry and lineages. Curr. Opin. Genet. Dev. 16, 419-425.
50. Valdimarsdottir, G., Mummery, C., 2005. Functions of the TGF beta superfamily in human embryonic stem cells. APMIS 113, 773-789.
51. Vallier, L., Alexander, M., Pedersen, R. A., 2005. Activin/Nodal and FGF pathways cooperate to maintain pluripotency of human embryonic stem cells. J. Cell Sci. 118, 4495-4509.
52. Vallier, L., Touboul, T., Chang, Z., Brimpari, M., Hannan, N., Millan, E., Smithers, L. E., Trotter, M., Rugg-Gunn, P., Weber, A., Pedersen, R. A., 2009. Early cell fate decisions of human embryonic stem cells and mouse epiblast stem cells are controlled by the same signalling pathways. PLoS.ONE. 4, e6082.
53. Vesque, C., Ellis, S., Lee, A., Szabo, M., Thomas, P., Beddington, R., Placzek, M., 2000. Development of chick axial mesoderm: specification of prechordal mesoderm by anterior endoderm-derived TGF-beta family signalling. Development 127, 2795-2809.
54. Vukicevic, S., Kleinman, H. K., Luyten, F. P., Roberts, A. B., Roche, N. S., Reddi, A. H., 1992. Identification of multiple active growth factors in basement membrane Matrigel suggests caution in interpretation of cellular activity related to extracellular matrix components. Exp. Cell Res. 202, 1-8.
55. Wells, J. M., Melton, D. A., 1999. Vertebrate endoderm development. Annual Review of Cell Developmental Biology 15, 393-410.
56. Willems, E., Leyns, L., 2008. Patterning of mouse embryonic stem cell-derived panmesoderm by Activin A/Nodal and Bmp4 signaling requires Fibroblast Growth Factor activity. Differentiation 76, 745-759.
57. Xiao, L., Yuan, X., Sharkis, S. J., 2006. Activin A maintains self-renewal and regulates fibroblast growth factor, Wnt, and bone morphogenetic protein pathways in human embryonic stem cells. Stem Cells 24, 1476-1486.
58. Xu, C., Rosier, E., Jiang, J., Lebkowski, J. S., Gold, J. D., O'sullivan, C., Delavan-Boorsma, K., Mok, M., Bronstein, A., Carpenter, M. K., 2005a. Basic fibroblast growth factor supports undifferentiated human embryonic stem cell growth without conditioned medium. Stem Cells 23, 315-323.
59. Xu, R. H., Chen, X., Li, D. S., Li, R., Addicks, G. C., Glennon, C., Zwaka, T. P., Thomson, J. A., 2002. BMP4 initiates human embryonic stem cell differentiation to trophoblast. Nature Biotechnology. 20, 1261-1264.
60. Xu, R. H., Peck, R. M., Li, D. S., Feng, X., Ludwig, T., Thomson, J. A., 2005b. Basic FGF and suppression of BMP signaling sustain undifferentiated proliferation of human ES cells. Nat. Methods 2, 185-190.
61. Xu, X., Kahan, B., Forgianni, A., Jing, P., Jacobson, L., Browning, V., Treff, N., Odorico, J., 2006. Endoderm and pancreatic islet lineage differentiation from human embryonic stem cells. Cloning Stem Cells 8, 96-107.
62. Yasunaga, M., Tada, S., Torikai-Nishikawa, S., Nakano, Y., Okada, M., Jakt, L. M., Nishikawa, S., Chiba, T., Era, T., Nishikawa, S., 2005. Induction and monitoring of definitive and visceral endoderm differentiation of mouse ES cells. Nat. Biotechnol. 23, 1542-1550.
63. Ying, Q. L., Nichols, J., Chambers, I., Smith, A., 2003. BMP induction of 1d proteins suppresses differentiation and sustains embryonic stem cell self-renewal in collaboration with STAT3. Cell 115, 281-292.
64. Zhang, P., Li, J., Tan, Z., Wang, C., Liu, T., Chen, L., Yong, J., Jiang, W., Sun, X., Du, L., Ding, M., Deng, H., 2008. Short-term BMP-4 treatment initiates mesoderm induction in human embryonic stem cells. Blood 111, 1933-1941.
65. Zhou, Q., Law, A. C., Rajagopal, J., Anderson, W. J., Gray, P. A., Melton, D. A., 2007. A multipotent progenitor domain guides pancreatic organogenesis. Dev. Cell 13, 103-114.
66. Zorn, A. M., Wells, J. M., 2009. Vertebrate endoderm development and organ formation. Annu. Rev. Cell Dev. Biol. 25, 221-251.
67. Jiang, J., et al., Generation of Insulin-Producing Islet-Like Clusters from Human Embryonic Stem Cells, *Stem Cells*, Vol. 25, 2007, pp. 1940-53.
68. Phillips, B. W., et al., Directed Differentiation of Human Embryonic Stem Cells into the Pancreatic Endocrine Lineage, *Stem Cells Dev.*, Vol. 16, 2007, pp. 561-78.
69. Shim, J. H., et al., Directed Differentiation of Human Embryonic Stem Cells Towards a Pancreatic Cell Fate, *Diabetologia*, Vol. 50, 2007, pp. 1228-38.

70. McLean, A. B., et al., Activin A Efficiently Specifies Definitive Endoderm from Human Embryonic Stem Cells Only When Phosphatidylinositol 3-Kinase Signaling Is Suppressed," *Stem Cells*, Vol. 25, 2007, pp. 29-38.
71. Touboul, T., et al. "Generation of Functional Hepatocytes from Human Embryonic Stem Cells under Chemically Defined Conditions that Recapitulate Liver Development," *Hepatology*, Vol. 51, 2010, pp. 1754-65.
72. Shi, Y., "Generation of Functional Insulin-Producing Cells from Human Embryonic Stem Cells In Vitro," *Meth- ods. Mol. Biol.*, Vol. 636, 2010, pp. 79-85.
73. Cai, J., et al., "Generation of Homogeneous PDX1(+) Pancreatic Progenitors from Human ES Cell-Derived Endoderm Cells," *J. Mol. Cell. Biol.*, Vol. 2, 2010, pp. 50-60.
74. Ameri, J., et al., "FGF2 Specifies hESC-Derived Definitive Endoderm into Foregut/Midgut Cell Lineages in a Concentration-Dependent Manner," *Stem Cells*, Vol. 28, 2010, pp. 45-56.
75. Sulzbacher, S., et al., Activin A-Induced Differentiation of Embryonic Stem Cells into Endoderm and Pancreatic Progenitors—The Influence of Differentiation Factors and Culture Conditions, *Stem Cell Rev.*, Vol. 5, 2009, pp. 159-73.
76. Johannesson, M., et al., FGF4 and Retinoic Acid Direct Differentiation of hESCs into PDX1-Expressing Foregut Endoderm in a Time- and Concentration-Dependent Manner, *PLoS ONE*, Vol. 4, 2009, p. e4794.
77. Hay, D. C., et al., Highly Efficient Differentiation of hESCs to Functional Hepatic Endoderm Requires ActivinA and Wnt3a Signaling, *Proc. Natl. Acad. Sci. USA*, Vol. 105, 2008, pp. 12301-306.
78. Vallier, L., et al., Signaling Pathways Controlling Pluripotency and Early Cell Fate Decisions of Human Induced Pluripotent Stem Cells, *Stem Cells*, Vol. 27, 2009, pp. 2655-66.
79. Kroon, E., et al. Pancreatic Endoderm Derived from Human Embryonic Stem Cells Generates Glucose-Responsive Insulin-Secreting Cells In Vivo *Nat. Biotechnol.*, Vol. 26, 2008, pp. 443-52.
80. Matveyenko, A. V., et al., Inconsistent Formation and Nonfunction of Insulin-Positive Cells from Pancreatic Endoderm Derived from Human Embryonic Stem Cells in Athymic Nude Rats, *Am. J. Physiol. Endocrinol. Metab.*, Vol. 299, 2010, pp. E713-E720.
81. Xu X, Browning V L, Odorico J S. Activin, BMP and FGF pathways cooperate to promote endoderm and pancreatic lineage cell differentiation from human embryonic stem cells. *Mech Dev. September;* 128 (7-10): 412-27, 2011.
82. Xu X, Browning V, Odorico J. Culture protocols for producing definitive endoderm and pancreatic lineage cells from human ES or iPS cells. *Methods in Bioengineering*, eds. M. Yarmush, R. Langer, Artech House, Boston, 2011.

We claim:

1. A method of culturing human pluripotent stem cells to produce cells of the pancreatic lineage, the method comprising the steps of:
    (a) culturing the stem cells under conditions that induce formation of mesendoderm/primitive streak and definitive endoderm cells in a chemically defined medium comprising an effective amount of
        i) fibroblast growth factor,
        ii) Activin A, and
        iii) bone morphogenetic protein;
    (b) culturing the cells from step (a) in the presence of a chemically defined medium comprising an effective amount of insulin, transferrin, and selenium, wherein the medium further comprises a fibroblast growth factor in an amount that ranges from about 10 ng/ml to about 200 ng/ml; and
    (c) culturing the cells under conditions to produce foregut/pancreatic progenitor PDX1$^+$Ins$^-$ cells.

2. The method of claim 1, wherein the stem cells are selected from the group consisting of human embryonic stem cells and human induced pluripotent stem cells.

3. The method of claim 1, wherein in step (a) the effective amount of
    i) fibroblast growth factor ranges from about 10 ng/ml to about 200 ng/ml,
    ii) Activin A ranges from about 10 ng/ml to about 200 ng/ml, and
    iii) bone morphogenetic protein ranges from about 10 ng/ml to about 100 ng/ml.

4. The method of claim 3, wherein the fibroblast growth factor comprises basic fibroblast growth factor and the bone morphogenetic protein comprises BMP4.

5. The method of claim 4, wherein in step (a) the effective amount of
    i) basic fibroblast growth factor is about 100 ng/ml,
    ii) Activin A is about 100 ng/ml, and
    iii) BMP4 is about 50 ng/ml.

6. The method of claim 1, wherein step (a) has a duration of about 3-4 days.

7. The method of claim 1, wherein the stem cells of step (b) are cultured under conditions favoring the formation of embryoid bodies.

8. The method of claim 7, wherein step (b) has a duration of about 7 to about 12 days.

9. The method of claim 7, wherein the embryoid bodies of step (b) include definitive endoderm cells with duct-like structures containing FoxA2$^+$, Sox17$^+$ and PDX1$^+$ cells.

10. The method of claim 1, wherein the chemically defined medium is serum free.

11. The method of claim 1, wherein stem cells cultured under the conditions of step (a) co-express FoxA2 and Sox 17.

12. The method of claim 1, wherein the PDX1$^+$Ins$^-$ cells may be maintained under the conditions of step (c) for at least 50 days.

13. The method of claim 1, wherein the PDX1$^+$Ins$^-$ cells may be further differentiated into PDX1$^+$Ins$^+$ cells.

14. The method of claim 1, wherein stem cells are initially seeded in step (a) on a porous substrate.

15. A method of culturing human pluripotent stem cells to produce cells of the pancreatic lineage, the method comprising the steps of:
    (a) culturing the stem cells under conditions that induce formation of mesendoderm/primitive streak and definitive endoderm cells in a chemically defined medium comprising an effective amount of
        i) fibroblast growth factor,
        ii) Activin A, and
        iii) bone morphogenetic protein;
    (b) culturing the cells from step (a) under conditions favoring the formation of embryoid bodies; and
    (c) culturing the embryoid bodies under conditions favoring the formation of pancreas-spheres co-expressing PDX1, HNF1β, HNF6, and Sox9 proteins.

16. The method of claim 15, wherein the culture conditions in step (c) include culturing the embryoid bodies in a serum-free medium containing insulin, transferrin, selenium, FGF7, nicotinamide, islet neogenesis associated peptide, and exendin-4.

17. The method of claim 15 further comprising culturing the pancreas-spheres under conditions to obtain endocrine specification and differentiation of PDX1$^+$Ins$^+$ cells.

18. The method of claim 15, wherein the fibroblast growth factor comprises bFGF and the bone morphogenetic protein comprises BMP4.

19. The method of claim 15, wherein the pancreas-spheres of step (c) are cultured in a suspension culture comprising a serum-free medium containing B27 and nicotinamide.

20. The method of claim 17, wherein the PDX1$^+$Ins$^+$ cells express increased levels of insulin compared to the pancreas-spheres.

21. The method of claim 17, wherein the PDX1$^+$Ins$^+$ cells secrete C-peptide.

22. A method of producing progenitor cells of the pancreatic lineage, comprising the steps of:
(a) seeding human pluripotent stem cells in a cell culture vessel comprising an upper chamber and a lower chamber, wherein a bottom surface of the upper chamber comprises a porous substrate;
(b) culturing the cells in a chemically defined medium comprising an effective amount of
  i) fibroblast growth factor,
  ii) Activin A, and
  iii) bone morphogenetic protein; and
(c) obtaining pancreatic progenitor PDX1$^+$Ins$^-$ cells.

23. The method of claim 22, wherein the porous substrate comprises pores having a size that restricts migration of cells seeded thereon between the upper and lower chambers and enables the upper and lower chambers to be in fluid communication with one another.

24. The method of claim 23, wherein the pores have a size ranging from 0.01 µm to 3 µm (±10%).

25. The method of claim 22, wherein the PDX1$^+$Ins$^-$ cells can be maintained in culture for at least 70 days.

26. A pancreatic progenitor cell culture implant platform, comprising:
(a) a bicameral cell culture system with an upper chamber and a lower chamber separated by a porous substrate; and
(b) stem cells cultured in the upper chamber on the porous substrate in a chemically defined medium comprising an effective amount of i) fibroblast growth factor, ii) Activin A, and iii) bone morphogenetic protein.

* * * * *